US012558218B2

(12) United States Patent
Landon et al.

(10) Patent No.: US 12,558,218 B2
(45) Date of Patent: Feb. 24, 2026

(54) STEERABLE DELIVERY SYSTEM AND COMPONENTS

(71) Applicant: Edwards Lifesciences Corporation, Irvine, CA (US)

(72) Inventors: David Robert Landon, Huntington Beach, CA (US); Alexander H. Cooper, Costa Mesa, CA (US); Julio Cesar Sanchez, Garden Grove, CA (US); Glen T. Rabito, Lake Forest, CA (US); Jeremy Brent Ratz, Winchester, MA (US); Tarannum Ishaq Gutierrez, Ladera Ranch, CA (US); Ramon Aguilar, Jr., Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 819 days.

(21) Appl. No.: 17/469,817

(22) Filed: Sep. 8, 2021

(65) Prior Publication Data

US 2021/0401575 A1     Dec. 30, 2021

Related U.S. Application Data

(63) Continuation of application No. 16/027,974, filed on Jul. 5, 2018, now Pat. No. 11,123,186.
(Continued)

(51) Int. Cl.
*A61F 2/24* (2006.01)
*A61M 25/00* (2006.01)
(Continued)

(52) U.S. Cl.
CPC ............ *A61F 2/2436* (2013.01); *A61F 2/243* (2013.01); *A61F 2/2439* (2013.01);
(Continued)

(58) Field of Classification Search
CPC .... A61F 2/2436; A61F 2/9517; A61F 2/2427; A61M 25/0105; A61M 25/0147; A61M 2025/015
See application file for complete search history.

(56) References Cited

U.S. PATENT DOCUMENTS

| | | | |
|---|---|---|---|
| 3,409,013 A | 11/1968 | Berry | |
| 3,472,230 A | 10/1969 | Fogarty | |

(Continued)

FOREIGN PATENT DOCUMENTS

| | | | |
|---|---|---|---|
| CA | 2304325 A1 | 10/2000 | |
| CA | 2827556 A1 | 7/2012 | |

(Continued)

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
(Continued)

*Primary Examiner* — Sarah A Long
(74) *Attorney, Agent, or Firm* — Thomas C. Richardson

(57) ABSTRACT

Devices, systems and methods are described herein to provide improved steerability for delivering a prosthesis to a body location, for example, for delivering a replacement valve to a native valve location in a heart. Disclosed are a number of features that can improve steerability or release of the prosthesis into the body location. In one preferred delivery system, a proximal handle can be manipulated to apply tension to a pair of diametrically opposed axial runner wires extending through lumens in a wall of a flexible tubular shaft. By applying tension to a pair of axial runner wires, the tubular shaft can be stiffened along a plane extending substantially through the pair of axial runner wires, while the shaft is permitted to freely bend in a perpendicular plane. This feature advantageously provides
(Continued)

the ability to adjust the steerability and flexibility of a tubular shaft to meet the requirements of a particular procedure.

15 Claims, 57 Drawing Sheets

Related U.S. Application Data

(60) Provisional application No. 62/635,421, filed on Feb. 26, 2018, provisional application No. 62/529,394, filed on Jul. 6, 2017.

(51) Int. Cl.
| | |
|---|---|
| *A61M 25/01* | (2006.01) |
| *A61F 2/95* | (2013.01) |

(52) U.S. Cl.
CPC ...... *A61M 25/005* (2013.01); *A61M 25/0054* (2013.01); *A61M 25/0147* (2013.01); *A61F 2/2418* (2013.01); *A61F 2/9517* (2020.05)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,011,947 A | 3/1977 | Sawyer |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,573,520 A | 11/1996 | Schwartz et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,944,690 A | 8/1999 | Falwell et al. |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goecoechea et al. |

(56)         References Cited

U.S. PATENT DOCUMENTS

| | | |
|---|---|---|
| 6,306,141 B1 | 10/2001 | Jervis |
| 6,312,465 B1 | 11/2001 | Griffin et al. |
| 6,338,740 B1 | 1/2002 | Carpentier |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,800 B1 | 3/2003 | McGuckin, Jr. et al. |
| 6,527,979 B2 | 3/2003 | Constantz |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,622,367 B1 | 9/2003 | Bolduc et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,329,278 B2 | 2/2008 | Seguin et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |

(56)  References Cited

U.S. PATENT DOCUMENTS

| | | | |
|---|---|---|---|
| 8,591,570 B2 | 11/2013 | Revuelta et al. | |
| 8,597,348 B2 | 12/2013 | Rowe et al. | |
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,202 B2 | 2/2014 | Alon et al. | |
| 8,652,203 B2 | 2/2014 | Quadri et al. | |
| 8,668,733 B2 | 3/2014 | Haug et al. | |
| 8,673,000 B2 | 3/2014 | Tabor et al. | |
| 8,679,174 B2 | 3/2014 | Ottma et al. | |
| 8,679,404 B2 | 3/2014 | Liburd et al. | |
| 8,685,086 B2 | 4/2014 | Navia et al. | |
| 8,721,708 B2 | 5/2014 | Seguin et al. | |
| 8,721,714 B2 | 5/2014 | Kelley | |
| 8,728,154 B2 | 5/2014 | Alkhatib | |
| 8,728,155 B2 | 5/2014 | Montorfano et al. | |
| 8,740,974 B2 | 6/2014 | Lambrecht et al. | |
| 8,740,976 B2 | 6/2014 | Tran et al. | |
| 8,747,458 B2 | 6/2014 | Tuval et al. | |
| 8,747,459 B2 | 6/2014 | Nguyen et al. | |
| 8,747,460 B2 | 6/2014 | Tuval et al. | |
| 8,758,432 B2 | 6/2014 | Solem | |
| 8,764,818 B2 | 7/2014 | Gregg | |
| 8,771,344 B2 | 7/2014 | Tran et al. | |
| 8,771,345 B2 | 7/2014 | Tuval et al. | |
| 8,771,346 B2 | 7/2014 | Tuval et al. | |
| 8,778,020 B2 | 7/2014 | Gregg et al. | |
| 8,784,337 B2 | 7/2014 | Voeller et al. | |
| 8,784,478 B2 | 7/2014 | Tuval et al. | |
| 8,784,481 B2 | 7/2014 | Alkhatib et al. | |
| 8,790,387 B2 | 7/2014 | Nguyen et al. | |
| 8,795,356 B2 | 8/2014 | Quadri et al. | |
| 8,795,357 B2 | 8/2014 | Yohanan et al. | |
| 8,808,356 B2 | 8/2014 | Braido et al. | |
| 8,828,078 B2 | 9/2014 | Salahieh et al. | |
| 8,828,079 B2 | 9/2014 | Thielen et al. | |
| 8,834,564 B2 | 9/2014 | Tuval et al. | |
| 8,845,718 B2 | 9/2014 | Tuval et al. | |
| 8,858,620 B2 | 10/2014 | Salahieh et al. | |
| 8,870,948 B1 | 10/2014 | Erzberger et al. | |
| 8,870,950 B2 | 10/2014 | Hacohen | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,911,455 B2 | 12/2014 | Quadri et al. | |
| 8,926,693 B2 | 1/2015 | Duffy et al. | |
| 8,926,694 B2 | 1/2015 | Costello | |
| 8,939,960 B2 | 1/2015 | Rosenman et al. | |
| 8,945,209 B2 | 2/2015 | Bonyuet et al. | |
| 8,951,299 B2 | 2/2015 | Paul et al. | |
| 8,961,593 B2 | 2/2015 | Bonhoeffer et al. | |
| 8,961,595 B2 | 2/2015 | Alkhatib | |
| 8,974,524 B2 | 3/2015 | Yeung et al. | |
| 8,979,922 B2 | 3/2015 | Jayasinghe et al. | |
| 8,986,372 B2 | 3/2015 | Murry, III et al. | |
| 8,986,375 B2 | 3/2015 | Garde et al. | |
| 8,992,608 B2 | 3/2015 | Haug et al. | |
| 8,998,979 B2 | 4/2015 | Seguin et al. | |
| 8,998,980 B2 | 4/2015 | Shipley et al. | |
| 9,005,273 B2 | 4/2015 | Salahieh et al. | |
| 9,011,521 B2 | 4/2015 | Haug et al. | |
| 9,011,523 B2 | 4/2015 | Seguin | |
| 9,011,524 B2 | 4/2015 | Eberhardt | |
| 9,028,545 B2 | 5/2015 | Taylor | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,055,937 B2 | 6/2015 | Rowe et al. | |
| 9,066,801 B2 | 6/2015 | Kovalsky et al. | |
| 9,078,749 B2 | 7/2015 | Lutter et al. | |
| 9,078,751 B2 | 7/2015 | Naor | |
| 9,084,676 B2 | 7/2015 | Chau et al. | |
| 9,125,738 B2 | 9/2015 | Figulla et al. | |
| 9,138,312 B2 | 9/2015 | Tuval et al. | |
| 9,161,834 B2 | 10/2015 | Taylor et al. | |
| 9,173,737 B2 | 11/2015 | Hill et al. | |
| 9,180,004 B2 | 11/2015 | Alkhatib | |
| 9,186,249 B2 | 11/2015 | Rolando et al. | |
| 9,220,594 B2 | 12/2015 | Braido et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| 9,289,291 B2 | 3/2016 | Gorman, III et al. | |
| 9,289,296 B2 | 3/2016 | Braido et al. | |
| 9,295,551 B2 | 3/2016 | Straubinger et al. | |
| 9,326,815 B2 | 5/2016 | Watson | |
| 9,331,328 B2 | 5/2016 | Eberhardt et al. | |
| 9,339,382 B2 | 5/2016 | Tabor et al. | |
| 9,351,831 B2 | 5/2016 | Braido et al. | |
| 9,351,832 B2 | 5/2016 | Braido et al. | |
| 9,364,321 B2 | 6/2016 | Alkhatib et al. | |
| 9,445,897 B2 | 9/2016 | Bishop et al. | |
| 9,456,877 B2 | 10/2016 | Weitzner et al. | |
| 9,681,968 B2 | 6/2017 | Goetz et al. | |
| 9,687,345 B2 | 6/2017 | Rabito et al. | |
| 9,700,329 B2 | 7/2017 | Metzger et al. | |
| 9,700,411 B2 | 7/2017 | Klima et al. | |
| 9,724,083 B2 | 8/2017 | Quadri et al. | |
| 9,730,790 B2 | 8/2017 | Quadri et al. | |
| 9,730,791 B2 | 8/2017 | Ratz et al. | |
| 9,795,479 B2 | 10/2017 | Lim et al. | |
| 9,833,313 B2 | 12/2017 | Board et al. | |
| 9,861,473 B2 | 1/2018 | Lafontaine | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |
| 9,889,029 B2 | 2/2018 | Li et al. | |
| 9,895,225 B2 | 2/2018 | Rolando et al. | |
| 9,925,045 B2 | 3/2018 | Creaven et al. | |
| 10,004,599 B2 | 6/2018 | Rabito et al. | |
| 10,065,015 B2 | 9/2018 | Leeflang et al. | |
| 10,076,638 B2 | 9/2018 | Tran et al. | |
| 10,117,744 B2 | 11/2018 | Ratz et al. | |
| 10,179,044 B2 | 1/2019 | Ratz et al. | |
| 10,219,897 B2 | 3/2019 | Essinger et al. | |
| 10,350,065 B2 | 7/2019 | Quadri | |
| 10,350,066 B2 | 7/2019 | Cooper et al. | |
| 10,376,363 B2 | 8/2019 | Quadri et al. | |
| 10,555,809 B2 | 2/2020 | Hastings et al. | |
| 10,575,951 B2 | 3/2020 | Johnson et al. | |
| 10,583,000 B2 | 3/2020 | Ratz et al. | |
| 10,639,146 B2 | 5/2020 | Quadri et al. | |
| 10,695,177 B2 | 6/2020 | Hariton et al. | |
| 10,758,344 B2 | 9/2020 | Hariton et al. | |
| 11,406,499 B2 | 8/2022 | Zhang et al. | |
| 11,452,598 B2 | 9/2022 | Essinger et al. | |
| 11,672,658 B2 | 6/2023 | Hariton et al. | |
| 11,701,225 B2 | 7/2023 | Hammer et al. | |
| 11,903,829 B1 | 2/2024 | Ma et al. | |
| 2001/0007956 A1 | 7/2001 | Letac et al. | |
| 2001/0021872 A1 | 9/2001 | Bailey et al. | |
| 2002/0016623 A1 | 2/2002 | Kula et al. | |
| 2002/0032481 A1 | 3/2002 | Gabbay | |
| 2002/0045929 A1 | 4/2002 | Diaz | |
| 2002/0052644 A1 | 5/2002 | Shaolian et al. | |
| 2002/0072710 A1 | 6/2002 | Stewart et al. | |
| 2002/0107565 A1 | 8/2002 | Greenhalgh | |
| 2002/0123802 A1 | 9/2002 | Snyders | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0105517 A1 | 6/2003 | White et al. | |
| 2003/0114913 A1 | 6/2003 | Spenser et al. | |
| 2003/0120333 A1 | 6/2003 | Ouriel et al. | |
| 2003/0130729 A1 | 7/2003 | Paniagua et al. | |
| 2003/0149477 A1 | 8/2003 | Gabbay | |
| 2003/0149478 A1 | 8/2003 | Figulla et al. | |
| 2003/0158597 A1 | 8/2003 | Quiachon et al. | |
| 2003/0176914 A1 | 9/2003 | Rabkin et al. | |
| 2003/0199971 A1 | 10/2003 | Tower et al. | |

(56) References Cited

U.S. PATENT DOCUMENTS

| | | |
|---|---|---|
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0093075 A1 | 5/2004 | Kuehne |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186561 A1 | 9/2004 | McGuckin et al. |
| 2004/0186563 A1 | 9/2004 | Lobbi |
| 2004/0186565 A1 | 9/2004 | Schreck |
| 2004/0193193 A1 | 9/2004 | Laufer et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0043682 A1 | 2/2005 | Kucklick et al. |
| 2005/0070844 A1 | 3/2005 | Chow et al. |
| 2005/0075727 A1 | 4/2005 | Wheatley |
| 2005/0090887 A1 | 4/2005 | Pryor |
| 2005/0090890 A1 | 4/2005 | Wu et al. |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137693 A1 | 6/2005 | Haug et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100687 A1 | 5/2006 | Fahey et al. |
| 2006/0135961 A1 | 6/2006 | Rosenman et al. |
| 2006/0135962 A1 | 6/2006 | Kick et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0276874 A1 | 12/2006 | Wilson et al. |
| 2006/0287717 A1 | 12/2006 | Rowe et al. |
| 2006/0293745 A1 | 12/2006 | Carpentier et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0243081 A1 | 10/2008 | Nance et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0099554 A1 | 4/2009 | Forster et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0024818 A1 | 2/2010 | Stenzler et al. |
| 2010/0049313 A1 | 2/2010 | Alon et al. |
| 2010/0069852 A1 | 3/2010 | Kelley |
| 2010/0069882 A1 | 3/2010 | Jennings et al. |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0145438 A1 | 6/2010 | Barone |
| 2010/0174362 A1 | 7/2010 | Straubinger et al. |
| 2010/0191326 A1 | 7/2010 | Alkhatib |

(56) References Cited

U.S. PATENT DOCUMENTS

| | | |
|---|---|---|
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0015616 A1 | 1/2011 | Straubinger et al. |
| 2011/0015729 A1 | 1/2011 | Jimenez et al. |
| 2011/0029067 A1 | 2/2011 | McGuckin, Jr. et al. |
| 2011/0029072 A1 | 2/2011 | Gabbay |
| 2011/0098804 A1 | 4/2011 | Yeung et al. |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray, III et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0016192 A1 | 1/2012 | Jansen et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0059454 A1 | 3/2012 | Millwee et al. |
| 2012/0078351 A1 | 3/2012 | Klima et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0172920 A1 | 7/2012 | Fifer et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0239142 A1 | 9/2012 | Liu et al. |
| 2012/0253131 A1 | 10/2012 | Malkowski et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0030519 A1 | 1/2013 | Tran et al. |
| 2013/0030520 A1 | 1/2013 | Lee et al. |
| 2013/0035759 A1 | 2/2013 | Gross et al. |
| 2013/0053766 A1* | 2/2013 | Hollett ............ A61M 25/09041 |
| | | 604/95.01 |
| 2013/0053950 A1 | 2/2013 | Rowe et al. |
| 2013/0073035 A1 | 3/2013 | Tuval et al. |
| 2013/0079869 A1 | 3/2013 | Straubinger et al. |
| 2013/0131788 A1 | 5/2013 | Quadri et al. |
| 2013/0144378 A1 | 6/2013 | Quadri et al. |
| 2013/0172992 A1 | 7/2013 | Gross et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0031922 A1 | 1/2014 | Duffy et al. |
| 2014/0039611 A1 | 2/2014 | Lane et al. |
| 2014/0052109 A1* | 2/2014 | Organ ............ A61M 25/09025 |
| | | 604/528 |
| 2014/0052237 A1 | 2/2014 | Lane et al. |
| 2014/0052242 A1 | 2/2014 | Revuelta et al. |
| 2014/0088565 A1 | 3/2014 | Vongphakdy et al. |
| 2014/0100651 A1 | 4/2014 | Kheradvar et al. |
| 2014/0100653 A1 | 4/2014 | Savage et al. |
| 2014/0135909 A1 | 5/2014 | Carr et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214157 A1 | 7/2014 | Bortlein et al. |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277403 A1 | 9/2014 | Peter |
| 2014/0277412 A1 | 9/2014 | Bortlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309661 A1 | 10/2014 | Sheps et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0073539 A1* | 3/2015 | Geiger .................. A61F 2/2439 |
| | | 623/2.11 |
| 2015/0127093 A1 | 5/2015 | Hosmer et al. |
| 2015/0142100 A1 | 5/2015 | Morriss et al. |
| 2015/0142103 A1 | 5/2015 | Vidlund |
| 2015/0148731 A1 | 5/2015 | McNamara et al. |
| 2015/0157457 A1 | 6/2015 | Hacohen |

(56)                    References Cited

U.S. PATENT DOCUMENTS

| | | |
|---|---|---|
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0238315 A1 | 8/2015 | Rabito et al. |
| 2015/0272737 A1 | 10/2015 | Dale et al. |
| 2015/0297346 A1 | 10/2015 | Duffy et al. |
| 2015/0297381 A1 | 10/2015 | Essinger et al. |
| 2015/0305865 A1 | 10/2015 | Taylor |
| 2015/0305867 A1 | 10/2015 | Liu et al. |
| 2015/0327994 A1 | 11/2015 | Morriss et al. |
| 2015/0328000 A1 | 11/2015 | Ratz et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0022961 A1 | 1/2016 | Rosenman et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038280 A1 | 2/2016 | Morriss et al. |
| 2016/0038281 A1 | 2/2016 | Delaloye et al. |
| 2016/0045311 A1 | 2/2016 | McCann et al. |
| 2016/0074160 A1 | 3/2016 | Christianson et al. |
| 2016/0100746 A1 | 4/2016 | Okazaki et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0158497 A1 | 6/2016 | Tran et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2016/0317301 A1* | 11/2016 | Quadri ................. A61F 2/2418 |
| 2016/0339207 A1* | 11/2016 | Beeckler ........... A61M 25/0141 |
| 2017/0035567 A1 | 2/2017 | Duffy |
| 2017/0042678 A1 | 2/2017 | Ganesan et al. |
| 2017/0056171 A1 | 3/2017 | Cooper et al. |
| 2017/0079785 A1 | 3/2017 | Li |
| 2017/0128197 A1 | 5/2017 | Bialas et al. |
| 2017/0128209 A1 | 5/2017 | Morriss et al. |
| 2017/0165064 A1 | 6/2017 | Nyuli et al. |
| 2017/0182290 A1 | 6/2017 | Stern |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0028787 A1 | 2/2018 | McNiven et al. |
| 2018/0049873 A1 | 2/2018 | Manash et al. |
| 2018/0055629 A1 | 3/2018 | Oba et al. |
| 2018/0055636 A1 | 3/2018 | Valencia et al. |
| 2018/0085027 A1* | 3/2018 | Kimmel ............... G01R 33/287 |
| 2018/0085218 A1 | 3/2018 | Eidenschink |
| 2018/0110534 A1 | 4/2018 | Gavala et al. |
| 2018/0110622 A1 | 4/2018 | Gregg et al. |
| 2018/0116790 A1 | 5/2018 | Ratz et al. |
| 2018/0126119 A1 | 5/2018 | McNiven et al. |
| 2018/0206983 A1 | 7/2018 | Noe et al. |
| 2018/0214664 A1 | 8/2018 | Kim et al. |
| 2018/0296341 A1 | 10/2018 | Noe et al. |
| 2018/0344457 A1 | 12/2018 | Gross et al. |
| 2018/0344490 A1 | 12/2018 | Fox et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2019/0298557 A1 | 10/2019 | Murray, III |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0323668 A1 | 10/2020 | Diedering et al. |
| 2020/0345493 A1 | 11/2020 | Gregg et al. |
| 2020/0345494 A1 | 11/2020 | Srinimukesh et al. |
| 2020/0352718 A1 | 11/2020 | Rowe et al. |
| 2021/0015615 A1 | 1/2021 | Groothuis et al. |
| 2021/0145576 A1 | 5/2021 | Becerra et al. |
| 2021/0154010 A1 | 5/2021 | Schneider et al. |
| 2021/0228354 A1 | 7/2021 | Rafiee et al. |
| 2021/0259835 A1 | 8/2021 | Tyler, II et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2022/0401243 A1 | 12/2022 | Diedering et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1469797 A1 | 10/2004 |
| EP | 1472996 A1 | 11/2004 |
| EP | 1570809 A1 | 9/2005 |
| EP | 1653888 A2 | 5/2006 |
| EP | 1734903 A1 | 12/2006 |
| EP | 1827558 A2 | 9/2007 |
| EP | 1239901 B1 | 10/2007 |
| EP | 1849440 A1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2413842 A1 | 2/2012 |

(56) References Cited

FOREIGN PATENT DOCUMENTS

| | | | |
|---|---|---|---|
| EP | 2496182 | A1 | 9/2012 |
| EP | 2566416 | A1 | 3/2013 |
| EP | 2745805 | A1 | 6/2014 |
| EP | 2749254 | A1 | 7/2014 |
| EP | 2750630 | A1 | 7/2014 |
| EP | 2777616 | A1 | 9/2014 |
| EP | 2777617 | A1 | 9/2014 |
| EP | 2815723 | A1 | 12/2014 |
| EP | 2815725 | A1 | 12/2014 |
| EP | 2898858 | A1 | 7/2015 |
| EP | 2918249 | A2 | 9/2015 |
| EP | 2948103 | A2 | 12/2015 |
| EP | 2967858 | A2 | 1/2016 |
| EP | 2926766 | B1 | 2/2016 |
| EP | 2985006 | A1 | 2/2016 |
| EP | 2168536 | B1 | 4/2016 |
| EP | 3075354 | A2 | 10/2016 |
| EP | 3139864 | A1 | 3/2017 |
| EP | 2262451 | B1 | 5/2017 |
| EP | 3184083 | A1 | 6/2017 |
| EP | 2446915 | B1 | 1/2018 |
| EP | 3057541 | B1 | 1/2018 |
| EP | 3037064 | B1 | 3/2018 |
| EP | 3046511 | B1 | 3/2018 |
| EP | 3142603 | B1 | 3/2018 |
| EP | 3294220 | A1 | 3/2018 |
| EP | 3417813 | A1 | 12/2018 |
| EP | 3570779 | A1 | 11/2019 |
| EP | 2918249 | B1 | 4/2020 |
| FR | 2788217 | A1 | 7/2000 |
| GB | 1264471 | A | 2/1972 |
| GB | 1315844 | A | 5/1973 |
| GB | 2056023 | A | 3/1981 |
| GB | 2398245 | A | 8/2004 |
| JP | 2002540889 | A | 12/2002 |
| JP | 2008541865 | A | 11/2008 |
| SU | 1271508 | A1 | 11/1986 |
| WO | 9116041 | A1 | 10/1991 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9749355 | A1 | 12/1997 |
| WO | 9829057 | A1 | 7/1998 |
| WO | 9933414 | A1 | 7/1999 |
| WO | 9940964 | A1 | 8/1999 |
| WO | 9947075 | A1 | 9/1999 |
| WO | 0041652 | A1 | 7/2000 |
| WO | 0047139 | A1 | 8/2000 |
| WO | 0061034 | A1 | 10/2000 |
| WO | 0236048 | A1 | 5/2002 |
| WO | WO-2002041789 | A2 | 5/2002 |
| WO | 03047468 | A1 | 6/2003 |
| WO | 03092554 | A1 | 11/2003 |
| WO | 2004030569 | A2 | 4/2004 |
| WO | 2005011534 | A1 | 2/2005 |
| WO | 2005034812 | A1 | 4/2005 |
| WO | WO-2005062980 | A2 | 7/2005 |
| WO | 2005087140 | A1 | 9/2005 |
| WO | 2005102015 | A2 | 11/2005 |
| WO | 2006014233 | A2 | 2/2006 |
| WO | 2006034008 | A2 | 3/2006 |
| WO | 2006070372 | A2 | 7/2006 |
| WO | 2006085225 | A1 | 8/2006 |
| WO | 2006089236 | A1 | 8/2006 |
| WO | 2006108090 | A2 | 10/2006 |
| WO | 2006111391 | A1 | 10/2006 |
| WO | 2006127765 | A1 | 11/2006 |
| WO | 2006138173 | A2 | 12/2006 |
| WO | 2007025028 | A1 | 3/2007 |
| WO | 2007058857 | A2 | 5/2007 |
| WO | 2007123658 | A1 | 11/2007 |
| WO | 2008005405 | A2 | 1/2008 |
| WO | 2008013915 | A2 | 1/2008 |
| WO | 2008035337 | A2 | 3/2008 |
| WO | 2008070797 | A2 | 6/2008 |
| WO | 2008103722 | A2 | 8/2008 |
| WO | 2008125153 | A1 | 10/2008 |
| WO | 2008147964 | A1 | 12/2008 |
| WO | 2008150529 | A1 | 12/2008 |
| WO | 2009024859 | A2 | 2/2009 |
| WO | 2009026563 | A2 | 2/2009 |
| WO | 2009033469 | A1 | 3/2009 |
| WO | 2009042196 | A2 | 4/2009 |
| WO | 2009045331 | A1 | 4/2009 |
| WO | 2009053497 | A1 | 4/2009 |
| WO | 2009091509 | A1 | 7/2009 |
| WO | 2009094500 | A1 | 7/2009 |
| WO | WO-2009116041 | A2 | 9/2009 |
| WO | 2009134701 | A2 | 11/2009 |
| WO | 2010005524 | A2 | 1/2010 |
| WO | 2010008549 | A1 | 1/2010 |
| WO | 2010022138 | A2 | 2/2010 |
| WO | 2010037141 | A1 | 4/2010 |
| WO | 2010040009 | A1 | 4/2010 |
| WO | 2010057262 | A1 | 5/2010 |
| WO | 2010121076 | A2 | 10/2010 |
| WO | 2011002996 | A2 | 1/2011 |
| WO | 2011008538 | A1 | 1/2011 |
| WO | 2011025945 | A1 | 3/2011 |
| WO | 2011057087 | A1 | 5/2011 |
| WO | 2011081997 | A1 | 7/2011 |
| WO | 2011111047 | A2 | 9/2011 |
| WO | 2011137531 | A1 | 11/2011 |
| WO | 2012008459 | A1 | 1/2012 |
| WO | 2012032187 | A1 | 3/2012 |
| WO | 2012095455 | A2 | 7/2012 |
| WO | 2012177942 | A2 | 12/2012 |
| WO | 2013005878 | A1 | 1/2013 |
| WO | 2013028387 | A2 | 2/2013 |
| WO | 2013075215 | A1 | 5/2013 |
| WO | 2013106585 | A1 | 7/2013 |
| WO | 2013120181 | A1 | 8/2013 |
| WO | 2013175468 | A2 | 11/2013 |
| WO | 2013192305 | A2 | 12/2013 |
| WO | 2014009213 | A1 | 1/2014 |
| WO | 2014018432 | A2 | 1/2014 |
| WO | 2014079291 | A1 | 5/2014 |
| WO | 2014099655 | A1 | 6/2014 |
| WO | 2014110019 | A1 | 7/2014 |
| WO | 2014110171 | A2 | 7/2014 |
| WO | 2014121042 | A1 | 8/2014 |
| WO | 2014139545 | A1 | 9/2014 |
| WO | 2014145338 | A1 | 9/2014 |
| WO | 2014149865 | A1 | 9/2014 |
| WO | 2014163706 | A1 | 10/2014 |
| WO | 2014164364 | A1 | 10/2014 |
| WO | 2014194178 | A1 | 12/2014 |
| WO | 2014204807 | A1 | 12/2014 |
| WO | 2014205064 | A1 | 12/2014 |
| WO | 2014210124 | A1 | 12/2014 |
| WO | 2015004624 | A1 | 1/2015 |
| WO | 2015004625 | A1 | 1/2015 |
| WO | 2015057407 | A1 | 4/2015 |
| WO | 2015077274 | A1 | 5/2015 |
| WO | 2015148241 | A1 | 10/2015 |
| WO | 2016002189 | A1 | 1/2016 |
| WO | 2016004137 | A1 | 1/2016 |
| WO | 2016016899 | A1 | 2/2016 |
| WO | 2017006510 | A1 | 1/2017 |
| WO | 2017035487 | A1 | 3/2017 |
| WO | 2018000333 | A1 | 1/2018 |
| WO | 2018213209 | A1 | 11/2018 |
| WO | 2022002054 | A1 | 1/2022 |
| WO | 2023006048 | A1 | 2/2023 |
| WO | 2023076103 | A1 | 5/2023 |
| WO | 2023081236 | A1 | 5/2023 |
| WO | 2023091769 | A1 | 5/2023 |
| WO | 2023096804 | A1 | 6/2023 |
| WO | 2023154250 | A1 | 8/2023 |
| WO | 2023196150 | A1 | 10/2023 |
| WO | 2023244454 | A1 | 12/2023 |
| WO | 2023244767 | A1 | 12/2023 |
| WO | 2023250114 | A1 | 12/2023 |

(56) References Cited

FOREIGN PATENT DOCUMENTS

| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as December of 2006.

Vu, Duc-Thang, et al., "Novel Sutureless Mitral Valve Implantation Method Involving A Bayonet Insertion And Release Mechanism: A Proof Of Concept Study In Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design And Evolution," International Journal of Cardiology 168 (2013) 1822-1831, Applicant believes this may have been available as early as Oct. 3, 2013.

Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents For Off-Pump Mitral Valve Replacement," European Journal of Cardio-thoracic Surgery 28 (2005) 194-199, Applicant believes this may have been available as early as August of 2005.

Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—

TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Ratz, J. Brent, "In3 Company Overview," Jun. 24, 2009.

"Company Overview," at TVT on Jun. 25, 2009.

Ruiz, Carlos E., "Overview of Novel Transcatheter Valve Technologies," Applicant believes this may have been presented on May 27, 2010 at EuroPCR.

"Update," Applicant believes this may have been presented on Jun. 6, 2010 at TVT.

Mack, Michael, M.D., "Antegrade Transcatheter Mitral valve Implantation: A Short-term Experience in Swine Model," Applicant believes this may have been presented on May of 2011 at TVT.

Mack, Michael, M.D., "Antegrade Transcatheter Mitral valve Implantation: On-Going Experience in Swine Model," Applicant believes this may have been presented on November of 2011 at TCT.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Quadri, Arshad M.D., "Transcatheter Mitral Valve Implantation (TMVI) (An Acute In Vivo Study)," Applicant believes this may have been presented on Sep. 22, 2010 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Horvath et al.: "Transapical Aortic Valve Replacement under Real-time Magnetic Resonance Imaging Guidance: Experimental Results with Balloon- Expandable and Self-Expanding Stents," http://www.ncbi.nlm.nih.gov/pmc/articles/PMC3038190/. Jun. 2011.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=removeffaccess. Jan. 21, 2014.

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Piazza, Nicoló, MD, et al., "Anatomy of the Aortic Valvar Complex and Its Implications for Transcatheter Implantation of the Aortic Valve," Contemporary Reviews in Interventional Cardiology, Circ.

(56) References Cited

OTHER PUBLICATIONS

Cardiovasc. Intervent., 2008;1:74-81, Applicant believes this may have been available as early as August of 2008.

Feldman, Ted, MD. "Prospects for Percutaneous Valve Therapies," Circulation 2007;116:2866-2877. Applicant believes that this may be available as early as Dec. 11, 2007.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.piospace.com/News/cardiaq-valve-technologies-cvt-reports/263900.

Biospace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

"CardiAQTM Valve Technologies reports Successful First-in-Human Trans-Apical implantation of its Second Generation Transcatheter Mitral Valve," CardiAQ Valve Technologies Press Release, May 20, 2014.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Banai, Shmeul et al., The Journal of the American College of Cardiology, "Transapical Mitral Implantation of the Tiara Bioprosthesis Pre-Clinical Results," Feb. 2014, <http://interventions.onlinejacc. org/article.aspx? articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

NJ350: Vote for Your Favorite New Jersey Innovations, Jun. 27, 2014, http://www.kilmerhouse.com/2014/06/nj350-vote-for-your-favorite-new-jersey-innovations/.

Mack, Michael M.D., "Advantages and Limitations of Surgical Mitral Valve Replacement; Lessons for the Transcatheter Approach,"

Applicant believes this may have been available as early as Jun. 7, 2010. Applicant believes this may have been presented at the Texas Cardiovascular Innovative Ventures (TCIV) Conference in Dallas, TX on Dec. 8, 2010.

Bavaria, Joseph E. M.D. et al.: "Transcatheter Mitral Valve Implantation: The Future Gold Standard for MR?," Applicant requests the Examiner to consider this reference to be prior art as of December of 2010.

Andersen, et al., "Transluminal implantation of artificial heart valves. Description ofa new expandable aortic valve and initial results with implantation by cathetertechnique in closed chest pigs." European Heart Journal (1992), 13, 704-708

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Wheatley, M.D., David J., "Valve Prostheses," Rob & Smith's Operative Surgery, Fourth Edition, pp. 415-424, Butterworths 1986.

Medtronic, "Transcatheter Aortic Valve Delivery Catheter System Compression Loading System", Core Valve Sytem, 2014, Medtronic Inc., Santa Ana, CA.

Herrmann, Howard C. MD, "Advances in Transseptal Transcatheter Mitral Valve Replacement", tct 2018, Cardiovascular Research Foundation.

Neale, Todd, "Flushing TAVI Valves With Carbon Dioxide May Protect Against Brain Injury", News > Conference News, EuroPCR 2023, TCTMD, May 16, 2023, Paris France.

Wheatley D.J., "Valve Prostheses," Operative Surgery, 4th edition, 1986, pp. 415-424.

* cited by examiner

104

105

103

104

*1100*

*1102*

22

3402 x-axis y-axis

3402

3406

3404

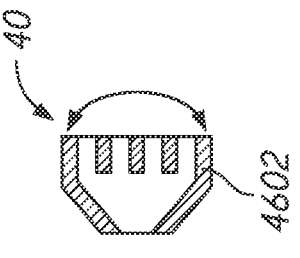
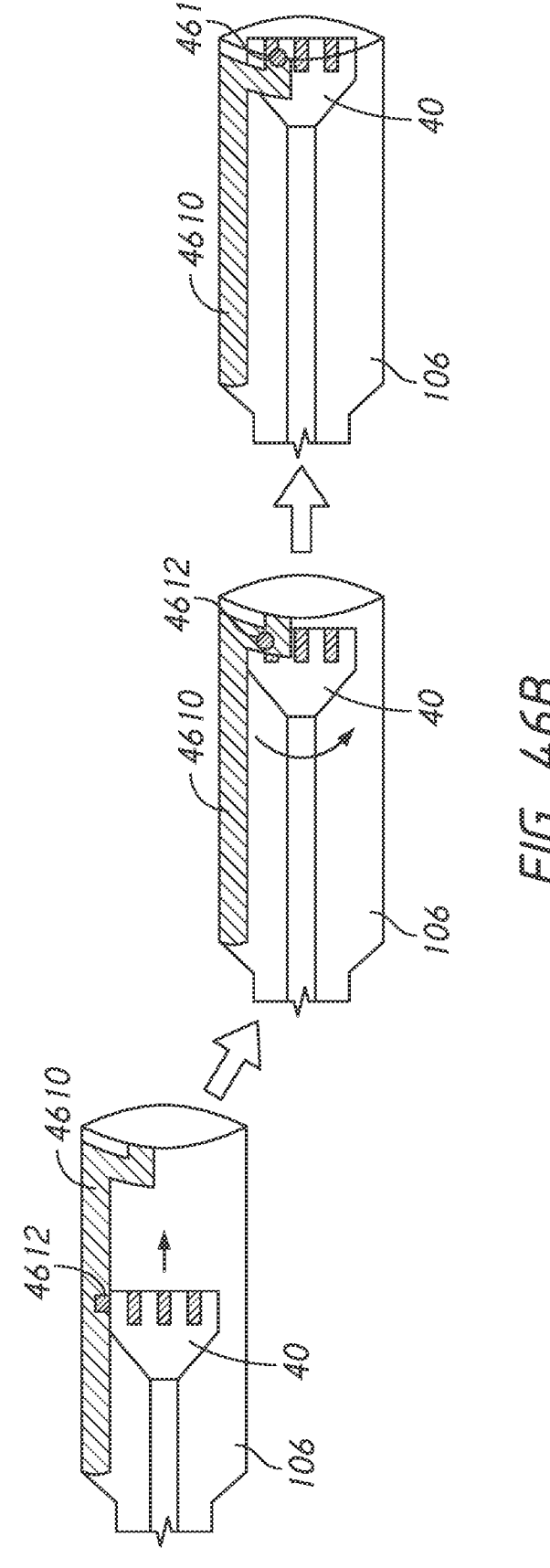
FIG. 46A
FIG. 46B

STEERABLE DELIVERY SYSTEM AND COMPONENTS

PRIORITY CLAIM AND INCORPORATION BY REFERENCE TO ANY PRIORITY APPLICATIONS

This application is a continuation of U.S. application Ser. No. 16/027,974, filed Jul. 5, 2018, now U.S. Pat. No. 11,123,186, which claims the benefit of U.S. Provisional Application No. 62/529,394, filed Jul. 6, 2017, and U.S. Provisional Application No. 62/635,421, filed Feb. 26, 2018, the entirety of each of which is hereby incorporated by reference. Embodiments of this application also relate to and may be combined with embodiments disclosed in U.S. application Ser. No. 16/028,172, filed on Jul. 5, 2018, now U.S. Pat. No. 10,813,757, the entirety of which is hereby incorporated by reference.

BACKGROUND

Field

Certain embodiments disclosed herein relate generally to prostheses for implantation within a lumen or body cavity and delivery systems for a prosthesis. In particular, the prostheses and delivery systems relate to replacement heart valves, such as replacement mitral heart valves.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valve's ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example, delivering a replacement heart valve to the mitral valve, can also be challenging. Attaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

In some embodiments, a delivery system and method are provided for delivering a replacement heart valve to a native mitral valve location. The delivery system and method may utilize a transseptal approach. In some embodiments, components of the delivery system facilitate bending of the delivery system to steer a prosthesis from the septum to a location within the native mitral valve. In some embodiments, a capsule is provided for containing the prosthesis for delivery to the native mitral valve location. In other embodiments, the delivery system and method may be adapted for delivery of implants to locations other than the native mitral valve.

The present disclosure includes, but is not limited to, the following embodiments.

Embodiment 1: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, and an inner assembly located within the outer lumen, the inner assembly comprising an inner shaft having an inner lumen and a proximal end and a distal end, wherein the inner assembly comprises an inner retention member configured to be releasably attached to the expandable implant, and wherein the delivery system is configured to be bent at least at one location to facilitate delivery of the expandable implant to the body location.

Embodiment 2: The delivery system of Embodiment 1, wherein the delivery system further comprises a nose cone assembly located within the inner lumen, the nose cone assembly comprising a nose cone shaft having a guide wire lumen, a proximal and distal end, and a nose cone at the distal end.

Embodiment 3: The delivery system of any one of Embodiments 1-2, wherein the delivery system is configured to form a proximal bend and a distal bend.

Embodiment 4: The delivery system of any one of Embodiments 1-3, wherein the outer shaft comprises a series of slots that rotate around a circumference of the outer shaft from the proximal end to the distal end.

Embodiment 5: The delivery system of any one of Embodiments 1-4, wherein at least a portion of the outer shaft comprises a braided tube attached radially on top of a slotted hypotube.

Embodiment 6: The delivery system of any one of Embodiments 1-5, wherein the outer shaft comprises a capsule at a distal end of the outer shaft forming the implant retention area, the capsule comprising at least 100 circumferentially extending slots along its length.

Embodiment 7: The delivery system of any one of Embodiments 1-5, wherein the outer shaft comprises a capsule at a distal end of the outer shaft forming the implant retention area, wherein the capsule comprises a flarable distal section configured to radially expand.

Embodiment 8: The delivery system of any one of Embodiments 1-7, wherein the inner shaft comprises an outer retention ring slideable along the inner shaft and at least one tab, wherein the at least one tab is moveable between a radially flared position and a radially compressed position, and wherein when the at least one tab is in the radially compressed position, the outer retention ring can slide over the at least one tab, and wherein when the at least one tab is in the radially flared position, the outer retention ring is prevented from moving proximally over the at least one tab.

Embodiment 9: The delivery system of Embodiment Error! Reference source not found., wherein the inner shaft comprises at least one collar at least partially surrounding the inner shaft, wherein the at least one tab is located on the collar, and wherein the collar is configured to translate along the inner shaft.

Embodiment 10: The delivery system of any one of Embodiments 1-9, wherein the delivery system further comprises a steerable sheath surrounding the outer sheath assembly, wherein the steerable sheath is configured to form a first bend at a proximal bend location and a second bend at a distal bend location.

Embodiment 11: The delivery system of Embodiment Error! Reference source not found., wherein the steerable sheath comprises a plurality of circumferential slots, a proximal pull wire attached at the proximal bend location, and a distal pull wire attached at the distal bend location, wherein a proximal force on the proximal pull wire forms the first bend and a proximal force on the distal pull wire forms the second bend.

Embodiment 12: The delivery system of Embodiment Error! Reference source not found., wherein when a proximal force is applied to the distal pull wire, the delivery system is only bent at the second bend location.

Embodiment 13: The delivery system of Embodiment Error! Reference source not found., wherein the steerable sheath comprises a pair of pull wires, wherein the pair of pull wires are circumferentially spaced apart at a proximal end portion of the steerable sheath and are circumferentially adjacent at a distal end portion of the steerable sheath.

Embodiment 14: The delivery system of Embodiment Error! Reference source not found., further comprising a third pull wire located circumferentially between the pair of pull wires at the proximal end portion, wherein the third pull wire meets the pair of pull wires in the distal end portion.

Embodiment 15: The delivery system of Embodiment Error! Reference source not found., wherein the steerable sheath comprises a pair of pull wires, wherein the pull wires are circumferentially adjacent at a proximal end portion of the steerable sheath and are circumferentially spaced apart at a distal end portion of the steerable sheath.

Embodiment 16: The delivery system of any one of Embodiments 1-15, wherein the outer sheath assembly comprises an axial runner containing a pull wire having an untensioned configuration and a tensioned configuration, wherein the outer sheath assembly can bend when the pull wire is in the untensioned configuration and wherein the outer sheath assembly cannot bend when the pull wire is in the tensioned configuration.

Embodiment 17: The delivery system of Embodiment Error! Reference source not found., further comprising four of the axial runners spaced approximately 90 degrees apart, each of the four axial runners containing a pull wire having the untensioned configuration and the tensioned configuration, wherein each of the pull wires can be independently placed under tension.

Embodiment 18: The delivery system of Embodiment 1, wherein the outer sheath assembly comprises a helical backbone having a plurality of circumferentially extending slots along a length of the outer sheath assembly.

Embodiment 19: The delivery system of Embodiment Error! Reference source not found., wherein the helical backbone is longitudinally thicker at a first circumferential portion than at a second circumferential portion.

Embodiment 20: The delivery system of Embodiment Error! Reference source not found., wherein the first circumferential portion is approximately a first circumferential half and the second circumferential portion is approximately a second circumferential half.

Embodiment 21: The delivery system of Embodiment 1, wherein the outer sheath assembly comprises a pull wire, wherein the pull wire extends longitudinally straight at a proximal portion of the outer sheath assembly, and wherein the pull wire extends distally and circumferentially at a distal portion of the outer sheath assembly.

Embodiment 22: The delivery system of any one of Embodiments 1-21, wherein the outer sheath assembly comprises a longitudinally extending slot on at least a portion of an inner surface of the outer sheath assembly, and wherein the inner retention member comprises a tab configured to mate with and follow along the longitudinally extending slot.

Embodiment 23: The delivery system of Embodiment Error! Reference source not found., wherein the slot extends circumferentially along at least a portion of the inner surface of the outer sheath assembly.

Embodiment 24: The delivery system of any one of Embodiments 1-23, wherein the inner retention member comprises a plurality of longitudinally extending slots, and wherein the inner retention member comprises a plurality of rotatable flaps each configured to rotatably cover one of the plurality of longitudinally extending slots.

Embodiment 25: The delivery system of any one of Embodiments 1-7, wherein the outer sheath assembly further comprises an outer retention ring configured to cover the inner retention member, wherein the outer retention ring is attached to the outer sheath assembly with at least one suture.

Embodiment 26: The delivery system of Embodiment Error! Reference source not found., wherein an initial retraction of the outer sheath assembly uncovers the inner retention member from the outer sheath assembly while the outer retention ring remains over the inner retention member, and wherein further proximal retraction of the outer sheath assembly provides tension on the at least one suture to uncover the inner retention member from the outer retention ring.

Embodiment 27: The delivery system of Embodiment 1, wherein the outer sheath assembly comprises a distal section having a plurality of longitudinally spaced apart circumferential rings.

Embodiment 28: The delivery system of Embodiment 1, wherein a distal end of the outer sheath assembly comprises a capsule forming the implant retention area, the capsule having an outer polymer layer, a high melting temperature polymer layer radially inwards of the outer polymer layer, a metal layer radially inwards of the high melting temperature polymer layer, and a liner radially inwards of the metal layer, wherein the high temperature polymer layer comprises a polymer layer having a melting temperature of at least 150° C.

Embodiment 29: The delivery system of Embodiment Error! Reference source not found., wherein the high melting temperature polymer layer comprises PTFE or ePTFE.

Embodiment 30: A delivery system for delivering an expandable implant to a body location, the delivery system comprising an outer sheath assembly comprising an outer shaft having an outer lumen and a proximal end and a distal end, wherein the outer sheath assembly comprises an implant retention area configured to retain the expandable implant in a compressed configuration, an inner assembly located within the outer lumen, the inner assembly comprising an inner shaft having an inner lumen and a proximal end and a distal end, wherein the inner assembly comprises an inner retention member configured to be releasably attached to the expandable implant, a rail assembly located within the inner lumen, the rail assembly comprising a rail shaft having a lumen and a proximal end and a distal end, wherein the rail assembly comprises one or more pull wires attached on an inner surface of the rail configured to provide an axial force on the rail shaft to steer the rail assembly, and a nose cone assembly located within the rail lumen, the nose cone assembly comprising a nose cone shaft having a guide wire lumen and a proximal and distal end.

Embodiment 31: The delivery system of Embodiment Error! Reference source not found., wherein the rail is configured to form two bends, a proximal bend and a distal bend.

Embodiment 32: The delivery system of any one of Embodiments 30-31, wherein the outer shaft comprises a series of slots that rotate around a circumference of the outer shaft from a proximal end to a distal end.

Embodiment 33: The delivery system of any one of Embodiments 30-32, further comprising a proximal pull wire and a distal pull wire, wherein the proximal pull wire attaches to the rail shaft at a location proximal to an attachment point of the distal pull wire.

Embodiment 34: The delivery system of any one of Embodiments 30-33, wherein the outer shaft comprises a braided tube attached onto a slotted hypotube.

Embodiment 35: The delivery system of any one of Embodiments 1-34, wherein the outer shaft comprises a capsule on a distal end of the outer shaft, the capsule comprising over 100 slots along its length and a flarable distal section.

Embodiment 36: The delivery system of any one of Embodiments 30-35, further comprising a handle, wherein the handle is configured to move the outer sheath assembly, inner sheath assembly, and nose cone assembly along the rail assembly.

Embodiment 37: The delivery system of any one of Embodiments 30-36, wherein the inner shaft comprises a plurality of slots on a distal end of the inner shaft.

Embodiment 38: The delivery system of any one of Embodiments 30-37, further comprising the expandable implant, wherein the expandable implant is restrained between the inner retention member and the outer shaft.

Embodiment 39: A delivery system comprising an outer sheath assembly and/or an inner assembly and means for bending of the delivery system to facilitate delivery of an expandable implant to a body location.

Other embodiments of the present disclosure include but are not limited to a delivery system comprising one or more of the features described above or described further below. For example, in one embodiment a delivery system may comprise a capsule having one or more of the features as described herein. In another embodiment, a delivery system may comprise a shaft having one or more of the features described herein. In another embodiment, a delivery system may comprise a steerable outer sheath and collapsible capsule having one or more of the features as described herein. In another embodiment, a delivery system may comprise axial runners having one or more of the features as described herein.

BRIEF DESCRIPTION OF THE DRAWINGS

FIG. 46A illustrates an embodiment of an overmolded inner retention member.

FIG. 46B illustrates an embodiment of a track and pin capsule and inner retention member.

DETAILED DESCRIPTION

The present specification and drawings provide aspects and features of the disclosure in the context of several embodiments of replacement heart valves, delivery systems and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral delivery approach, it should be understood that these embodiments can be used for other delivery approaches such as, for example, transapical approaches. Moreover, it should be understood that certain of the features described in connection with some embodiments can be incorporated with other embodiments, including those which are described in connection with different delivery approaches.

Delivery System

Figure 1:
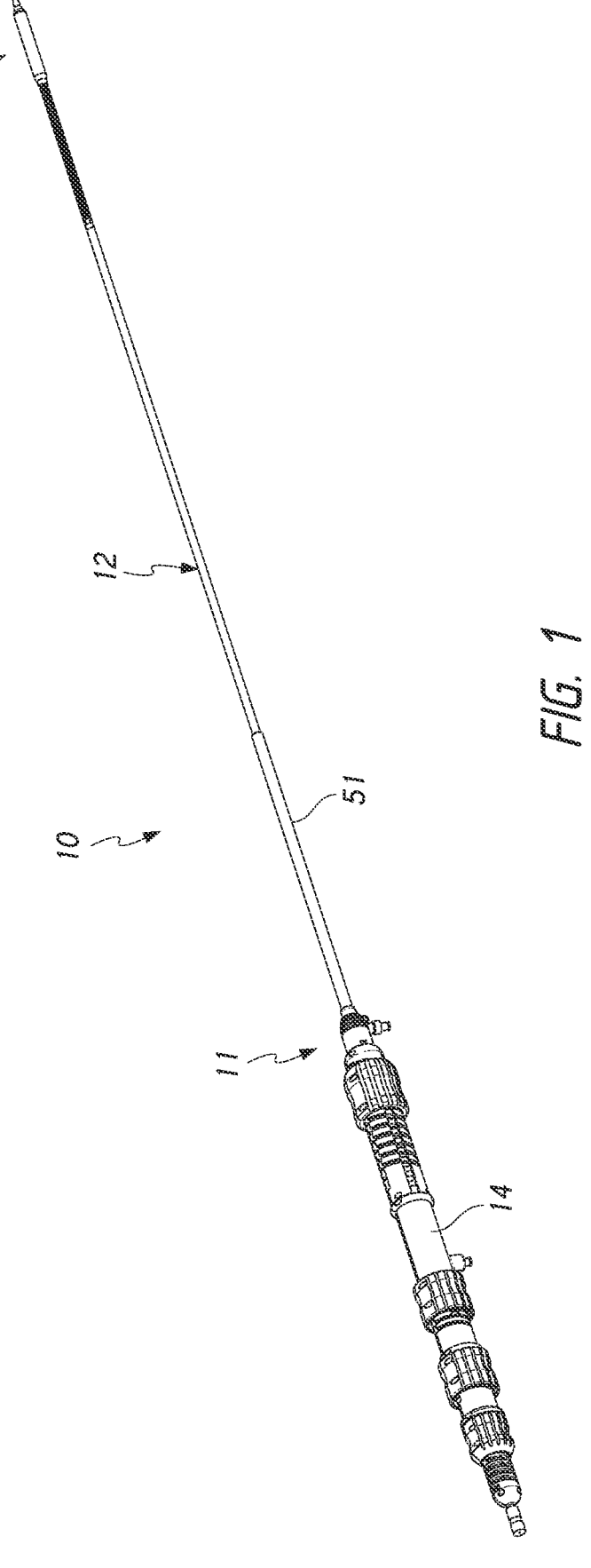
FIG. 1 shows an embodiment of a delivery system.

FIG. 1 illustrates an embodiment of a delivery device, system, or assembly 10. The delivery system can be used deploy a prosthesis, such as a replacement heart valve, within the body. Replacement heart valves can be delivered to a patient's heart mitral valve annulus or other heart valve location in various manners, such as by open surgery, minimally-invasive surgery, and percutaneous or transcatheter delivery through the patient's vasculature. Example transfemoral approaches may be found in U.S. Pat. Pub. No. 2015/0238315, filed Feb. 20, 2015, the entirety of which is hereby incorporated by reference in its entirety. While the delivery system 10 is described in connection with a percutaneous delivery approach, and more specifically a transfemoral delivery approach, it should be understood that features of delivery system 10 can be applied to other delivery system, including delivery systems for a transapical delivery approach.

The delivery system 10 can be used to deploy a prosthesis, such as a replacement heart valve as described elsewhere in this specification, within the body. The delivery system 10 can receive and/or cover portions of the prosthesis such as a first end 301 and second end 303 of the prosthesis 70 illustrated in FIG. 3A below. For example, the delivery system 10 may be used to deliver an expandable implant or prosthesis 70, where the prosthesis 70 includes the first end 301 and the second end 303, and wherein the second 303 end is configured to be deployed or expanded before the first end 301.

Figures 2A, 2B:
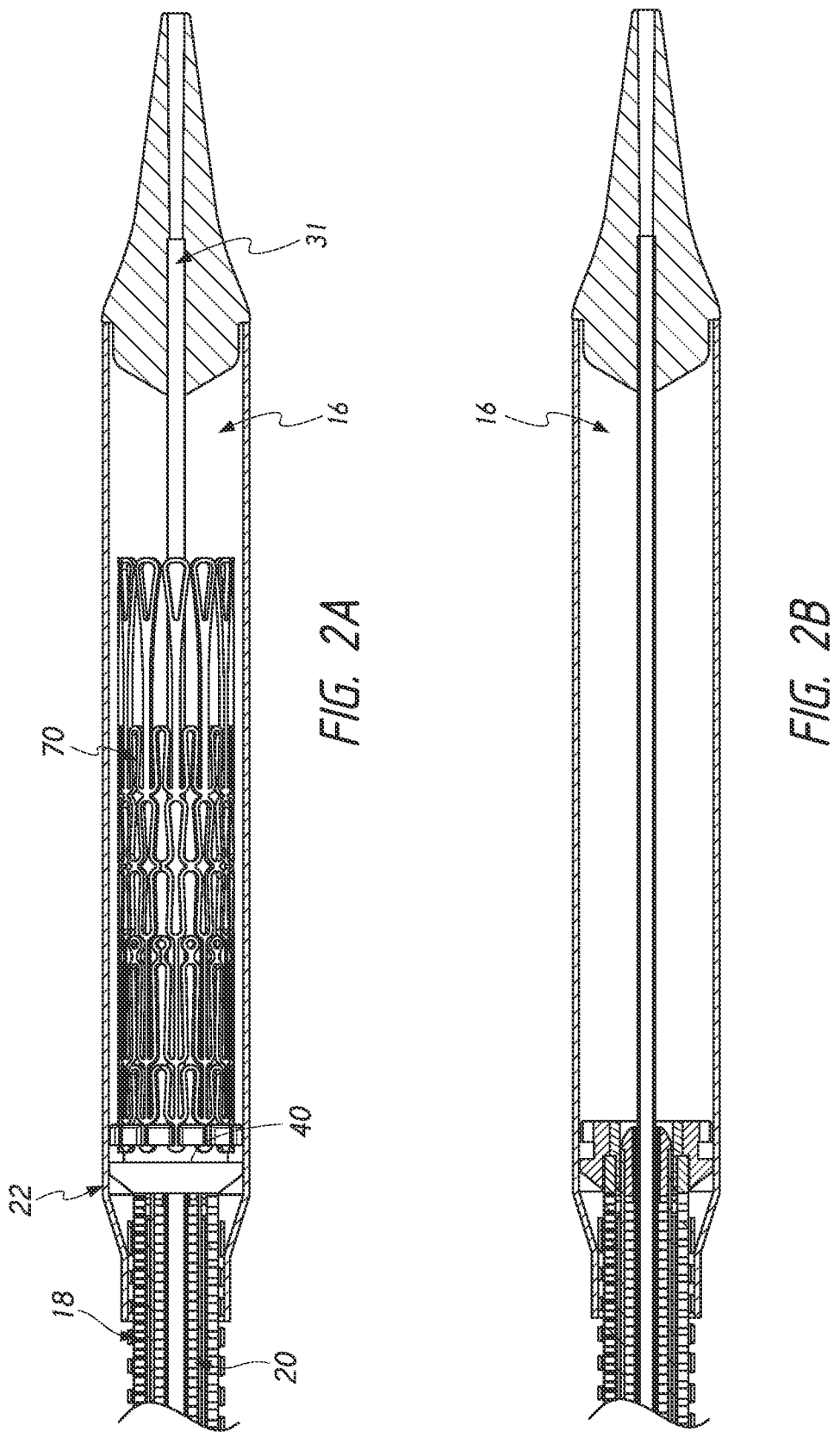
FIG. 2A shows a partial cross-sectional view of the distal end of the delivery system of FIG. 1 loaded with the valve prosthesis of FIG. 3A.
FIG. 2B shows a partial cross-sectional view of the distal end of the delivery system of FIG. 1 without the valve prosthesis of FIG. 3A.
Figure 3A:
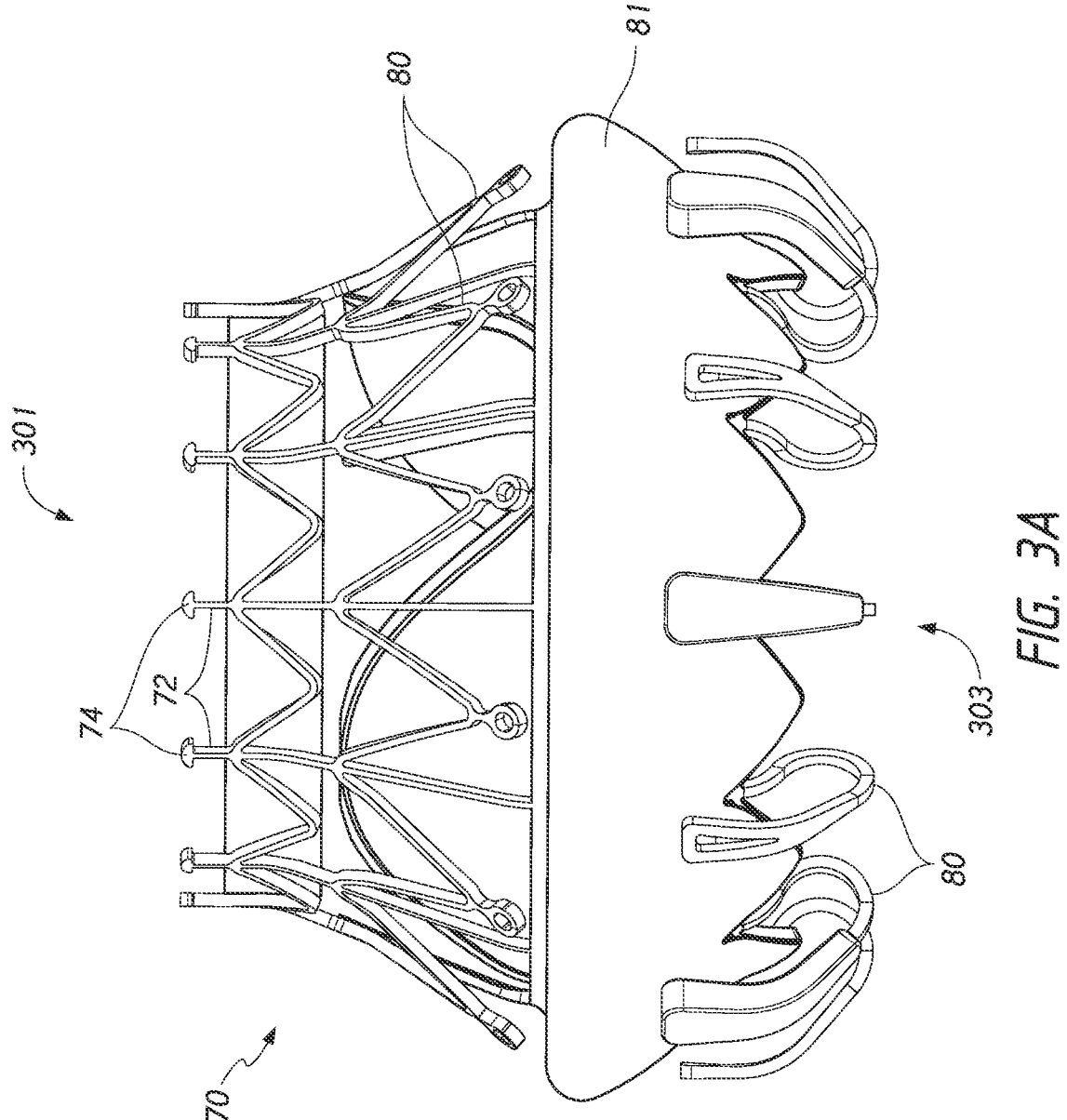
FIG. 3A shows a side view of an embodiment of a valve prosthesis that may be delivered using the delivery systems described herein.

FIG. 2A further shows an example of the prosthesis 70 that can be inserted into the delivery system 10, specifically into the implant retention area 16. For ease of understanding, in FIG. 2A, the prosthesis is shown with only the bare metal frame illustrated. The implant or prosthesis 70 can take any number of different forms. A particular example of frame for a prosthesis is shown in FIG. 3A, though it will be understood that other designs can also be used. The prosthesis 70 can include one or more sets of anchors, such as distal (or ventricular) anchors 80 extending proximally when the prosthesis frame is in an expanded configuration and proximal (or atrial) anchors 82 extending distally when the prosthesis frame is in an expanded configuration. The prosthesis can further include struts 72 which may end in mushroom-shaped tabs 74 at the first end 301. Further discussion can be found in U.S. Patent Pub. No. 2015/0328000, hereby incorporated by reference in its entirety.

Figure 3B:
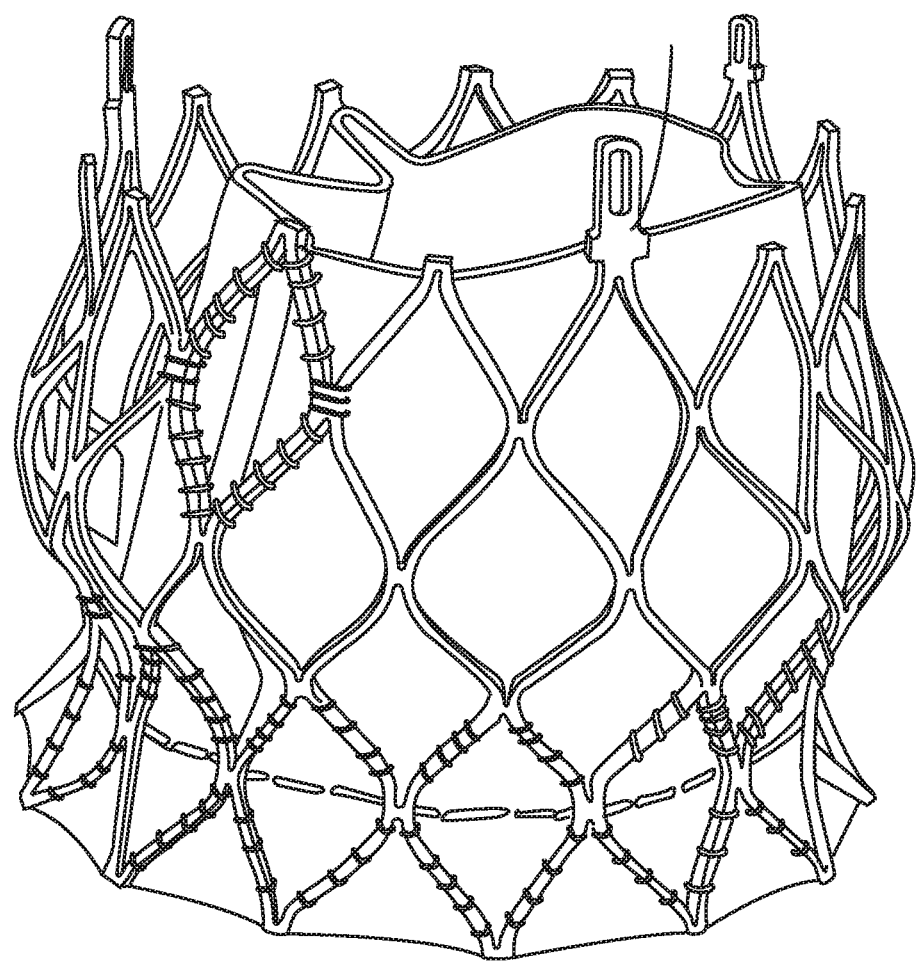
FIG. 3B shows a side view of an embodiment of an aortic valve prosthesis that may be delivered using the delivery systems described herein.

In some embodiments, the delivery system 10 can be used in conjunction with a replacement aortic valve, such as shown in FIG. 3B. In some embodiments the delivery system 10 can be modified to support and delivery the replacement aortic valve. However, the procedures and structures discussed below can similarly be used for a replacement mitral and replacement aortic valve.

Additional details and example designs for a prosthesis are described in U.S. Pat. Nos. 8,403,983, 8,414,644, 8,652, 203 and U.S. Patent Publication Nos. 2011/0313515, 2012/0215303, 2014/0277390, 2014/0277422, 2014/0277427, 2018/0021129, and 2018/0055629, the entirety of these patents and publications are hereby incorporated by reference and made a part of this specification. Further details and embodiments of a replacement heart valve or prosthesis and its method of implantation are described in U.S. Patent Pub. Nos. 2015/0328000 and U.S. Patent Pub. No. 2016/0317301, the entirety of each of which is hereby incorporated by reference and made a part of this specification.

The delivery system 10 can be relatively flexible. In some embodiments, the delivery system 10 is particularly suitable for delivering a replacement heart valve to a mitral valve location through a transseptal approach (e.g., between the right atrium and left atrium via a transseptal puncture).

As shown in FIG. 1, the delivery system 10 can include a shaft assembly 12 comprising a proximal end 11 and a distal end 13, wherein a handle 14 is coupled to the proximal end of the assembly 12. The shaft assembly 12 can be used to hold the prosthesis for advancement of the same through the vasculature to a treatment location. The delivery system 10 can further comprise a relatively rigid live-on sheath 51 surrounding the shaft assembly 12 that can prevent unwanted motion of the shaft assembly 12. The shaft assembly 12 can include an implant retention area 16 (shown in FIGS. 2A-B with FIG. 2A showing the prosthesis 70 and FIG. 2B with the prosthesis 70 removed) at its distal end that can be used for this purpose. In some embodiments, the shaft assembly 12 can hold an expandable prosthesis in a compressed state at implant retention area 16 for advancement of the prosthesis 70 within the body. The shaft assembly 12 may then be used to allow controlled expansion of the prosthesis 70 at the treatment location. The implant retention area 16 is shown in FIGS. 2A-B at the distal end of the delivery system, but may also be at other locations. In some embodiments, the prosthesis 70 may be rotated in the implant retention area 16, such as through the rotation of the inner shaft assembly 18 discussed herein.

As shown in cross-sectional view of FIGS. 2A-B, the distal end of the delivery system 10 can include one or more subassemblies such as an outer sheath assembly 12 inner shaft assembly 18, a rail assembly 20, and nose cone assembly 31 as will be described in more detail below.

In particular, embodiments of the disclosed delivery system can utilize a steerable rail in the rail assembly 20 for steering the distal end of the delivery system 10, allowing the implant to be properly located in a patient's body. As discussed in detail below, the steerable rail can be, for example, a rail shaft that extends through the delivery system 10 from the handle generally to the distal end. A user can manipulate the bending of the distal end of the rail, thereby bending the rail in a particular direction. In preferred embodiments, the rail has more than one bend along its length, thereby providing multiple directions of bending. As the rail is bent, it presses against the other assemblies to bend them as well, and thus the other assemblies of the delivery system 10 can be configured to steer along with the rail as a cooperating single unit, thus providing for full steerability of the distal end of the delivery system. Once the rail is steered into a particular location in a patient's body, the prosthesis 70 can be advanced along the rail and released into the body.

Starting with the outermost assembly, the delivery system can include an outer sheath assembly 22 forming a radially outer covering, or sheath, to surround an implant retention area 16 and prevent the implant from radially expanding. Moving radially inward, the inner shaft assembly 18 can be composed an inner shaft with its distal end attached to inner retention member or inner retention ring 40 for axially retaining the prosthesis. The inner shaft assembly 18 can be located within a lumen of the outer sheath assembly 22. Moving further inwards, the rail assembly 20 can be configured for steerability, as mentioned above and further described below. The rail assembly 20 can be located within a lumen of the inner shaft assembly 18. Further, the most radially-inward assembly is the nose cone assembly 31 which includes the nose cone shaft 27 having its distal end connected to the nose cone 28. The nose cone assembly 31 is preferably located within a lumen of the rail shaft assembly 20. The nose cone assembly 31 can include a lumen for a guide wire to pass therethrough.

The shaft assembly 12, and more specifically the nose cone assembly 31, inner assembly 18, rail assembly 20, and outer sheath assembly 22, can be collectively configured to deliver a prosthesis 70 positioned within the implant retention area 16 (shown in FIG. 2A) to a treatment location. One or more of the subassemblies can then be moved to allow the prosthesis 70 to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis 70 can be controllably loaded onto the delivery system 10 and then later deployed within the body. Further, the handle 14 can provide steering to the rail assembly 20, providing for bending/flexing/steering of the distal end of the delivery system 10.

As will be discussed below, the inner retention member 40 and the outer sheath assembly 22 can cooperate to hold the prosthesis 70 in a compacted configuration. The inner retention member 40 is shown engaging struts 72 at the proximal end 301 of the prosthesis 70 in FIG. 2A. For example, slots located between radially extending teeth on the inner retention member 40 can receive and engage the struts 72 which may end in mushroom-shaped tabs 74 on the proximal end of the prosthesis 70. The outer sheath assembly 22 can be positioned over the inner retention member 40 so that the first end 301 of the prosthesis 70 is trapped there between, securely attaching it to the delivery system 10 between the outer sheath assembly 22 and the inner retention member 40.

As shown in FIG. 2A, the distal anchors 80 can be located in a delivered configuration where the distal anchors 80 point generally distally (as illustrated, axially away from the main body of the prosthesis frame and away from the handle of the delivery system). The distal anchors 80 can be restrained in this delivered configuration by the outer sheath assembly 22. Accordingly, when the outer sheath 22 is withdrawn proximally, the distal anchors 80 can flip positions (e.g., bend approximately 180 degrees) to a deployed configuration (e.g., pointing generally proximally). FIG. 2A also shows the proximal anchors 82 extending distally in their delivered configuration within the outer sheath assembly 22. In other embodiments, the distal anchors 80 can be held to point generally proximally in the delivered configuration and compressed against the body of the prosthesis frame.

The delivery system 10 may be provided to users with a prosthesis 70 preinstalled. In other embodiments, the prosthesis 70 can be loaded onto the delivery system shortly before use, such as by a physician or nurse.

As shown in FIG. 2B, it is not necessary to have an additional layer/shaft/member located between the inner retention member 40 and the outer sheath assembly 22. By eliminating this component, it may be possible to reduce the overall diameter of the delivery system 10.

Figure 2C:
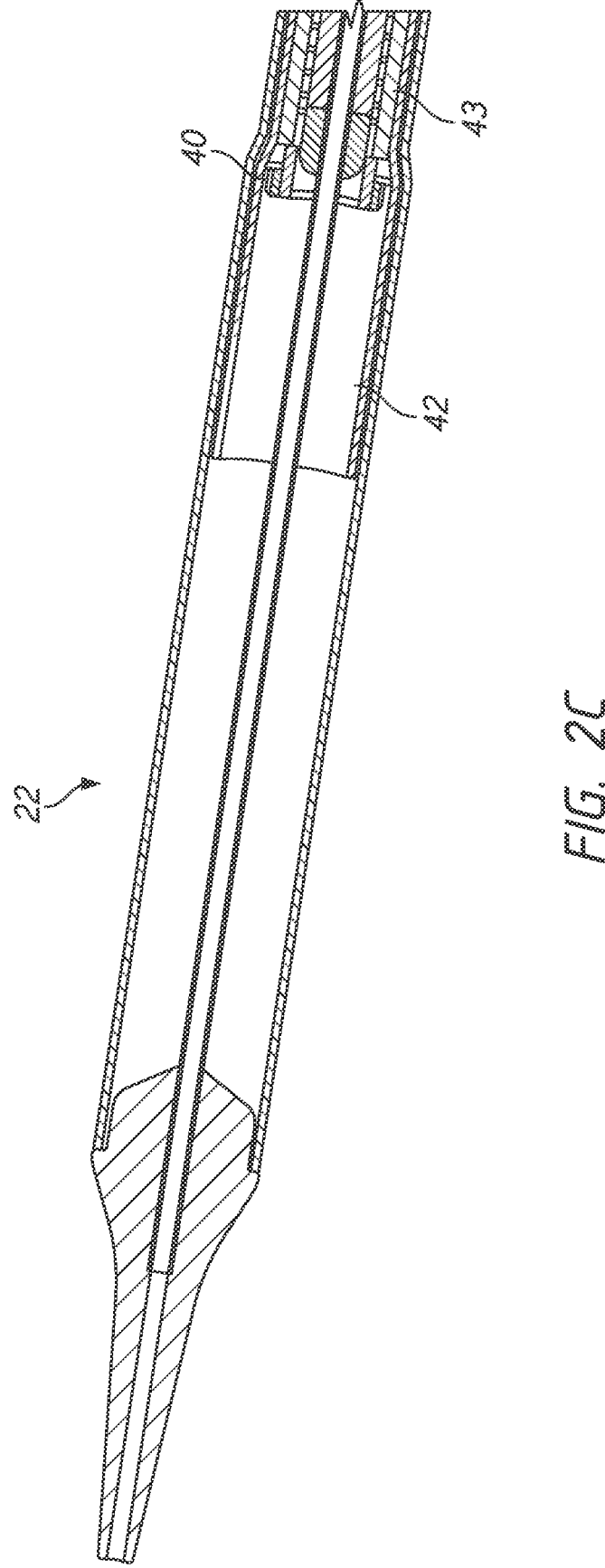
FIG. 2C shows a partial cross-sectional view of the distal end of the delivery system of FIG. 1 without the valve prosthesis of FIG. 3A and including an outer retention ring.

However, in other embodiments, an outer retention member (or ring) 42 may be incorporated into the delivery system 10, as shown in FIG. 2C. The outer retention member 42 may be attached to a mid shaft 43 which can be attached at a proximal end to the handle 14. The outer retention member 42 can advantageously provide further stability to the prosthesis 70 when in the compressed position. The outer retention member 42 can be positioned over the inner retention member 40 so that the first end 301 of the prosthesis 70 is trapped therebetween, which securely attaches it to the delivery system 10.

The outer retention member 42 can encircle a portion of the prosthesis 70, in particular the first end 301, thus preventing the prosthesis 70 from expanding. Further, the mid shaft 43 can be translated proximally with respect to the inner assembly 18 into the outer sheath assembly 22, thus exposing a first end 301 of the prosthesis 70 held within the outer retention member 42. In this way the outer retention member 42 can be used to help secure a prosthesis 70 to or release it from the delivery system 10. The outer retention member 42 can have a cylindrical or elongate tubular shape, and may be referred to as an outer retention ring.

The mid shaft 43 itself can be made of, for example, high density polyethylene (HDPE), as well as other appropriate materials as described herein. The mid shaft 43 can be formed of a longitudinally pre-compressed HDPE tube, which can provide certain benefits. For example, the pre-compressed HDPE tube can apply a force distally onto the outer retention member 42, thus preventing accidental, inadvertent, and/or premature release of the prosthesis 70. Specifically, the distal force by the mid shaft 43 keeps the distal end of the outer retention member 42 distal to the inner retention member 40, thus preventing the outer retention member 42 from moving proximal to the inner retention member 40 before it is desired by a user to release the prosthesis 70. This can remain true even when the delivery system 10 is bent/deflected at a sharp angle. Further disclosure for the outer retention member 42 and mid shaft 43 can be found in U.S. Pat. Pub. No. 2016/0317301, hereby incorporated by reference in its entirety.

Delivery System Assemblies

Figure 4:
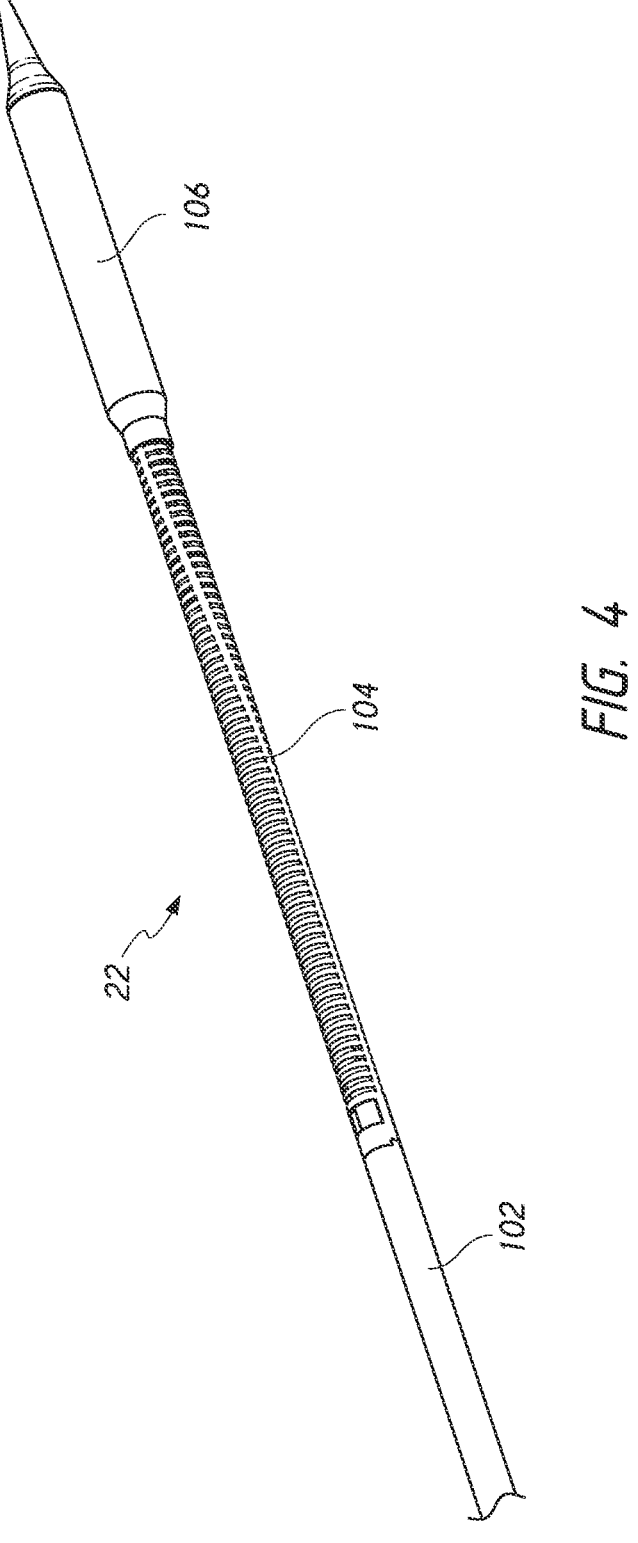
FIG. 4 shows a perspective view of the distal end of the delivery system of FIG. 1.
Figure 5:
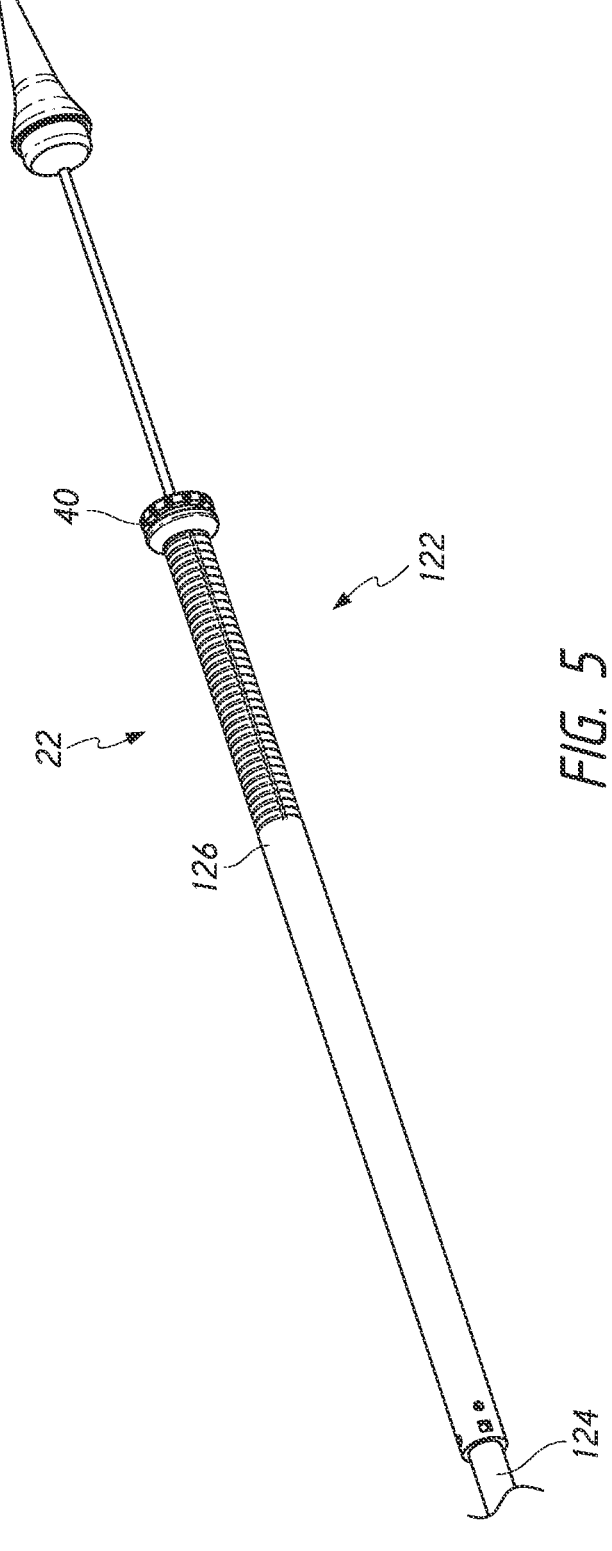
FIG. 5 show components of the delivery system of FIG. 4 with the outer sheath assembly moved proximally and out of view.
Figure 6:
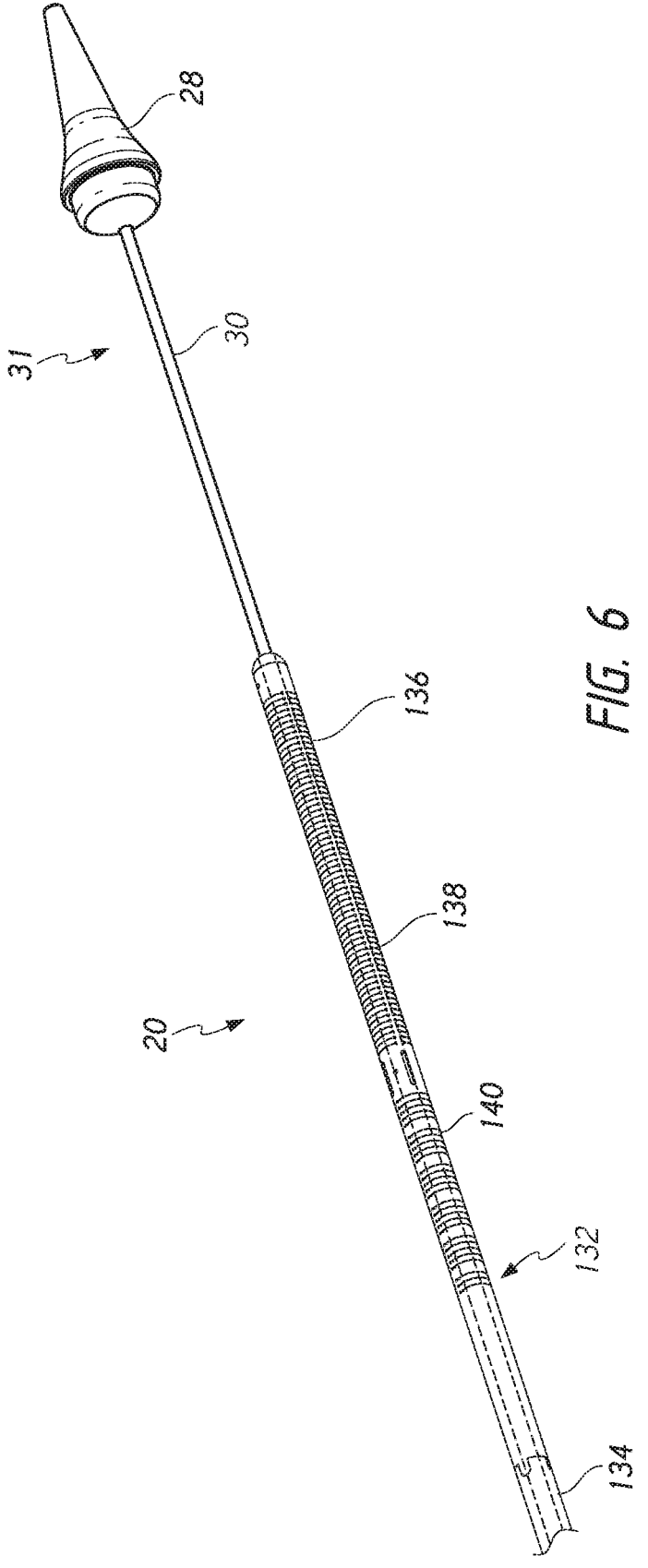
FIG. 6 show components of the delivery system of FIG. 5 with the inner assembly moved proximally and out of view.

FIGS. 4-6 illustrate further views of delivery system 10 with different assemblies translated proximally and described in detail.

Starting with the outermost assembly shown in FIG. 4, the outer sheath assembly 22 can include an outer proximal shaft 102 directly attached to the handle 14 at its proximal end and an outer hypotube 104 attached at its distal end. A capsule 106 can then be attached generally at the distal end of the outer hypotube 104. These components of the outer sheath assembly 22 can form a lumen for the other subassemblies to pass through.

The outer proximal shaft 102 may be a tube and is preferably formed of a plastic, but could also be a metal hypotube or other material. The outer hypotube 104 can be a metal hypotube which in some embodiments may be cut or have slots, as discussed in detail below. The outer hypotube 104 can be covered or encapsulated with a layer of ePTFE, PTFE, or other material so that the outer surface of the outer hypotube 104 is generally smooth.

The capsule 106 can be a tube formed of a plastic or metal material. In some embodiments, the capsule 106 is formed of ePTFE or PTFE. In some embodiments, this capsule 106 is relatively thick to prevent tearing and to help maintain a self-expanding implant in a compacted configuration. In some embodiments, the material of the capsule 106 is the same material as the coating on the outer hypotube 104. As shown, the capsule 106 can have a diameter larger than the outer hypotube 104, though in some embodiments the capsule 106 may have a similar diameter as the hypotube 104. The capsule 106 can be configured to retain the prosthesis 70 in the compressed position within the capsule 106.

The outer sheath assembly 22 is configured to be slidable over the inner assembly 18, the rail assembly 20, and the nose cone assembly 31.

Moving radially inwardly, the next assembly is the inner shaft assembly 18. FIG. 5 shows a similar view as FIG. 4, but with the outer sheath assembly 22 removed, thereby exposing the inner shaft assembly 18. As may be noted, there is no additional outer retention mechanism or shaft, such as an outer retention ring, between the inner shaft assembly 18 and the outer sheath assembly 22.

The inner shaft assembly 18 can include an inner shaft 122 generally attached at its proximal end to the handle 14, and an inner retention ring 40 located at the distal end of the inner shaft 122. The inner shaft 122 itself can include an inner proximal shaft 124 directly attached to the handle 14 at a proximal end and an inner hypotube 126 attached to the distal end of the inner proximal shaft 124. Thus, the inner retention ring 40 can be attached generally at the distal end of the inner hypotube 126. These components of the inner shaft assembly 18 can form a lumen for the other subassemblies to pass through.

Similar to the other assemblies, the inner proximal shaft 124 can comprise a tube, such as a hypodermic tube or hypotube (not shown). The tube can be made from one of any number of different materials including nitinol, cobalt chromium, stainless steel, and/or medical grade plastics. The tube can be a single piece tube or multiple pieces connected together. A tube comprising multiple pieces can provide different characteristics along different sections of the tube, such as rigidity and flexibility. The inner hypotube 126 can be a metal hypotube, which in some embodiments may be cut or have slots as discussed in detail below. The tube 126 can be covered or encapsulated with a layer of ePTFE, PTFE, or other material so that the outer surface of the inner hypotube 126 is generally smooth.

The inner retention member 40 can be configured as a prosthesis retention mechanism that can be used to engage with the prosthesis, as discussed with respect to FIG. 2A. For example, the inner retention member 40 may be a ring and can include a plurality of slots configured to engage with struts 72 on the prosthesis 70. The inner retention member 40 can also be considered to be part of the implant retention area 16, and may be at the proximal end of the implant retention area 16. With struts or other parts of a prosthesis 70 engaged with the inner retention member 40, the capsule can cover both the prosthesis and the inner retention member 40 to secure the prosthesis on the delivery system 10. Thus, the prosthesis 70 can be sandwiched between the inner retention member 40 of the inner shaft assembly 18 and the capsule 106 of the outer sheath assembly 22.

The inner shaft assembly 18 is disposed so as to be slidable over the rail assembly 20 and the nose cone assembly 31.

Next, radially inwardly of the inner shaft assembly 18 is the rail assembly 20 as shown in FIG. 6. The rail assembly can include a rail shaft 132 (or rail) generally attached at its proximal end to the handle 14. The rail shaft 132 can be made up of a rail proximal shaft 134 directly attached to the handle at a proximal end and a rail hypotube 136 attached to the distal end of the rail proximal shaft 134. The rail hypotube 136 can further include an atraumatic rail tip at its distal end. These components of the rail shaft assembly 20 can form a lumen for the other subassemblies to pass through.

Attached to an inner surface of the rail hypotube 136 are one or more pull wires which can be used apply forces to the rail hypotube 136 and steer the rail assembly 20. The pull wires can extend distally from the knobs in the handle 14, discussed below, to the rail hypotube 136. As noted above, pull wires can be attached at different longitudinal locations along the rail hypotube 136, thus providing for multiple bending regions in the rail hypotube 136, thereby allowing for multidimensional steering.

In some embodiments, two distal pull wires 138 can extend to a distal section of the rail hypotube 136 and two proximal pull wires 140 can extend to a proximal section of the rail hypotube 136. However, other numbers of pull wires can be used and the particular number of pull wires is not limiting. For example, a single pull wire can extend to a distal location and a single pull wire can extend to a proximal location. In some embodiments, ring-like structures attached inside the rail hypotube 136, known as pull wire connectors, may be provided as attachment locations for the pull wires. In some embodiments, the rail assembly 20 can include a distal pull wire connector and a proximal pull wire connector. In some embodiments, the pull wires can directly connect to an inner surface of the rail hypotube 136.

The distal pull wires 138 can be connected (either on its own or through a connector) generally at the distal end of the rail hypotube 136. The proximal pull wires 140 can connect (either on its own or through a connector) at a location approximately one quarter, one third, or one half of the length up the rail hypotube 136 from the proximal end. In some embodiments, the distal pull wires 138 can pass through small diameter pull wire lumens attached on the inside of the rail hypotube 136. This can prevent the wires 138 from pulling on the rail hypotube 136 at a location proximal to the distal connection. In some embodiments, these lumens can be attached to an outer surface of the nose cone shaft 31 distal to a location at which the proximal pull wires 140 attach to the rail hypotube 136.

For the pair of proximal pull wires 140, the wires can be spaced approximately 180 degrees from one another to allow for steering in opposite directions. Similarly, for pair of distal pull wires 138, the wires can be spaced approximately 180 degrees from one another to allow for steering in both directions. In some embodiments, the pair of distal pull wires 138 and the pair of proximal pull wires 140 can be spaced approximately 90 degrees from each other. In some embodiments, the pair of distal pull wires 138 and the pair of proximal pull wires 140 can be spaced approximately 0 degrees from each other. However, other locations for the pull wires can be used as well, and the particular location of the pull wires is not limiting.

The rail assembly 20 is disposed so as to be slidable over the nose cone assembly 31.

Moving further inwardly from the rail assembly is the nose cone assembly 31 also seen in FIG. 6. This may be a nose cone shaft 27, and in some embodiments, may have a nose cone 28 on its distal end. The nose cone 28 can be made of polyurethane for atraumatic entry and to minimize injury to surrounding vasculature. The nose cone 28 can also be radiopaque to provide for visibility under fluoroscopy.

The nose cone shaft 27 may include a lumen sized and configured to slidably accommodate a guide wire so that the delivery system 10 can be advanced over the guide wire through the vasculature. However, embodiments of the system 10 discussed herein may be constructed for use without a guide wire and thus the nose cone shaft 27 can be solid. The nose cone shaft 27 may be connected from the nose cone 28 to the handle, or may be formed of different segments such as the other assemblies. Further, the nose cone shaft 27 can be formed of different materials, such as plastic or metal, similar to those described in detail above.

One or more spacer sleeves (not shown) can be used between different assemblies of the delivery system 10. For example, a first spacer sleeve can be located concentrically between the inner shaft assembly 18 and the rail assembly 20, generally between the inner and rail hypotubes 126/136. A second spacer sleeve can be located concentrically between the rail assembly 20 and the nose cone assembly 30, generally longitudinally within the rail hypotube 136. In some embodiments, only one spacer sleeve may be used (either the first spacer sleeve or the second spacer sleeve). In other embodiments, both spacer sleeves can be used. However, in further embodiments no spacer sleeves are used. The spacer sleeve can be made of a polymer material such as braided Pebax® and can be lined, for example with PTFE, on the inner diameter, though the particular material is not limiting. The spacer sleeve can advantageously reduce friction between the steerable rail assembly 20 and its surrounding assemblies. Thus, the spacer sleeves can act as a buffer between the rail assembly 20 and the inner/nose cone assembly 18/30. Further, the spacer sleeve can take up any gap in radius between the assemblies, preventing compressing or snaking of the assemblies during steering.

The spacer sleeve can be mechanically contained by the other lumens and components, and is thus not physically attached to any of the other components, allowing the spacer sleeve to be "floating" in that area. The floating aspect of the spacer sleeve allows it to move where needed during deflection and provide a support and/or lubricious bear surface/surfaces. Accordingly, the floating aspect allows the delivery system 10 to maintain flex forces. However, in some embodiments, the spacer sleeve can be connected to other components.

Hypotube Construction

As discussed above, the outer sheath assembly 22, the inner assembly 18, and the rail assembly 20 can contain an outer hypotube 104, an inner hypotube 126, and a rail hypotube 136, respectively. Each of these hypotubes can be laser cut to include a number of circumferential (i.e., transverse) slots, thereby creating a bending pathway for the delivery system to follow. While different slot assemblies are discussed below, it will be understood that any of the three hypotubes can have any of the slot configurations discussed below. FIGS. 7-15 show the different hypotubes in isolated format.

Figure 7:
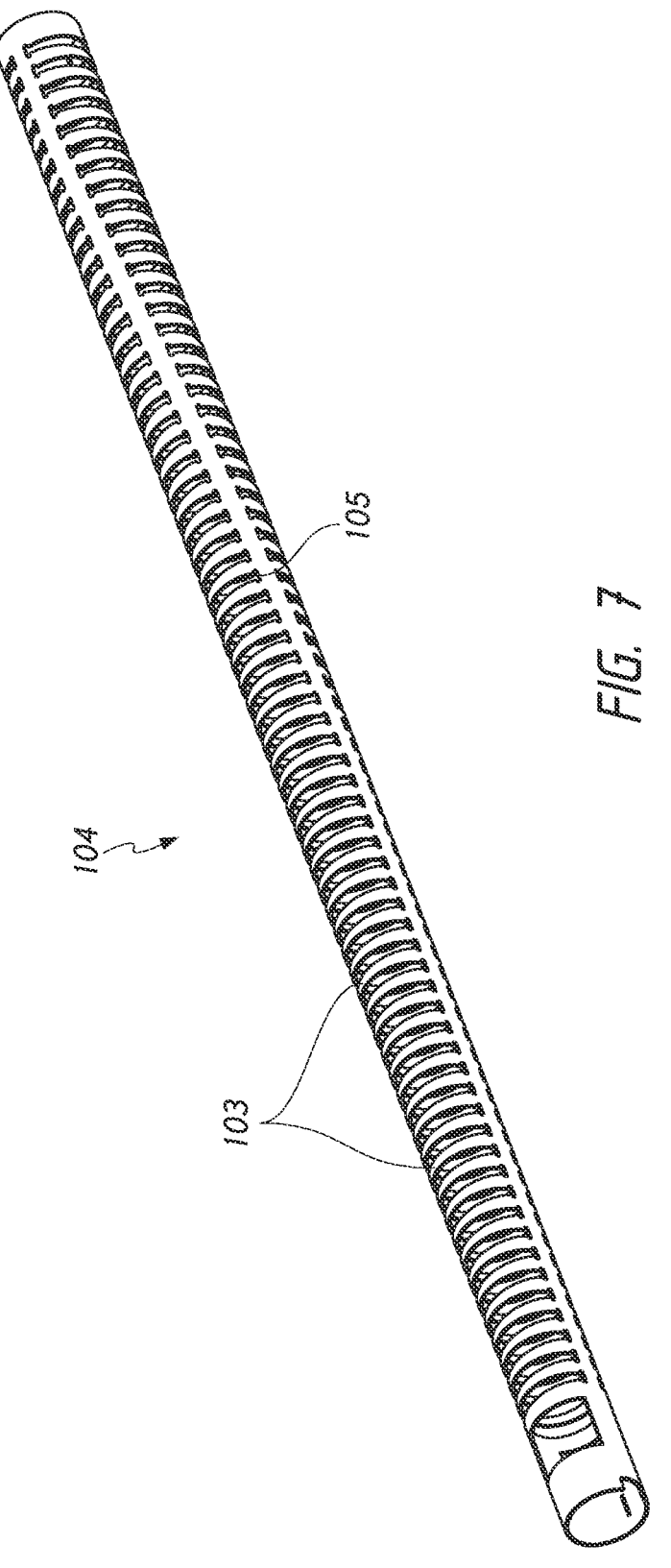
FIG. 7 illustrates an embodiment of an outer hypotube.

The outer hypotube 104, shown in FIG. 7 (distal end towards the right), can include a number slots 103 transverse to its lumen axis along most of the length of the outer hypotube 104. Each of the slots can extend partially or almost entirely around the circumference of the outer hypotube 104, thereby forming a single spine 105 of material extending between the proximal and distal ends of the outer hypotube 104. In some embodiments, the outer hypotube 104 can contain more than one spine, such as two, three, or four spines. As shown, the slots can extend generally from the proximal end of the outer hypotube 104 to the distal end of the hypotube 104, allowing the entirety of the outer hypotube 104 to more easily bend with the rail assembly 20.

As shown, the slot locations may be staggered such that the spine 105 circumferentially rotates while progressing from the proximal end to the distal end of the outer hypotube 104. For example, the distal end of the spine 105 can be approximately 30°, 45°, 90°, 135°, or 180° offset from the proximal end of the spine 105. In some embodiments, the spine 105 remains in the same circumferential location from the proximal end to approximately halfway the length of the outer hypotube 104. At this point, the spine 105 can begin to circumferentially turn around the outer hypotube 104. The curve of the spine helps direct the outer hypotube 105 during steering of the rail assembly 20. The spine 105 generally follows the typical bend formed by the rail assembly 20 when entering the heart and directing towards the mitral valve, thus relieving some of the forces that may occur if the spine 105 was straight. However, in some embodiments the spine 105 of the outer hypotube 104 may be straight, and the particular configuration of the spine is not limiting.

Figure 8:
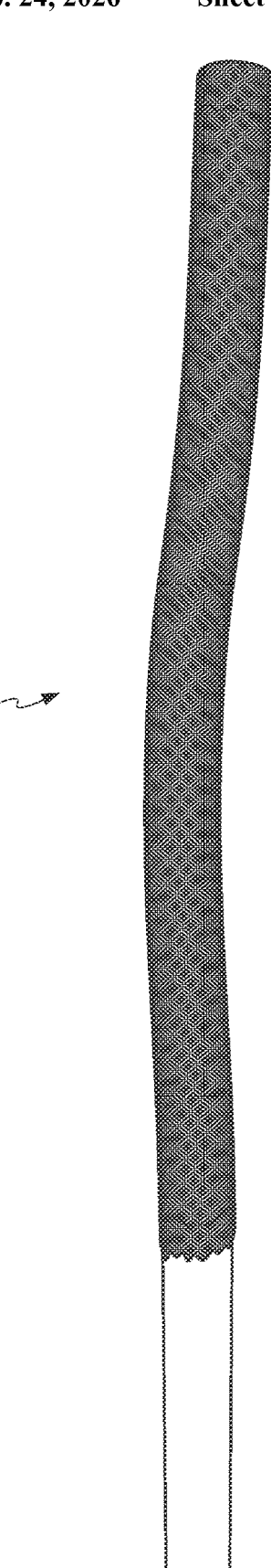
FIGS. 8-13 illustrate an embodiment of a combination laser-cut and braid outer hypotube.
Figure 9:
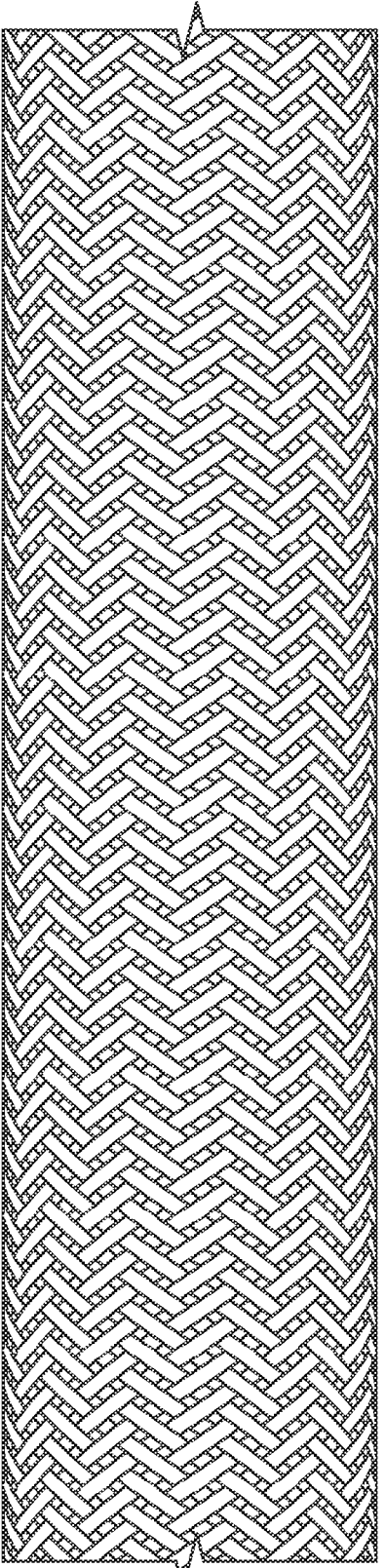
Figure 10:
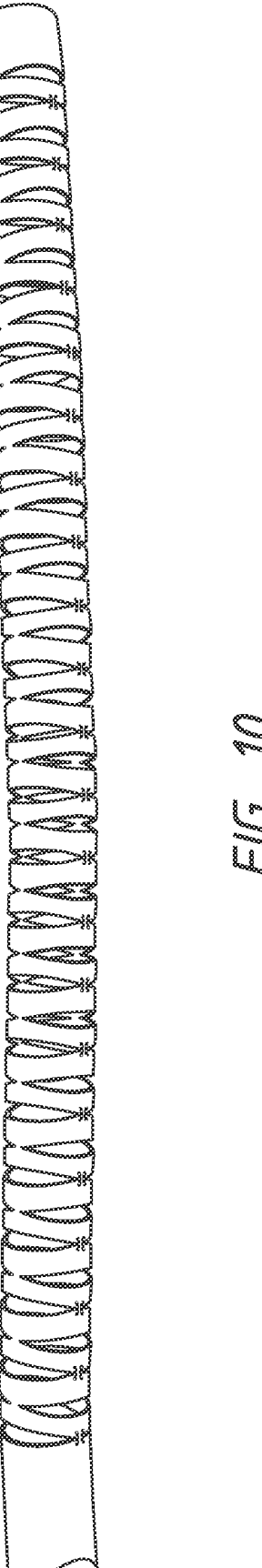

FIGS. 8-13 illustrate another embodiment of the outer hypotube 104 (distal end towards the right for FIGS. 8-10). In a typical hypotube, there is a need to choose between the number of planes of flexibility and compressive/tensile strength. In contrast to conventional hypotube designs, embodiments are disclosed herein wherein a hybrid material may accomplish universal flexibility with high compressive/tensile strength. In particular, a combination of a braid and a lasercut can be used to overcome shortcomings of earlier hypotube designs. The braided material (e.g., tube, hypotube, cover, jacket) can be a plurality of interlaced materials. The interlaced materials can be strands of material, such as strands of flexible material. The braid can be formed of metal, plastic, polymer, ceramic, etc. and the particular material does not limit the disclosure.

Braided materials, such as the braided tube 1100 shown in FIG. 9 can be advantageous in tension, but they can significantly neck when subjected to high of tension, and are unsatisfactory in compression. On the other hand, slotted (or lasercut) hypotubes, such as the slotted hypotube 1102 shown in FIG. 10 or above in FIG. 7, can be excellent for use in compression and may not neck down when elongated. However, slotted hypotubes have limited strength under tension. Accordingly, it can be advantageous to use a combination of a braided material in conjunction with a lasercut hypotube, thereby advantageously providing both tension and compression benefits. For example, the braided tube can be attached to the lasercut hypotube at one or more of the proximal and distal ends, such as through mechanical or chemical attachment means. In some embodiments, the braided tube 1100 can be located radially outward or radially inwardly of the lasercut hypotube 1102. Further, the use of the braided tube 1100 allows for the hypotube 1102 to have an alternating cut pattern as shown in FIG. 10. The alternating cut pattern allows the lasercut hypotube to bend in all directions, which allows for "universal bending". However, other cut patterns, such as disclosed herein, can be used as well.

Figure 11:
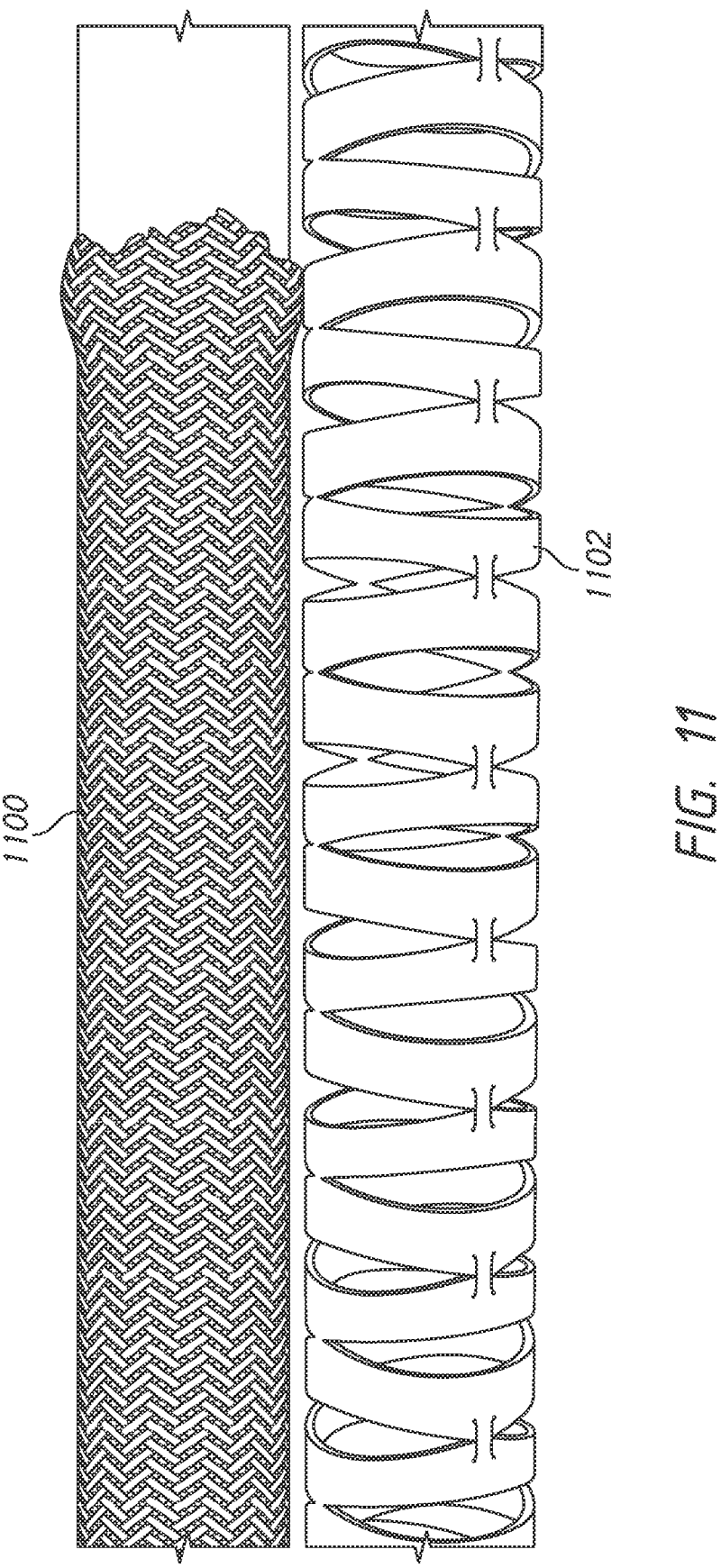

By locating a braided tube 1100 radially on top of a lasercut hypotube 1102, shown side by side in FIG. 11, the braided tube 1100 can lock onto the lasercut hypotube 1102 when pulled (e.g., when put under a tension force). The hypotube 1102 can essential act as a set diameter, thereby preventing the braided tube 1100 from necking down and increasing its ability to transmit tensile forces. This can make the tensile response and strength extremely favorable, and the lasercut hypotube 1102 can provide compression strength. In some embodiments, a coil could be used instead of a lasercut hypotube 1102, and the hypotube can be any number of slotted tubes/configurations with advantageous compression properties.

Figure 12:
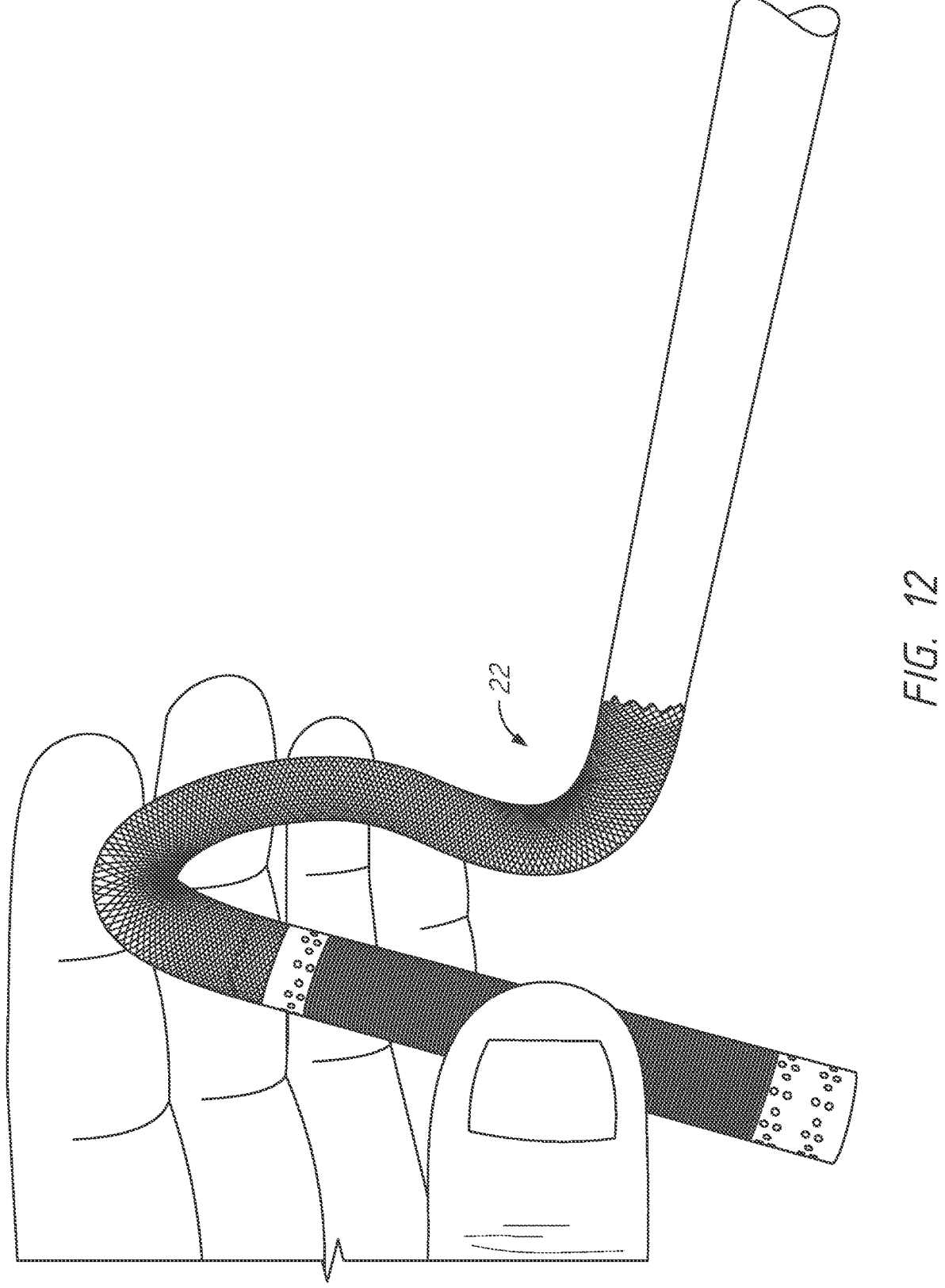
Figure 13:
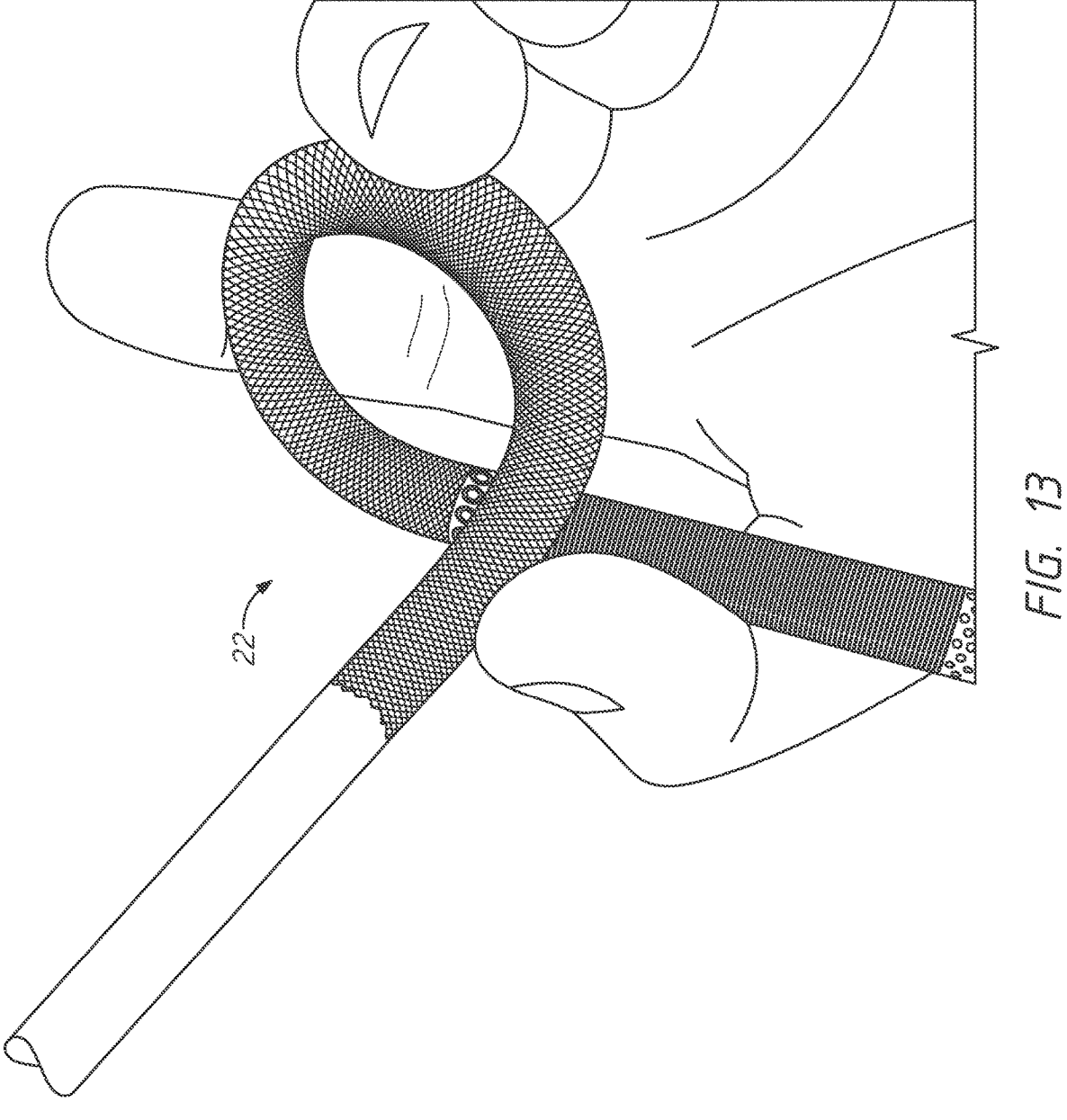

Thus, extremely tight bends/curve can be achieved by the combination of braided material and lasercut hypotubes due to the advantageous tension and compression properties. FIGS. 12-13 illustrate the advantageous bending qualities of the capsule. In some embodiments, a portion of the outer sheath assembly 22 can be formed from the combination braided tube and lasercut hypotube 1102. In some embodiments, all of the outer sheath assembly 22 can be formed from the combination braided tube and lasercut hypotube 1102. In some embodiments, a portion of the outer sheath assembly 22 directly proximal of the capsule 106 can be formed from the combination braided tube and lasercut hypotube 1102.

Figure 14:
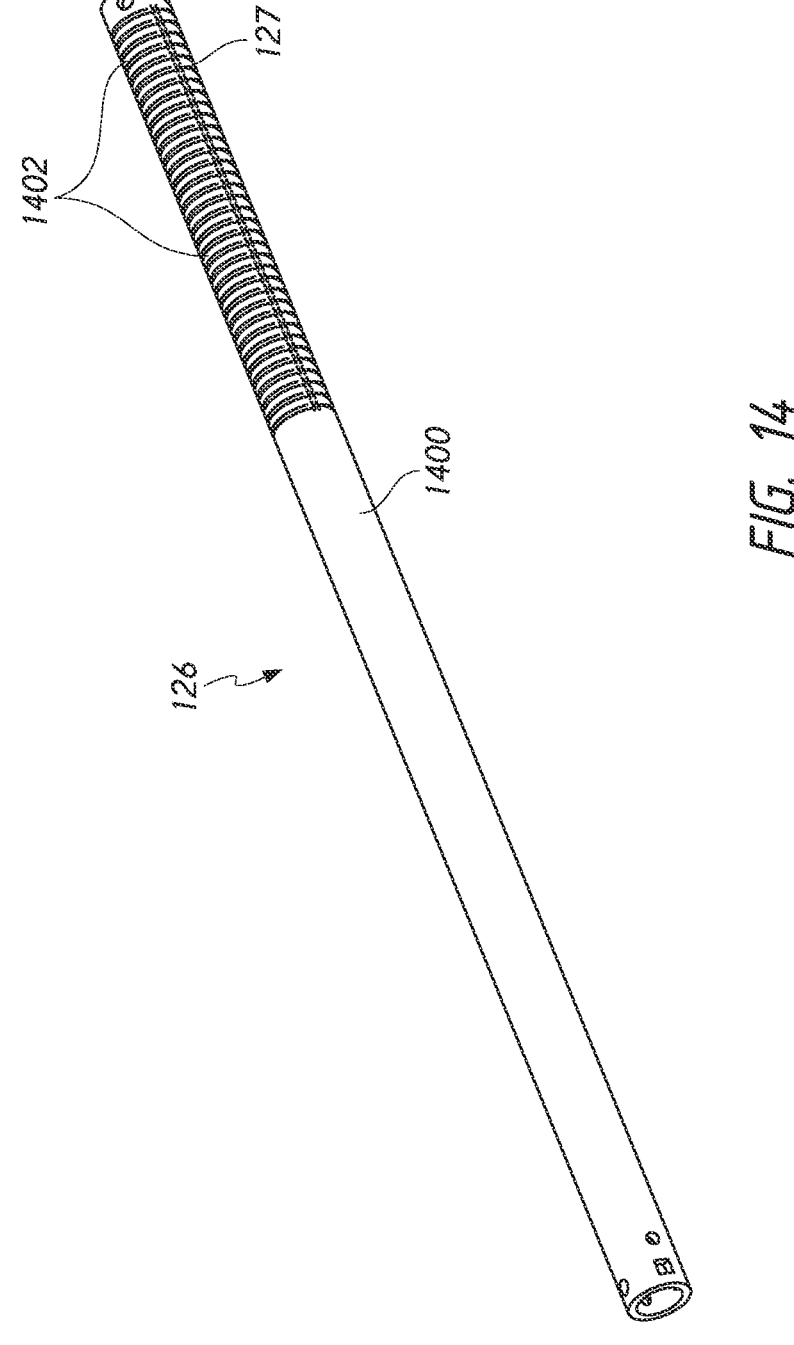
FIG. 14 illustrates an embodiment of an inner hypotube.

Moving radially inwardly in FIG. 14, the inner hypotube 126 also contains a number of slots 1402 (distal end towards the right). However, unlike the outer hypotube 104, the inner hypotube 126 in some embodiments does not contain slots along a majority of its length to form an unslotted portion 1400, although it may contain slots in some iterations. This allows the inner hypotube 126 to be more rigid as the inner hypotube 126 can experience high compressive loads and the enhanced rigidity of the spiral spine prevents coiling.

Further, it allows the inner assembly 18 to direct the other assemblies to extend straight when advanced over the rail assembly 20, as discussed below.

The inner hypotube 126 can contain slots 1402 transverse to its luminal axis along the distal ¼, ⅓, or ½ of its length starting generally from the distal end. In some embodiments, each circumferential position location can have two slots spanning less than 180 degrees, thereby forming two spines 127 in the inner hypotube, unlike the single spine of the outer hypotube 104. These spines 127 can be spaced approximately 180 degrees apart, though in some embodiments different angles can be used depending on the desired bend. However, in some embodiments a single spine or more than two spines can be used. The additional spines can provide additional rigidity to the inner assembly 18.

The inner hypotube 126 can contain a single slot pattern 1402 forming the dual spines as discussed above. In some embodiments, the inner hypotube 126 can contain two different slot patterns. For example, at the distalmost end the slots may be configured for only one direction of bend (for example, only along an X axis), making this section strong and robust but less flexible. However, slots in section proximal can be configured to includes multiple bending axis (for example, along both X and Y axes), thus providing the inner hypotube 126 with more flexibility for steering. In some embodiments, the configuration of the inner hypotube 126 creates forces that tend to straighten (e.g., not bend). Thus, when the inner hypotube 126 is advanced over the rail hypotube 136, it will achieve a generally straight configuration.

Figure 15:
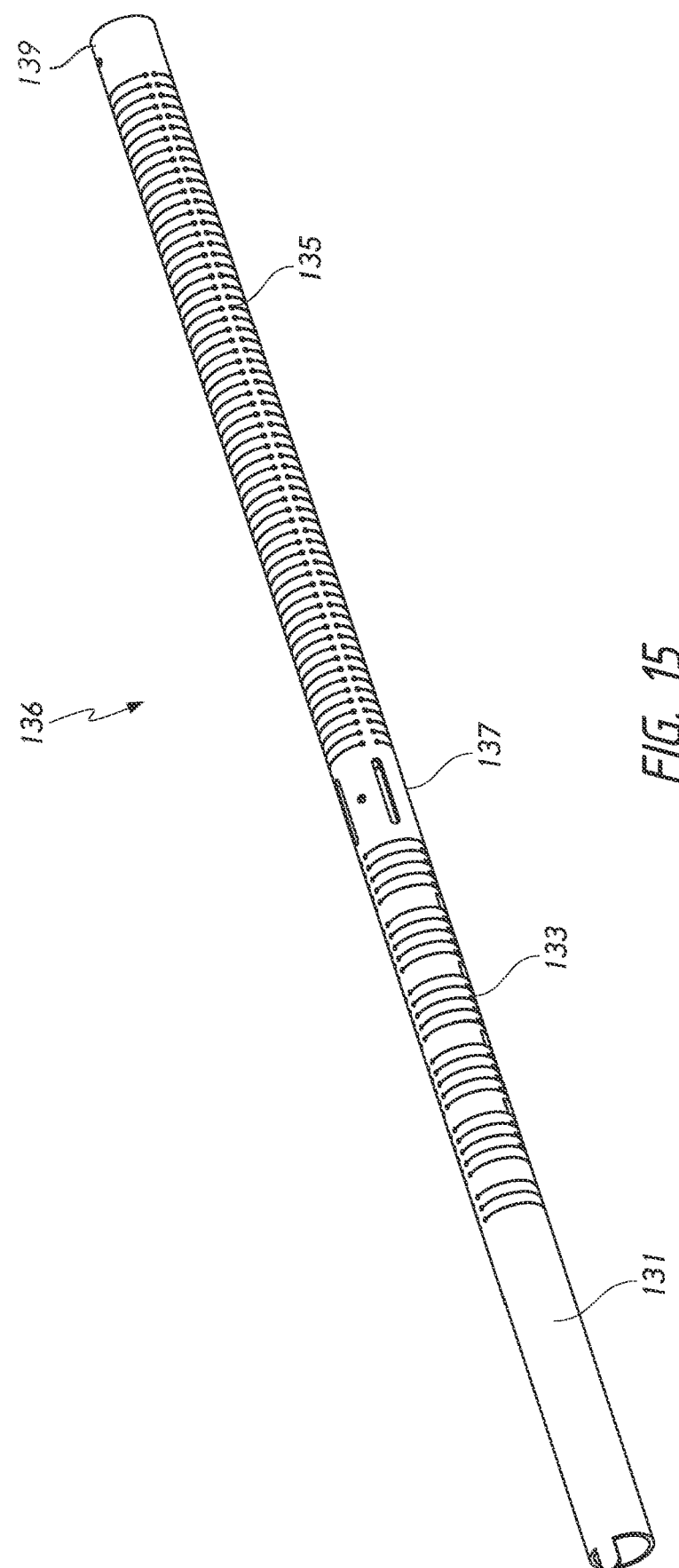
FIG. 15 illustrates an embodiment of a rail hypotube.

Next, again moving radially inwardly, FIG. 15 illustrates an embodiment of the rail hypotube 136 (distal end towards the right). The rail hypotube 136 can also contain a number of transverse slots. The rail hypotube 136 can generally be broken into a number of different sections. At the most proximal end is an uncut (or unslotted) hypotube section 131. This can take up approximately one quarter to one third of the rail hypotube 136. Moving distally, the next section is the proximal slotted hypotube section 133. This section includes a number of transverse slots cut into the rail hypotube. Generally, two slots are cut around each circumferential location forming almost half of the circumference. Accordingly, two backbones are formed between the slots extending up the length of the hypotube 136. This is the section that can be guided by the proximal pull wires 140. Moving further distally is the location 137 where the proximal pull wires 140 connect, and thus slots can be avoided. This section 137 is just distal of the proximally slotted section 133.

Distally following the proximal pull wire connection area is the distal slotted hypotube section 135. This section is similar to the proximal slotted hypotube section 133 but has significantly more slots formed along an equivalent length. Thus, the distally slotted hypotube section 135 provides easier bending than the proximally slotted hypotube section 133. The proximal slotted section 133 can be configured to experience a bend of approximately 90 degrees with a half inch radius whereas the distal slotted section 135 can bend at approximately 180 degrees within a half inch. Further, as shown in FIG. 15, the spines of the distally slotted hypotube section 135 are offset from the spines of the proximally slotted hypotube section 133. Accordingly, the two sections will achieve different bend patterns, allowing for three-dimensional steering of the rail assembly 20. In some embodiments, the spines can be offset by approximately 30, 45, or 90 degrees, although the particular offset is not limiting.

At the distalmost end of the distal slotted hypotube section 135 is the distal pull wire connection area 139 which is again a non-slotted section of the rail hypotube 136.

Capsule Construction

The capsule 106 can be formed from one or more materials, such as PTFE, ePTFE, PEBAX, ULTEM, PEEK, urethane, nitinol, stainless steel, and/or any other biocompatible material. Preferably, the capsule 106 is formed from one or more materials. Preferably, the capsule 106 is compliant and flexible while still maintaining a sufficient degree of radial strength to maintain a replacement valve within the capsule 106 without substantial radial deformation, which could increase friction between the capsule 106 and a replacement valve 70 contained therein. The capsule 106 also preferably has sufficient column strength to resist buckling of the capsule, and sufficient tear resistance to reduce or eliminate the possibility of the replacement valve tearing the capsule 106. Flexibility of the capsule 106 can be advantageous, particularly for a transseptal approach. For example, while being retracted along a curved member, the capsule 106 can flex to follow the curved member without applying significant forces upon the curved member, which may cause the curved member to decrease in radius. More specifically, the capsule 106 can bend and/or kink as it is being retracted along such a curved member such that the radius of the curved member is substantially unaffected.

FIGS. 16-21 show embodiments of a capsule 106 that can be used with embodiments of the delivery system 10. The capsule 106 may include any of the materials and properties discussed above. With many implant capsules, compression resistance and flexibility are typically balanced together, as improved flexibility can lead to worse compression resistance. Thus, there tends to be a choice made between compression resistance and flexibility. However, disclosed are embodiments of a capsule that can achieve both high compression resistance as well as high flexibility.

In particular, a metal hypotube can provide radial strength and compression resistance, while specific slots/cuts in the hypotube can enable the flexibility of the capsule 106. In some embodiments, a thin liner and a jacket can surround the capsule 106, such as a polymer or elastomer layer, to prevent any negative interactions between the implant 70 and the capsule 106.

Figure 16:
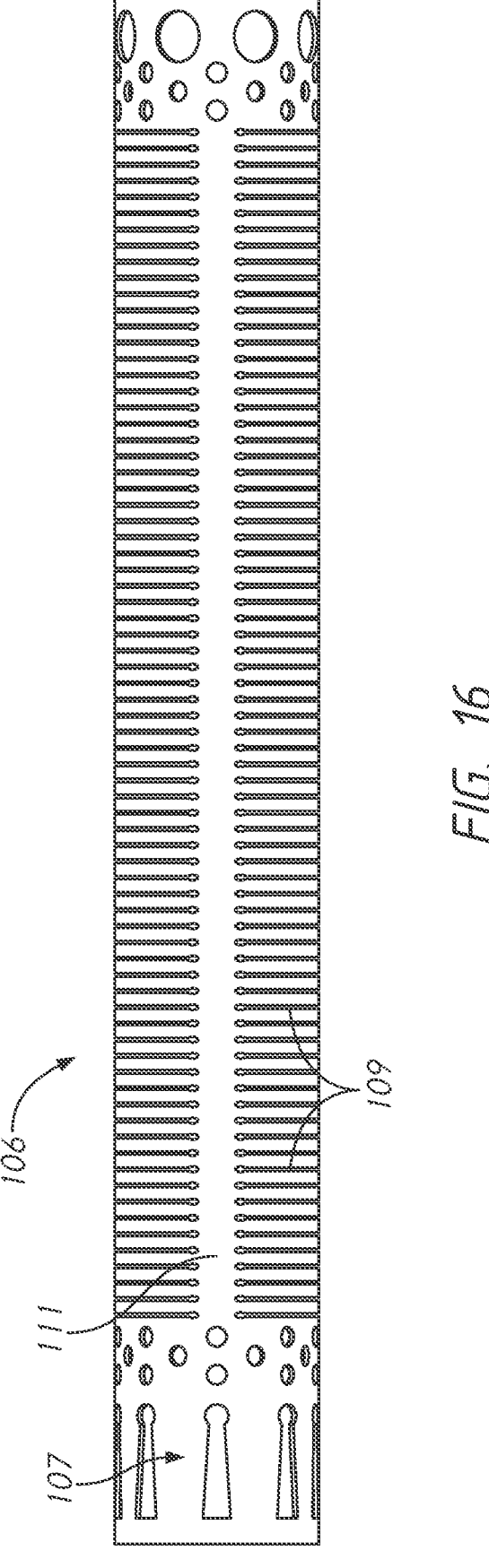
FIGS. 16-21 illustrate embodiments of a capsule construction.
Figure 17:
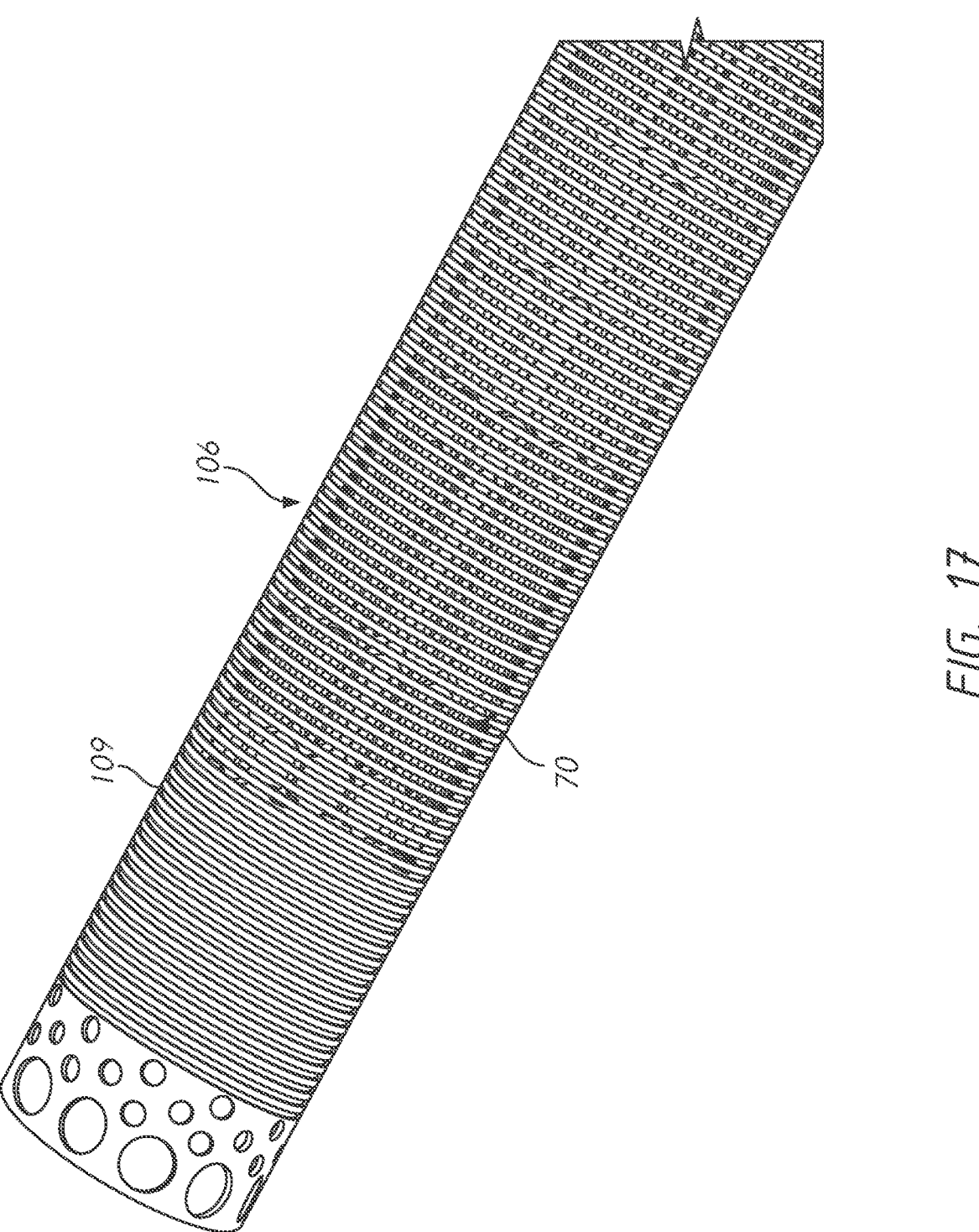

As shown in FIGS. 16-17, the capsule 106 can include a significantly large number of slots (e.g., cuts, holes) 109 that extend transverse to the axial length of the capsule (distal end is towards the left in FIG. 16 and towards the right in FIG. 17). For example, the capsule 106 can include over 50, over 100, or 150, over 200, or over 250, or over 300 cuts extending down the axial length of the capsule 106. While the flexibility could be accomplished with fewer cuts, the large number of cuts makes the open portions of the capsule 106 relatively small, so the risk of the prosthesis 70 having a negative interaction with the capsule 106 drops considerably.

In some embodiments, the capsule 106 can include one or more spines 111, where there are no slots 109. In some embodiments, the capsule 106 can have a single spine. In some embodiments, the capsule 106 can have dual spine. In some embodiments, the capsule 106 can have more than two spines, such as three, four, or five spines. Having two spines can be advantageous as it improves the compression strength while decreasing the size of cuts necessary to accomplish the same bend in a single spine configuration. In some embodiment, the spine 111 can be generally straight. In some embodiments, the spine 111 can have a substantially helical shape. In some embodiments, the spine 111 can rotate or change position around the circumference, thus allowing for different bending directions. FIG. 17 illustrates a prosthesis 70 within the capsule 106, though the particular location of the prosthesis 70 is not limiting.

Figure 18:
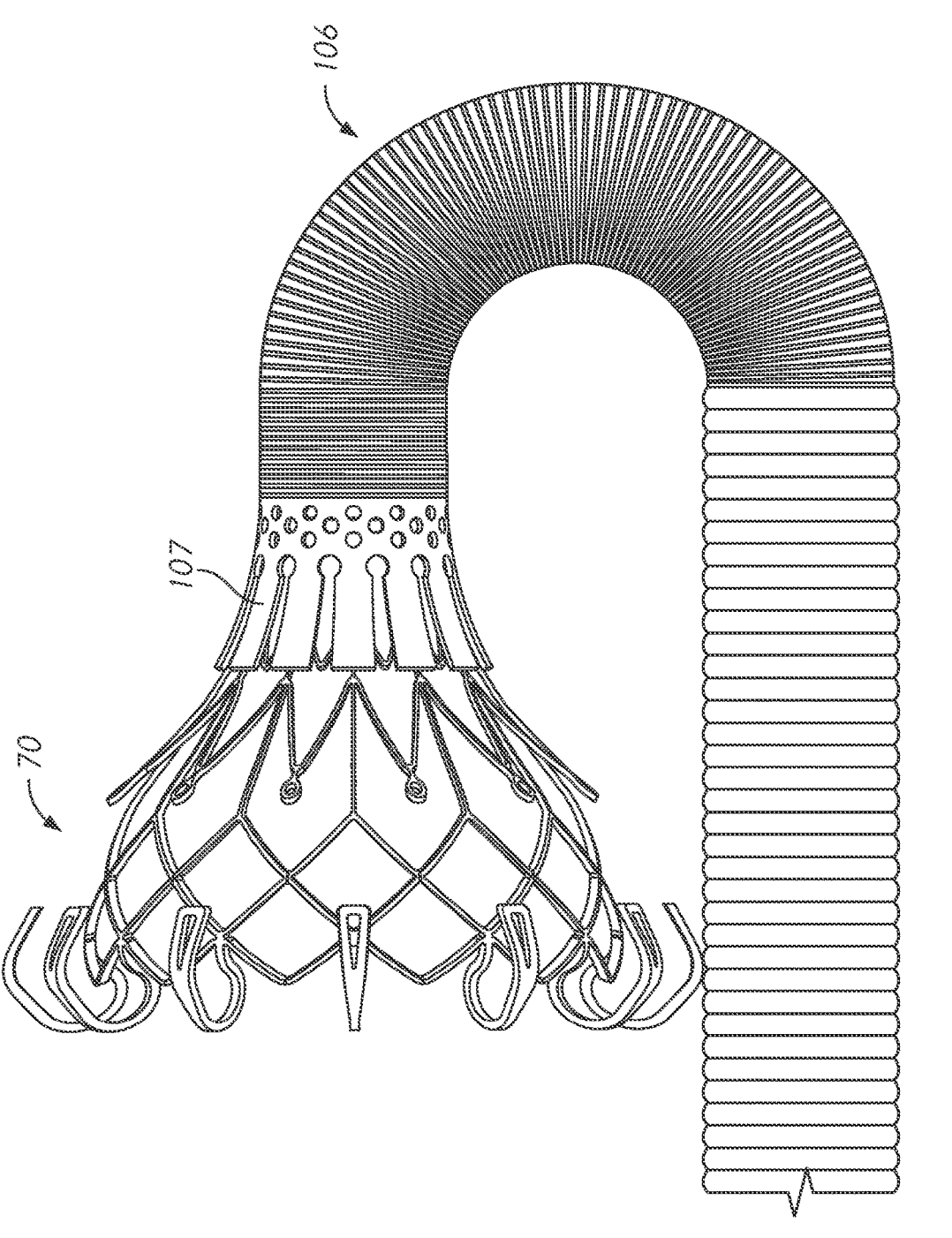

FIG. 18 illustrates the bending ability of the capsule 106 with a prosthesis 70 partially expanded. Further, as shown, the distal end of the capsule 106 can flare (e.g., expand) outwardly when a radially outward force is applied, and thus can be a flarable section 107 (also shown in FIG. 19). In some embodiments, the capsule 106 can have a flarable section 107 at its distal end. In some embodiments, it may not.

The flaring can be accomplished either by using a flexible polymer distal portion, or by a combination of a flexible polymer and lasercut as discussed below, and can be advantageous for recrimping the prosthesis 70 in a controlled manner. This can also eliminate the severity of the point of deployment when the valve expands aggressively, preventing damage to the distal end of the capsule 106. In some embodiments, the flarable section 107 can flare outwardly so that a distal end of the capsule 106 is at least 1, 2, 3, 4, 5, 10, 15, 20% or more of the diameter of the remainder of the capsule 106. In some embodiments, the flarable section 107 can flare outwards less than 2, 3, 4, 5, 10, 15, or 20% the diameter of the remainder of the capsule 106.

Figure 19:
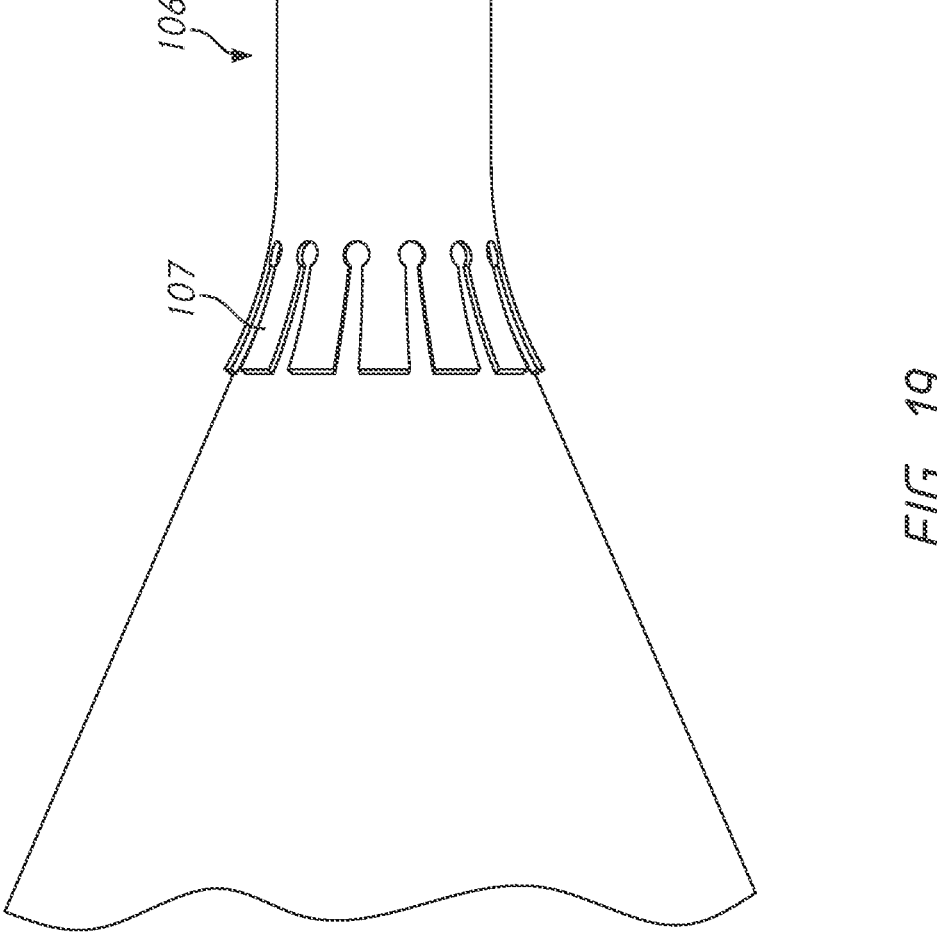
Figure 20:
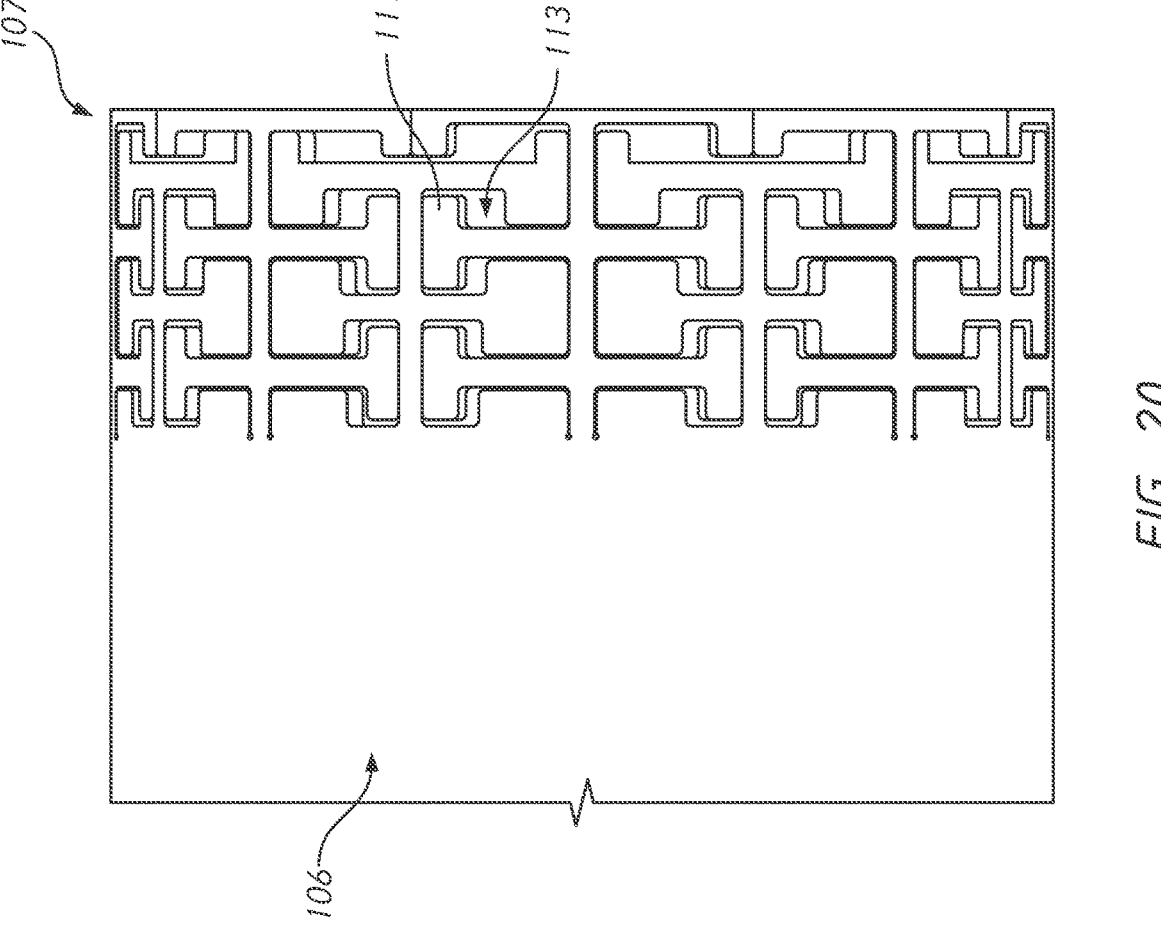
Figure 21:
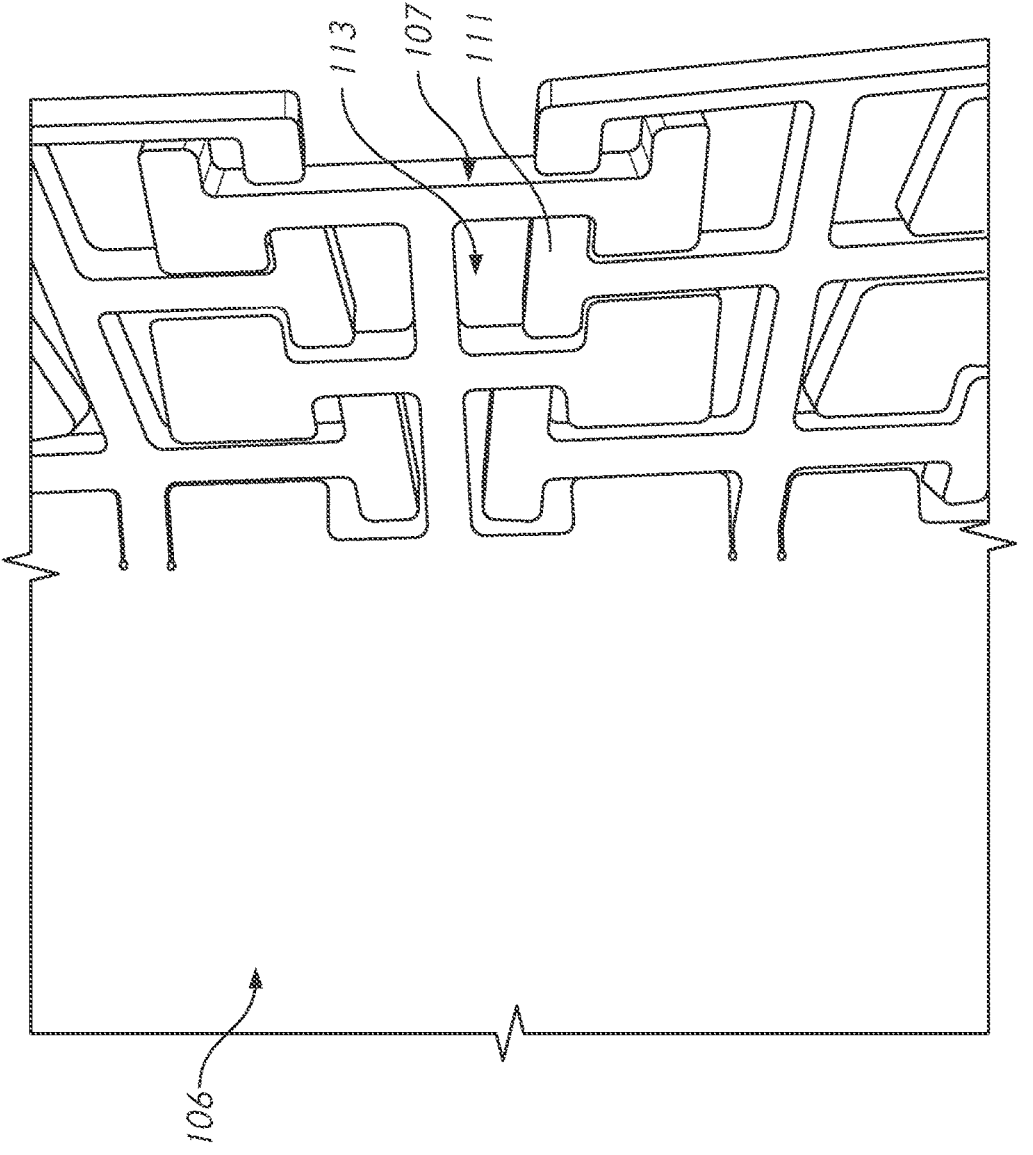

FIGS. 20-21 illustrate a closer view of the distal end of the capsule 106 (distal end towards the right). As shown, the distal end can include a flarable portion 107 that includes a number of laser cut configurations, similar to a puzzle pattern. In some embodiments, the flarable portion 107 can contain a number of generally T-shaped portions 111 extending into slots 113 that are larger than the T-shaped portions 111; however, the particular configuration is not limiting. Further, while the portions are described as T-shaped, they could include other shapes and configurations, such as t-shaped, triangular, circular, rectangular, or other polygons, and the particular shape is not limiting. The T-shaped portions 111 can vary in size/dimensions/shape to allow further spacing for the portions. Thus, the T-shaped portions 111 can slide/move within the slots 113 based on the excess room in the slots 113, allowing the flarable portion 107 to flare outwardly as shown in FIG. 21. The slots 113 can include extra room for the T-shaped portions 111 in the circumferential direction, the longitudinal direction, or both. Once the T-shaped portions 111 abut against the outer edges of the slots 113, flaring can stop. Further, the T-shaped portions 111 can have sufficient rigidity that they do not pop radially out of the slots 113. In some embodiments, expansion can occur through a number of longitudinally extending cuts around a circumference of the distal end of the capsule 106, such as shown in FIG. 19. The longitudinal cuts can end in an enlarged cut for improved flexibility, though this is not required. Additionally slots, such as the circular slots shown in FIG. 18, can be included on the capsule 106 to provide further flexibility.

Handle

Figure 22:
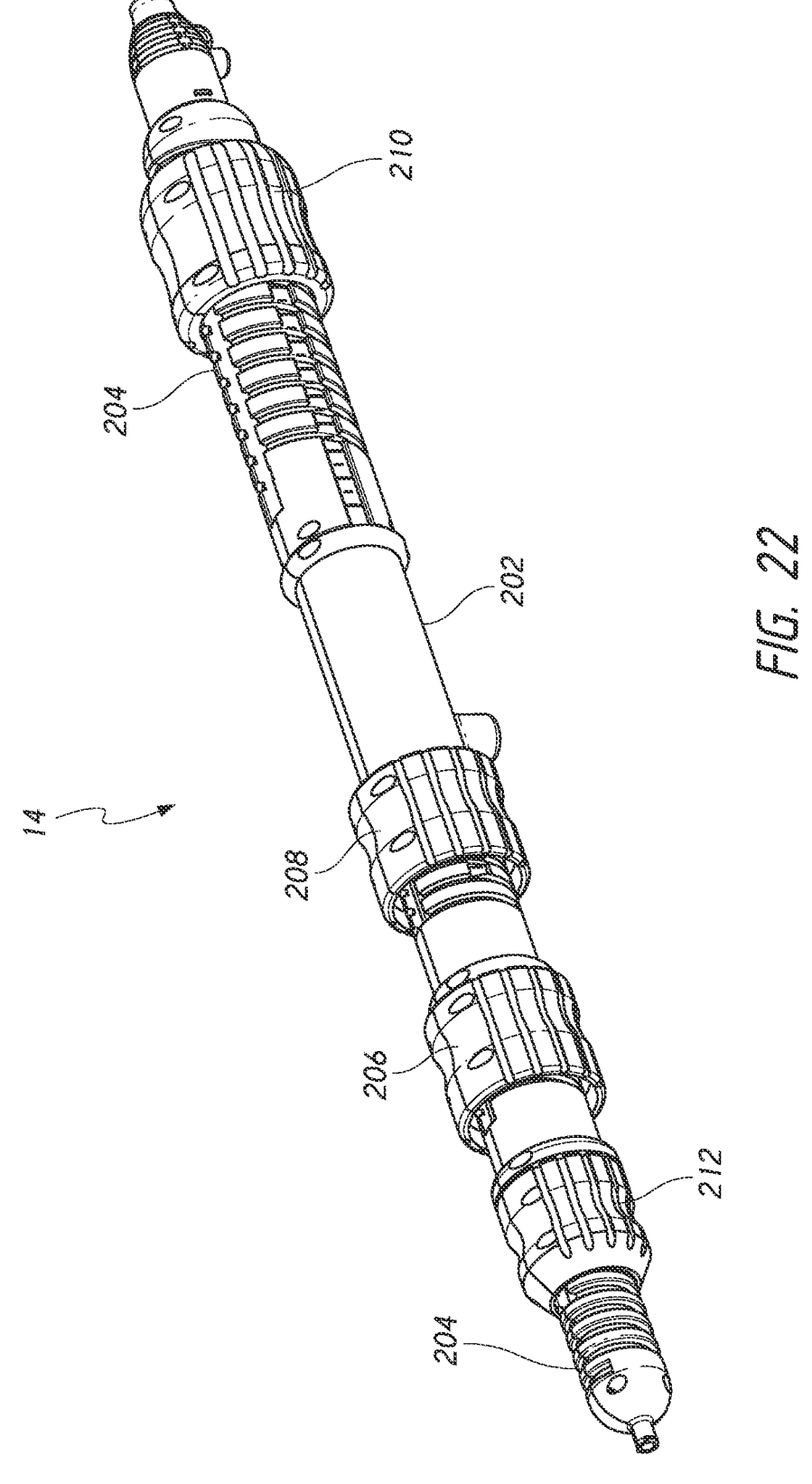
FIG. 22 illustrates an embodiment of a delivery system handle.

The handle 14 is located at the proximal end of the delivery system 10 and is shown in FIG. 22. It can include a number of actuators, such as rotatable knobs, that can manipulate different components of the delivery system. The operation of the handle 10 is described with reference to delivery of a replacement mitral valve prosthesis, though the handle 10 and delivery system 10 can be used to deliver other devices as well.

The handle 14 is generally composed of two housings, a rail housing 202 and a delivery housing 204, the rail housing 202 being circumferentially disposed around the delivery housing 204. The inner surface of the rail housing 202 can include a screwable section configured to mate with an outer surface of the delivery housing 204. Thus, the delivery housing 204 is configured to slide (e.g., screw) within the rail housing 202, as detailed below. The rail housing 202 generally surrounds about one half the length of the delivery housing 204, and thus the delivery housing 204 extends both proximally and distally outside of the rail housing 202.

The rail housing 202 can contain two rotatable knobs, a distal pull wire knob 206 and a proximal pull wire knob 208. However, the number of rotatable knobs on the rail housing 202 can vary depending on the number of pull wires used. Rotation of the distal pull wire knob 206 can provide a proximal force, thereby providing axial tension on the distal pull wires 138 and causing the distal slotted section 135 of the rail hypotube 136 to bend. The distal pull wire knob 206 can be rotated in either direction, allowing for bending in either direction. Rotation of the proximal pull wire knob 208 can provide a proximal force, and thus axial tension, on the proximal pull wires 140, thereby causing the proximal slotted section 133 of the rail hypotube 136 to bend. The proximal pull wire knob 108 can be rotated in either direction, allowing for bending in either direction. Thus, when both knobs are actuated, there can be two bends in the rail hypotube 136, thereby allowing for three dimensional steering of the rail shaft 132, and thus the distal end of the delivery system 10. Further, the proximal end of the rail shaft 132 is connected on an internal surface of the rail housing 202.

The bending of the rail shaft 132 can be used to position the system, in particular the distal end, at the desired patient location, such as at the native mitral valve. In some embodiments, rotation of the pull wire knobs 206/208 can help steer the distal end of the delivery system 10 through the septum and left atrium and into the left ventricle so that the prosthesis 70 is located at the native mitral valve.

Moving to the delivery housing 204, the proximal ends of the inner shaft assembly 19, outer sheath assembly 22, and nose cone shaft assembly 30 can be connected to an inner surface of the delivery housing 204 of the handle 14. Thus, they can move axially relative to the rail assembly 20 and rail housing 202.

A rotatable outer sheath knob 210 can be located on the distal end of the delivery housing 204, being distal to the rail housing 202. Rotation of the outer sheath knob 210 will pull the outer sheath assembly 22 in an axial direction proximally, thus pulling the capsule 106 away from the implant 70 and releasing the implant 70. The distal end 303 of the implant 70 can be released first, followed by release of the proximal end 301 of the implant 70 as the outer sheath knob 210 is continued to rotate.

Located on the proximal end of the delivery housing 204, and thus proximal to the rail housing 202, can be a rotatable depth knob 212. As the depth knob 212 is rotated, the entirety of the delivery housing 204 moves distally or proximally with respect to the rail housing 202 which will remain in the same location. Thus, at the distal end of the delivery system 10, the inner shaft assembly 18, outer sheath assembly 22, and nose cone shaft assembly 30 move proximally or distally with respect to the rail assembly 20. Accordingly, the rail shaft 132 can be aligned at a particular direction, and the other assemblies can move distally or proximally with respect to the rail shaft 132 for final positioning. The components can be advanced approximately 1, 2, 3, 5, 6, 7, 8, 9, or 10 cm along the rail shaft 132. The components can be advanced more than approximately 1, 2, 3, 5, 6, 7, 8, 9, or 10 cm along the rail shaft 132. The capsule 106 can then be withdrawn, releasing the implant 70. The assemblies other than the rail assembly 20 can then be withdrawn back over the rail shaft 132 by rotating the depth knob 212 in the opposite direction.

Valve Delivery Positioning

Methods of using the delivery system 10 in connection with a replacement mitral valve will now be described. In particular, the delivery system 10 can be used in a method for percutaneous delivery of a replacement mitral valve to treat patients with moderate to severe mitral regurgitation. The below methods are merely examples of the how the delivery system may be used. It will be understood that the delivery systems described herein can be used as part of other methods as well.

Figure 23:
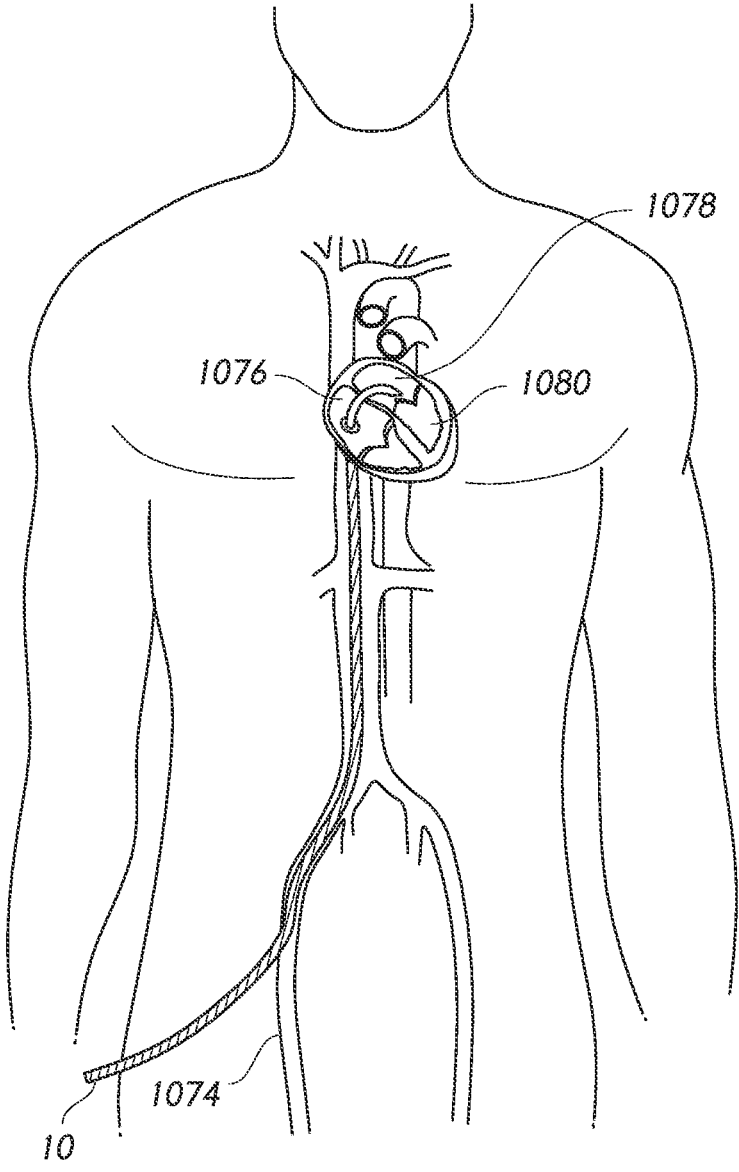
FIG. 23 illustrates a schematic representation of a transfemoral delivery approach.

As shown in FIG. 23, in one embodiment, the delivery system 10 can be placed in the ipsilateral femoral vein 1074 and advanced toward the right atrium 1076. A transseptal puncture using known techniques can then be performed to obtain access to the left atrium 1078. The delivery system 10 can then be advanced in to the left atrium 1078 and then to the left ventricle 1080. FIG. 23 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may be used.

Accordingly, it can be advantageous for a user to be able to steer the delivery system 10 through the complex areas of the heart in order to position a replacement mitral valve in line with the native mitral valve. This task can be performed with or without the use of a guide wire with the above disclosed system. The distal end of the delivery system can be advanced into the left atrium 1078. A user can then manipulate the rail assembly 20 to target the distal end of the delivery system 10 to the appropriate area. A user can then continue to pass the bent delivery system 10 through the transseptal puncture and into the left atrium 1078. A user can then further manipulate the delivery system 10 to create an even greater bend in the rail assembly 20. Further, a user can torque the entire delivery system 10 to further manipulate and control the position of the delivery system 10. In the fully bent configuration, a user can then place the replacement mitral valve in the proper location. This can advantageously allow delivery of a replacement valve to an in situ implantation site, such as a native mitral valve, via a wider variety of approaches, such as a transseptal approach.

Figure 24:
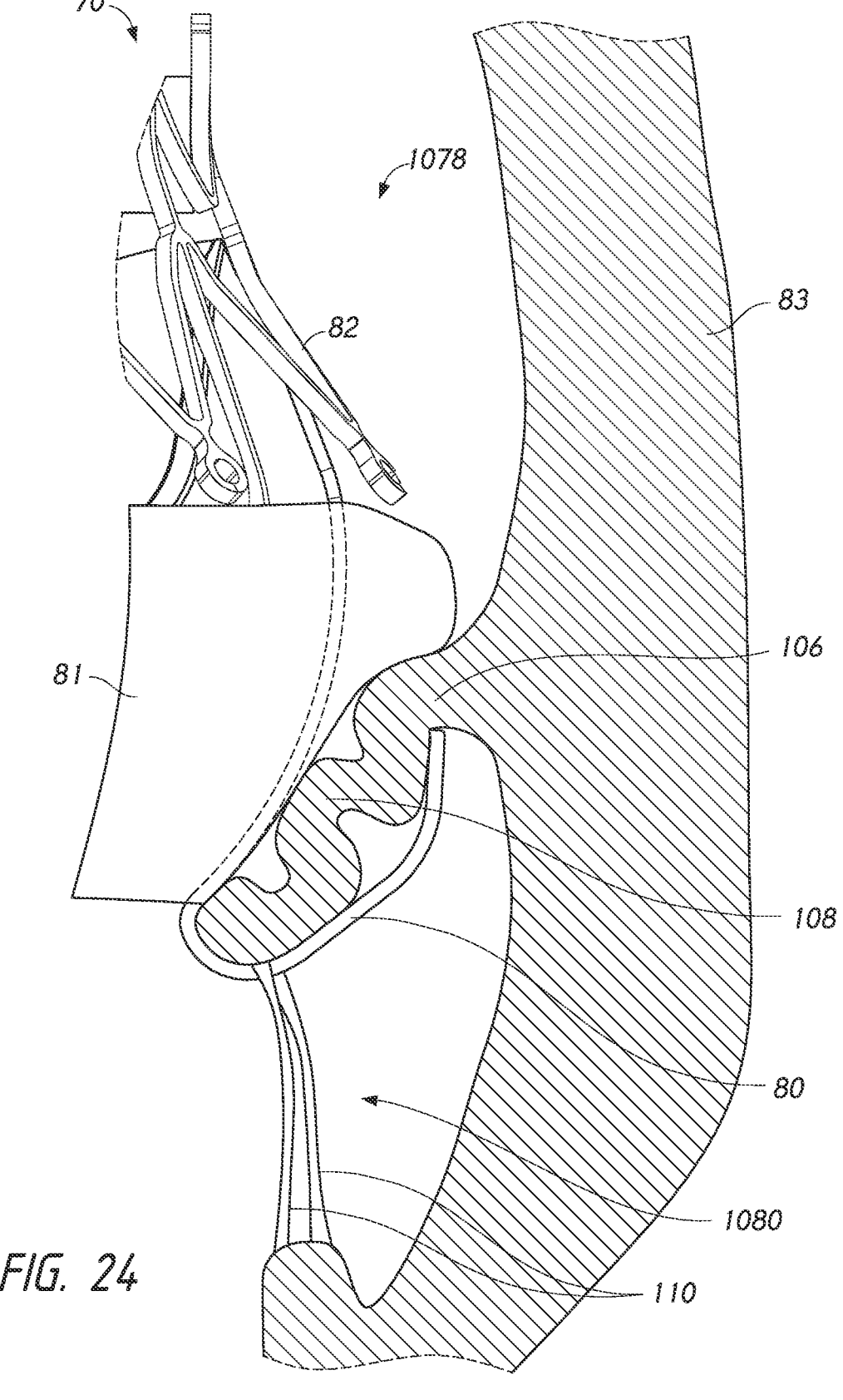
FIG. 24 illustrates a schematic representation of a valve prosthesis positioned within a native mitral valve.

Reference is now made to FIG. 24 which illustrates a schematic representation of a portion of an embodiment of a replacement heart valve (prosthesis 70) positioned within a native mitral valve of a heart 83. Further details regarding how the prosthesis 70 may be positioned at the native mitral valve are described in U.S. patent application Ser. No. 14/716,507, filed May 19, 2015, published as U.S. 2015/0328000, the entirety of which is hereby incorporated by reference, including but not limited to FIGS. 13A-15 and paragraphs [0036]-[0045]. A portion of the native mitral valve is shown schematically and represents typical anatomy, including a left atrium 1078 positioned above an annulus 106 and a left ventricle 1080 positioned below the annulus 106. The left atrium 1078 and left ventricle 1080 communicate with one another through a mitral annulus 106. Also shown schematically in FIG. 24 is a native mitral leaflet 108 having chordae tendineae 110 that connect a downstream end of the mitral leaflet 108 to the papillary muscle of the left ventricle 1080. The portion of the prosthesis 70 disposed upstream of the annulus 106 (toward the left atrium 1078) can be referred to as being positioned supra-annularly. The portion generally within the annulus 106 is referred to as positioned intra-annularly. The portion downstream of the annulus 106 is referred to as being positioned sub-annularly (toward the left ventricle 1080).

As shown in FIG. 24, the replacement heart valve (e.g., prosthesis 70) can be positioned so that the mitral annulus 106 is located between the distal anchors 80 and the proximal anchors 82. In some situations, the prosthesis 70 can be positioned such that ends or tips of the distal anchors 80 contact the annulus 106 as shown, for example, in FIG. 24. In some situations, the prosthesis 70 can be positioned such that ends or tips of the distal anchors 80 do not contact the annulus 106. In some situations, the prosthesis 70 can be positioned such that the distal anchors 80 do not extend around the leaflet 108.

As illustrated in FIG. 24, the replacement heart valve 70 can be positioned so that the ends or tips of the distal anchors 80 are on a ventricular side of the mitral annulus 106 and the ends or tips of the proximal anchors 82 are on an atrial side of the mitral annulus 106. The distal anchors 80 can be positioned such that the ends or tips of the distal anchors 80 are on a ventricular side of the native leaflets beyond a location where chordae tendineae 110 connect to free ends of the native leaflets. The distal anchors 80 may extend between at least some of the chordae tendineae 110 and, in some situations such as those shown in FIG. 24, can contact or engage a ventricular side of the annulus 106. It is also contemplated that in some situations, the distal anchors 80 may not contact the annulus 106, though the distal anchors 80 may still contact the native leaflet 108. In some situations, the distal anchors 80 can contact tissue of the left ventricle 104 beyond the annulus 106 and/or a ventricular side of the leaflets.

During delivery, the distal anchors 80 (along with the frame) can be moved toward the ventricular side of the annulus 106 with the distal anchors 80 extending between at least some of the chordae tendineae 110 to provide tension on the chordae tendineae 110. The degree of tension provided on the chordae tendineae 110 can differ. For example, little to no tension may be present in the chordae tendineae 110 where the leaflet 108 is shorter than or similar in size to the distal anchors 80. A greater degree of tension may be present in the chordae tendineae 110 where the leaflet 108 is longer than the distal anchors 80 and, as such, takes on a compacted form and is pulled proximally. An even greater degree of tension may be present in the chordae tendineae 110 where the leaflets 108 are even longer relative to the distal anchors 80. The leaflet 108 can be sufficiently long such that the distal anchors 80 do not contact the annulus 106.

Figure 25:
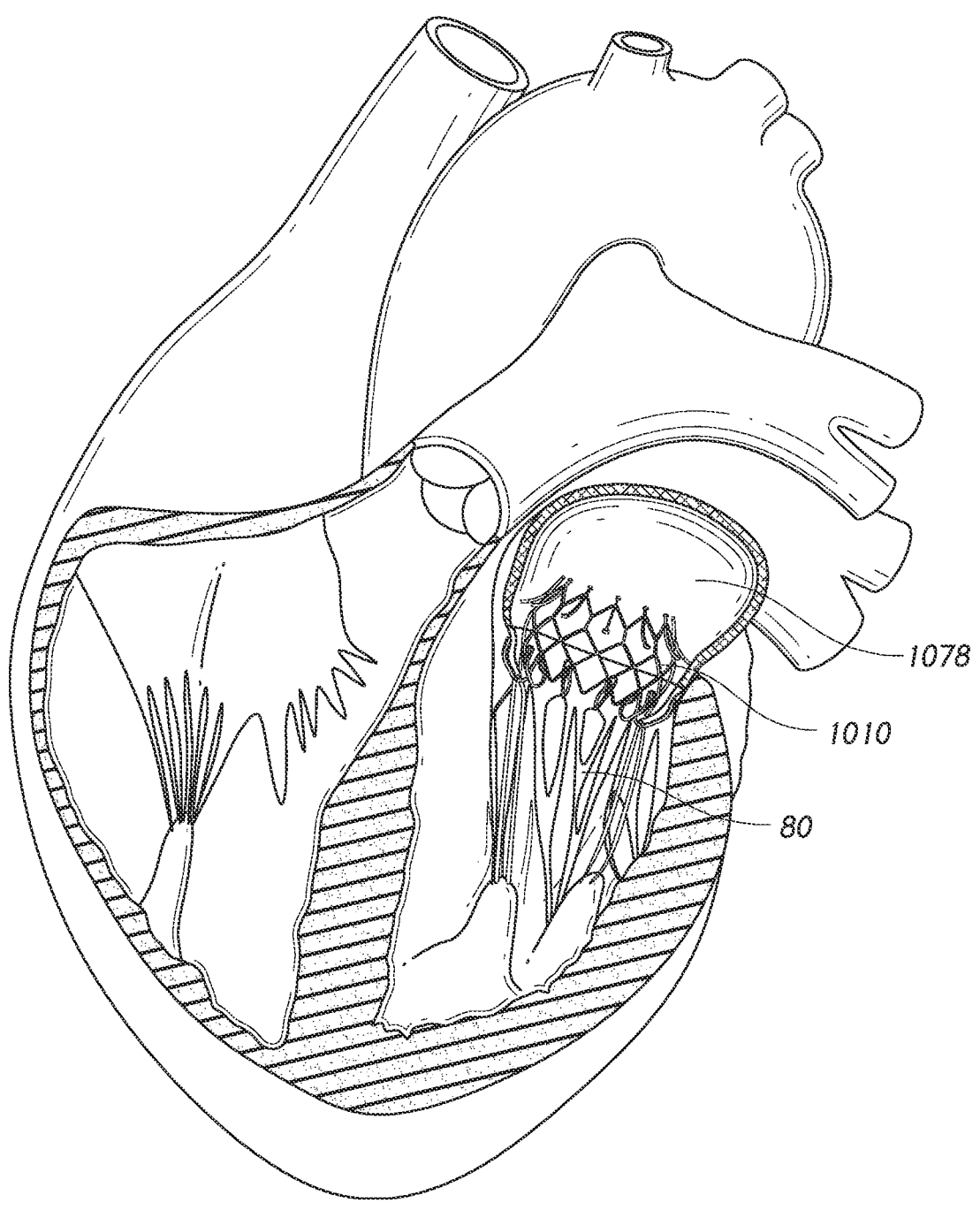
FIG. 25 shows the valve prosthesis frame located within a heart.

The proximal anchors 82, if present, can be positioned such that the ends or tips of the proximal anchors 82 are adjacent the atrial side of the annulus 106 and/or tissue of the left atrium 1078 beyond the annulus 106. In some situations, some or all of the proximal anchors 82 may only occasionally contact or engage atrial side of the annulus 106 and/or tissue of the left atrium 1078 beyond the annulus 106. For example, as illustrate in FIG. 24, the proximal anchors 82 may be spaced from the atrial side of the annulus 106 and/or tissue of the left atrium 1078 beyond the annulus 106. The proximal anchors 82 could provide axial stability for the prosthesis 70. It is also contemplated that some or all of the proximal anchors 82 may contact the atrial side of the annulus 106 and/or tissue of the left atrium 1078 beyond the annulus 106. FIG. 25 illustrates the prosthesis 70 implanted in the heart. Although the illustrated replacement heart valve includes both proximal and distal anchors, it will be appreciated that proximal and distal anchors are not required in all cases. For example, a replacement heart valve with only distal anchors may be capable of securely maintaining the replacement heart valve in the annulus. This is because the largest forces on the replacement heart valve are directed toward the left atrium during systole. As such, the distal anchors are most important for anchoring the replacement heart valve in the annulus and preventing migration.

Delivery Method

Figure 26:
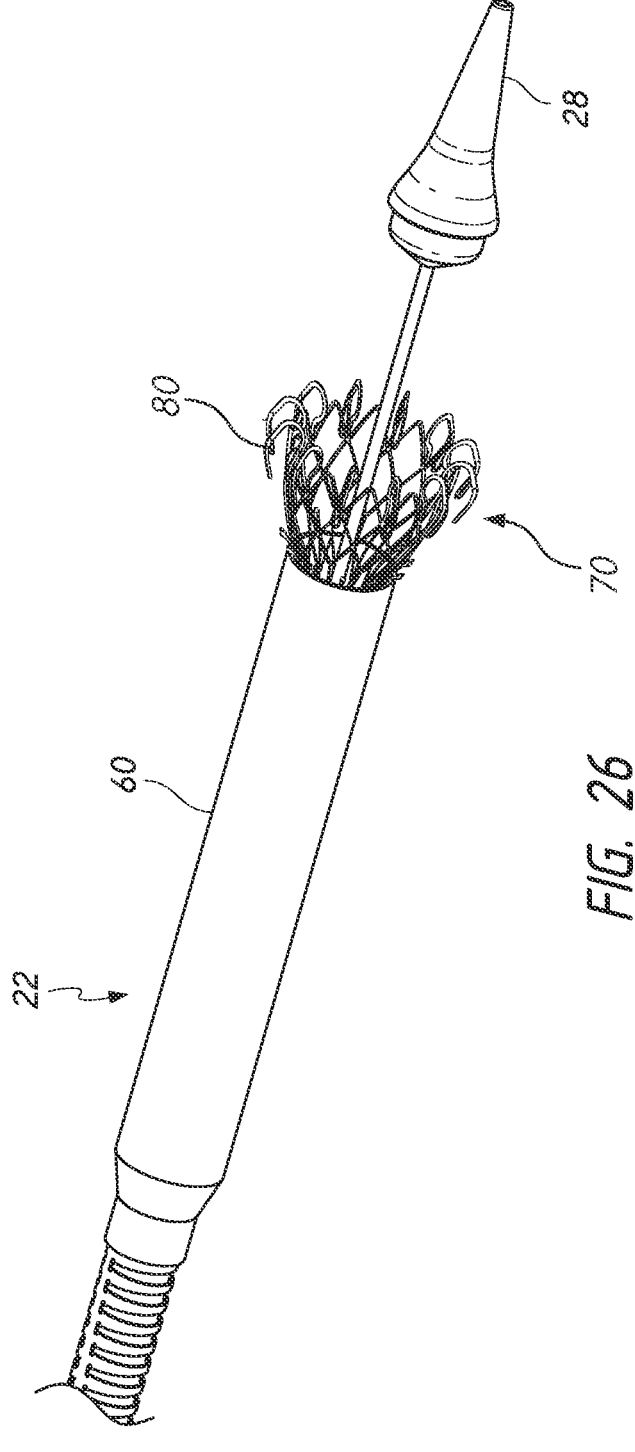
FIGS. 26-28 show steps of a method for delivery of the valve prosthesis to an anatomical location.
Figure 27:
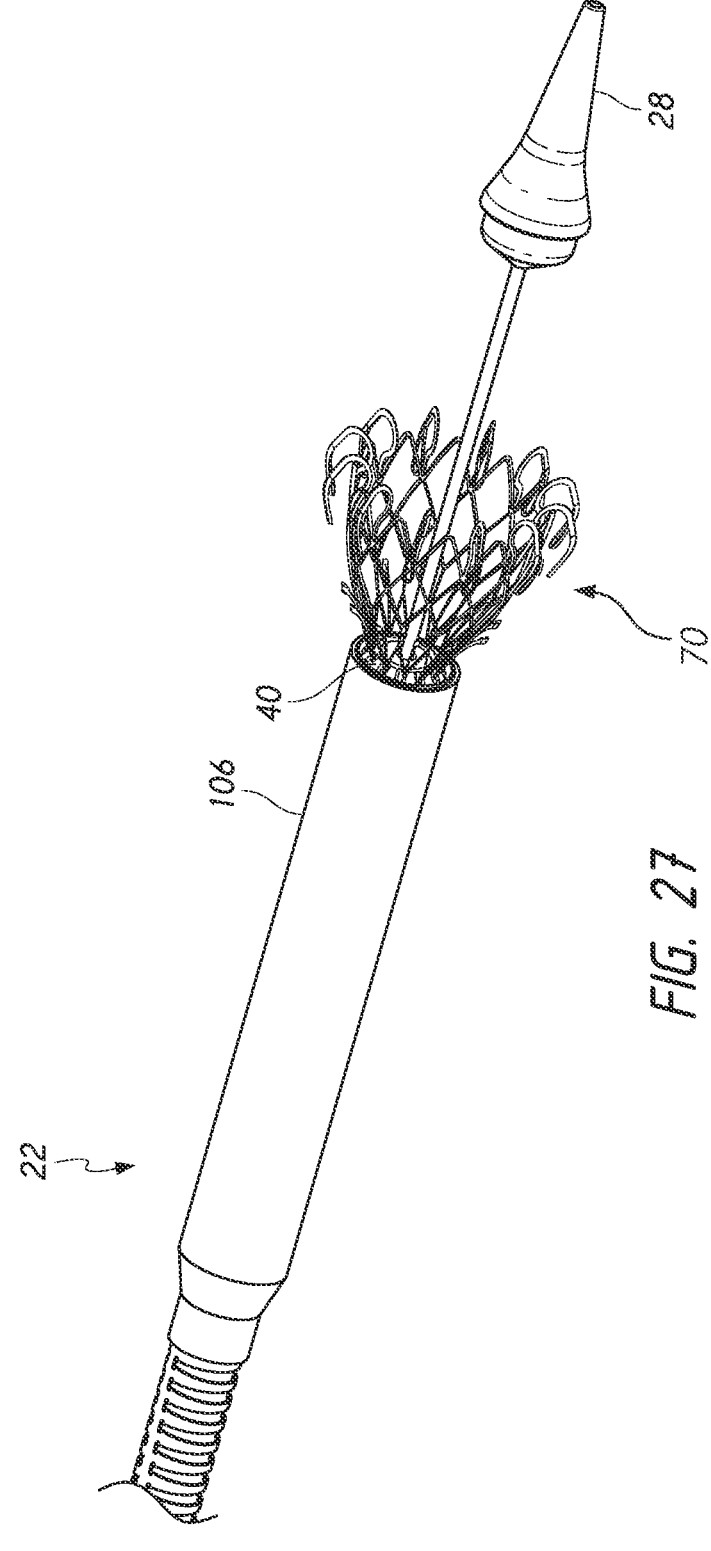
Figure 28:
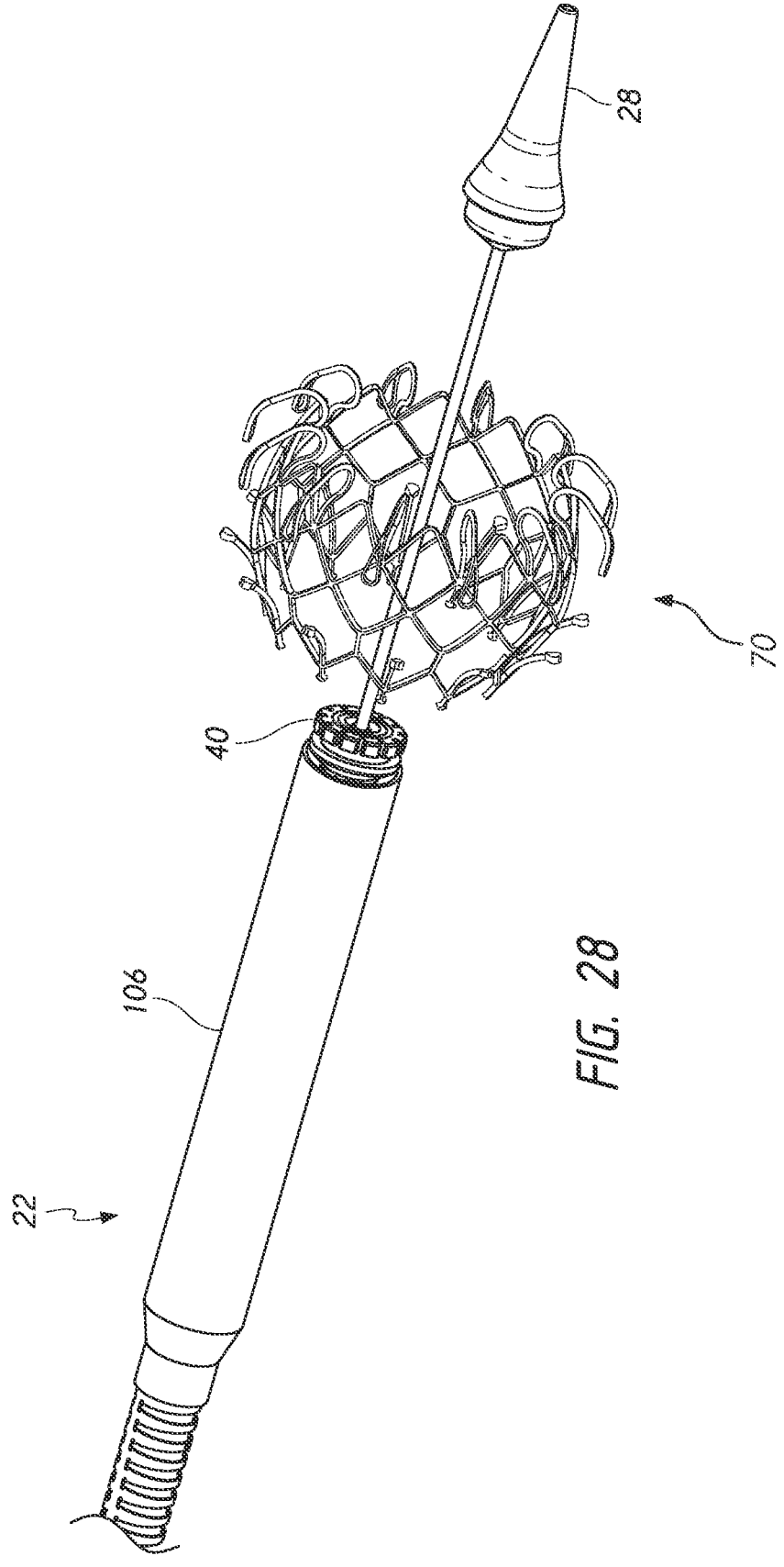

FIGS. 26-28 illustrate the release mechanism of the delivery system 10. During the initial insertion of the prosthesis 70 and the delivery system 10 into the body, the prosthesis 70 can be located within the system 10, similar to as shown in FIG. 2A. The distal end 303 of the prosthesis 70, and specifically the distal anchors 80, are restrained within the capsule 106 of the outer sheath assembly 22, thus preventing expansion of the prosthesis 70. Similar to what is shown in FIG. 2A, the distal anchors 80 can extend distally when positioned in the capsule. The proximal end 301 of the prosthesis 70 is restrained within the capsule 106 and within a portion of the inner retention member 40 and thus is generally constrained between the capsule 106 and the inner retention member 40.

The system 10 can first be positioned to a particular location in a patient's body, such as at the native mitral valve, through the use of the steering mechanisms discussed herein or other techniques.

Once the prosthesis 70 is loaded into the delivery system 10, a user can thread a guide wire into a patient to the desired location. The guide wire passes through the lumen of the nose cone assembly 30, and thus the delivery system 10 can be generally advanced through the patient's body following the guide wire. The delivery system 10 can be advanced by the user manually moving the handle 14 in an axial direction. In some embodiments, the delivery system 10 can be placed into a stand while operating the handle 14 controls.

Once generally in heart, the user can begin the steering operation of the rail assembly 20 using the distal pull wire knob 206 and/or the proximal pull wire knob 208. By turning either of the knobs, the user can provide flexing/ bending of the rail assembly 20 (either on the distal end or the proximal end), thus bending the distal end of the delivery system 10 into the desired configuration. As discussed above, the user can provide multiple bends in the rail assembly 20 to direct the delivery system 10 towards the mitral valve.

The user can also rotate and/or move the handle 14 itself in a stand for further fine tuning of the distal end of the delivery system 10. The user can continually turn the proximal and/or distal pull wire knobs 208/206, as well as moving the handle 14 itself, to orient the delivery system 10 for release of the prosthesis 70 in the body.

In a next step, the user can rotate the depth knob 212. As discussed, rotation of this knob 212 advances the inner shaft assembly 18, outer sheath assembly 22, and nose cone assembly 30 over/through the rail assembly 20. Due to the rigidity of, for example, the inner shaft assembly 18, these assemblies proceed straight forward in the direction aligned by the rail assembly 20.

Once in the release position, the user can rotate the outer sheath knob 210, which translates the outer sheath assembly 22 (and thus the capsule 106) in a proximal direction towards the handle 14 as shown in FIG. 26. By doing so, the prosthesis 70 is uncovered in the body, allowing for the beginning of expansion. At this point, the distal anchors 80 can flip proximally and the distal end 303 begins to expand radially outwardly. For example, if the system 10 has been delivered to a native mitral valve location through a transseptal approach, the nose cone is positioned in the left ventricle, preferably aligning the prosthesis 70 such that it is generally perpendicular to the plane of the mitral annulus. The distal anchors 80 expand radially outwardly within the left ventricle. The distal anchors 80 can be located above the papillary heads, but below the mitral annulus and mitral leaflets. In some embodiments, the distal anchors 80 may contact and/or extend between the chordae in the left ventricle, as well as contact the leaflets, as they expand radially. In some embodiments, the distal anchors 80 may not contact and/or extend between the chordae or contact the leaflets. Depending on the position of the prosthesis 70, the distal ends of the distal anchors 80 may be at or below where the chordae connect to the free edge of the native leaflets.

With reference next to the step of FIG. 27, outer sheath assembly 22 can be further moved relatively away from the nose cone 28 to further uncover the prosthesis 70. As shown in the illustrated embodiment, the distal end 303 of the prosthesis 70 is expanded outwardly. It should be noted that the proximal end 301 of the prosthesis 70 can remain covered by the capsule 106 during this step such that the proximal end 301 remains in a radially compacted state. At this time, the system 10 may be withdrawn proximally so that the distal anchors 80 capture and engage the leaflets of the mitral valve, or may be moved proximally to reposition the prosthesis 70. Further, the system 10 may be torqued, which may cause the distal anchors 80 to put tension on the chordae through which at least some of the distal anchors may extend between. However, in some embodiments, the distal anchors 80 do not apply tension on the chordae. In some embodiments, the distal anchors 80 may capture the native leaflet and be between the chordae without any further movement of the system 10 after withdrawing the outer sheath assembly 22.

During this step, the system 10 may be moved proximally or distally to cause the distal or ventricular anchors 80 to properly capture the native mitral valve leaflets. In particular, the tips of the ventricular anchors 80 may be moved proximally to engage a ventricular side of the native annulus, so that the native leaflets are positioned between the anchors 80 and the body of the prosthesis 70. When the prosthesis 70 is in its final position, there may or may not be tension on the chordae, though the distal anchors 80 can be located between at least some of the chordae.

If an outer retention ring 42 is used, the distal end 303 of the prosthesis 70 will remain in the outer retention ring 42 after retraction of the capsule 106. The outer retention ring 42 can then be retracted proximally to release the distal end 303 of the prosthesis 70.

As shown in FIG. 28, once the distal end 303 of the prosthesis 70 is fully expanded (or as fully expanded as possible at this point), capsule 106 can be further moved relatively proximally to expose the inner retention member 40, thus beginning the expansion of the proximal end 301 of the prosthesis 70. For example, in a mitral valve replacement procedure, after the distal or ventricular anchors 80 are positioned between at least some of the chordae tendineae and/or engage the native mitral valve annulus, the proximal end 301 of the prosthesis 70 may be expanded within the left atrium.

The capsule 106 can continue to be moved proximally such that the proximal end 310 of the prosthesis 70 can radially expand to its fully expanded configuration. After expansion and release of the prosthesis 70, the nose cone 28 can be withdrawn through the center of the expanded prosthesis 70 and into the outer sheath assembly 22. The system 10 can then be removed from the patient.

Figure 29A:
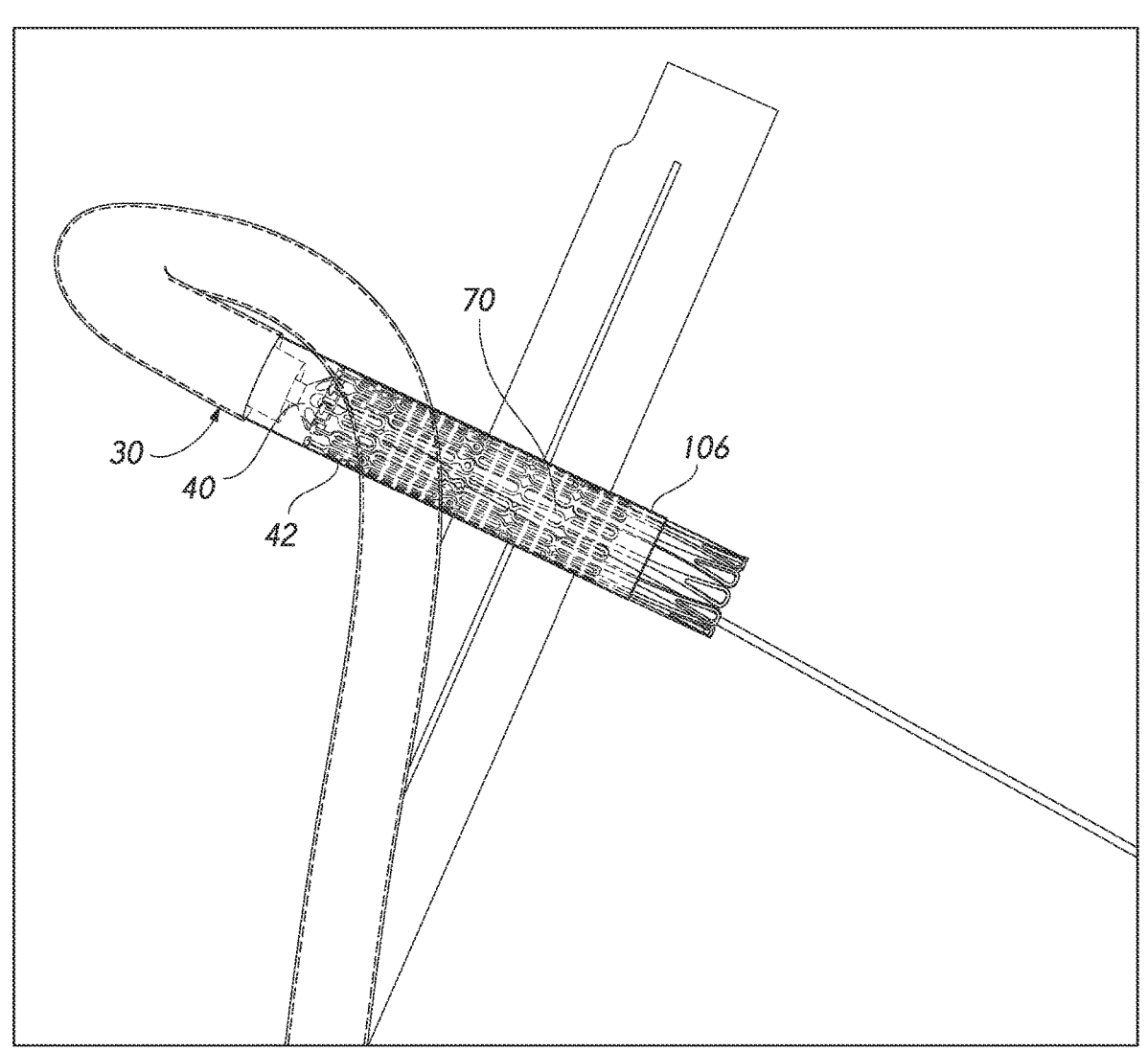
FIGS. 29A-B illustrate the methodology of the rail delivery system.
Figure 29B:
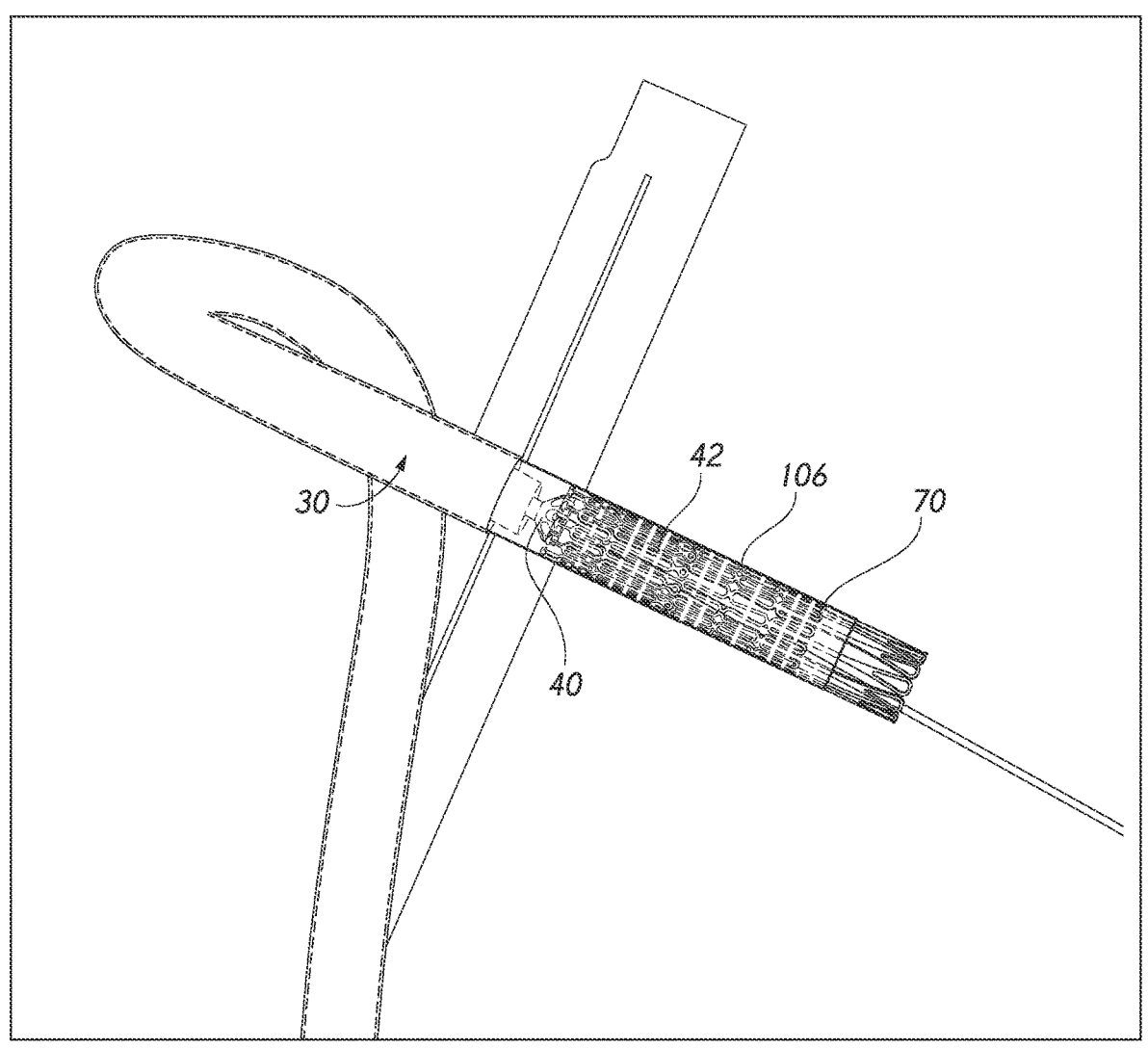

FIGS. 29A-B illustrate the advancement of the different assemblies over the rail assembly 20. FIG. 29A illustrates the assemblies in their proximalmost position over the rail assembly 20. FIG. 29B illustrates the assemblies in their distalmost position as compared to the rail assembly 20. Thus, the assemblies snake along the rail assembly 20 and extend distally away.

In some embodiments, the prosthesis 70 can be delivered under fluoroscopy so that a user can view certain reference points for proper positioning of the prosthesis 70. Further, echocardiography can be used for proper positioning of the prosthesis 70.

Following is a discussion of an alternative implantation method for delivering a replacement mitral valve to a mitral valve location. Elements of the below can be incorporated into the above discussion and vice versa. Prior to insertion of the delivery system 10, the access site into the patient can be dilated. Further, a dilator can be flushed with, for example, heparinized saline prior to use. The delivery system 10 can then be inserted over a guide wire. In some embodiments, any flush ports on the delivery system 10 can be pointed vertically. Further, if an introducer tube is used, integrated or otherwise, this can be stabilized. The delivery system 10 can be advanced through the septum until a distal end of the delivery system 10 is positioned across the septum into the left atrium 1078. Thus, the distal end of the delivery system 10 can be located in the left atrium 1078. In some embodiments, the delivery system 10 can be rotated, such as under fluoroscopy, into a desired position. The rail can be flex so that direct a distal end of the delivery system 10 towards the septum and mitral valve. The position of the delivery system 10, and the prosthesis 70 inside, can be verified using echocardiography and fluoroscopic guidance.

In some embodiments, the prosthesis 70 can be located, prior to release, above the mitral annulus 106, in line with the mitral annulus 106, or below the mitral annulus 106. In some embodiments, the prosthesis 70 can be located, prior to expansion, fully above the mitral annulus 106, in line with the mitral annulus 106, just below the mitral annulus 106, or fully below the mitral annulus 106. In some embodiments, the prosthesis 70 can be located, prior to expansion, partially above the mitral annulus 106, in line with the mitral annulus 106, or partially below the mitral annulus 106. In some embodiments, a pigtail catheter can be introduced into the heart to perform a ventriculogram for proper viewing.

In some embodiments, the position of the mitral plane and the height of any papillary muscles on the fluoroscopy monitor can be marked to indicate an example target landing zone. If needed, the delivery system 10 can be unflexed, reduced in rotation, and retracted to reduce tension on the delivery system 10 as well as reduce contact with the left ventricular wall, the left atrial wall, and/or the mitral annulus 106.

Further, the delivery system 10 can be positioned to be coaxial to the mitral annulus 106, or at least as much as possible, while still reducing contact with the left ventricular wall, the left atrial wall, and/or the mitral annulus 106 and reducing delivery system tension. An echo probe can be positioned to view the anterior mitral leaflet (AML), the posterior mitral leaflet (PML) (leaflets 108), mitral annulus 106, and outflow tract. Using fluoroscopy and echo imaging, the prosthesis 1010 can be confirmed to be positioned at a particular depth and coaxiality with the mitral annulus 106.

Afterwards, the outer sheath assembly 22 can be retracted to expose the ventricular anchors 80, thereby releasing them.

In some embodiments, once exposed, the outer sheath assembly 22 can be reversed in direction to relieve tension on the outer sheath assembly 22. In some embodiments, reversing the direction could also serve to partially or fully capture the prosthesis 70.

The distal anchors 80 can be released in the left atrium 1078. Further, the proximal anchors 82, if included in the prosthesis 70, are not yet exposed. Moreover, the body of the prosthesis 70 has not undergone any expansion at this point. However, in some embodiments, one or more of the distal anchors 80 can be released in either the left atrium 1078 (e.g., super-annular release) or generally aligned with the mitral valve annulus 106 (e.g., intra-annular release), or just below the mitral valve annulus 106 (e.g., sub-annular release). In some embodiments, all of the distal anchors 80 can be released together. In other embodiments, a subset of the distal anchors 80 can be released while at a first position and another subset of the distal anchors 80 can be released while at a second position. For example, some of the distal anchors 80 can be released in the left atrium 1078 and some of the distal anchors 80 can be released while generally aligned with the mitral valve annulus 106 or just below the mitral valve annulus 106.

If the distal anchors 80 are released "just below" the mitral valve annulus 106, the may be released at 1 inch, ¾ inch, ½ inch, ¼ inch, ⅛ inch, ¹⁄₁₀ inch or ¹⁄₂₀ inch below the mitral valve annulus 106. In some embodiments, the distal anchors 80 the may be released at less than 1 inch, ¾ inch, ½ inch, ¼ inch, ⅛ inch, ¹⁄₁₀ inch or ¹⁄₂₀ inch below the mitral valve annulus 106. This may allow the distal anchors 80 to snake through the chordae upon release. This can advantageously allow the prosthesis 70 to slightly contract when making the sharp turn down toward the mitral valve. In some embodiments, this may eliminate the need for a guide wire assisting to cross the mitral valve. In some embodiments, the guide wire may be withdrawn into the delivery system 10 before or following release of the distal anchors 80.

In some embodiments, the distal anchors 80 can be released immediately after crossing the septum, and then the final trajectory of the delivery system 10 can be determined. Thus, the delivery system 10 can cross the septum, release the ventricular anchors 80, establish a trajectory, and move into the left ventricle to capture the leaflets.

As discussed in detail above, upon release from the delivery system 10, the distal anchors 80 can flip from extending distally to extending proximally. This flip can be approximately 180°. Accordingly, in some embodiments, the distal anchors 80 can be flipped in either the left atrium 1078 (e.g., super-annular flip), generally aligned with the mitral valve annulus 106 (e.g., intra-annular flip), or just below the mitral valve annulus 106 (e.g., sub-annular flip). The proximal anchors 82, if any, can remain within the delivery system 10. In some embodiments, all of the distal anchors 80 can be flipped together. In other embodiments, a subset of the distal anchors 80 can be flipped while at a first position and another subset of the distal anchors 80 can be released while at a second position. For example, some of the distal anchors 80 can be flipped in the left atrium 1078 and some of the distal anchors 80 can be flipped while generally aligned with the mitral valve annulus 106 or just below the mitral valve annulus 106.

In some embodiments, the distal anchors 80 may be positioned in line with the annulus 106 or just below the annulus 106 in the non-flipped position. In some embodiments, the distal anchors 80 may be position in line with the annulus 106 or just below the annulus 106 in the flipped position. In some embodiments, prior to flipping the distalmost portion of the prosthesis 70 can be located within or below the mitral valve annulus 106, such as just below the mitral valve annulus 106. However, flipping the anchors can cause, without any other movement of the delivery system 10, the distalmost portion of the prosthesis 70/anchors 80 to move upwards, moving it into the left atrium 1078 or moving it in line with the mitral annulus 106. Thus, in some embodiments the distal anchors 80 can begin flipping at the annulus 106 but be fully within the left atrium 1078 upon flipping. In some embodiments the distal anchors 80 can begin flipping below the annulus 106 but be fully within the annulus 106 upon flipping.

In some embodiments, the distal anchors 80 can be proximal (e.g., toward the left atrium 1078) of a free edge of the mitral leaflets 108 upon release and flipping. In some embodiments, the distal anchors 80 can be aligned with (e.g., toward the left atrium 1078) a free edge of the mitral leaflets 108 upon release and flipping. In some embodiments, the distal anchors 80 can be proximal (e.g., toward the left atrium 1078) of a free edge of the mitral valve annulus 106 upon release and flipping. In some embodiments, the distal anchors 80 can be aligned with (e.g., toward the left atrium 1078) a free edge of the mitral valve annulus 106 upon release and flipping.

Thus, in some embodiments the distal anchors 80 can be released/flipped above where the chordae 110 attach to the free edge of the native leaflets 108. In some embodiments the distal anchors 80 can be released/flipped above where some the chordae 110 attach to the free edge of the native leaflets 108. In some embodiments the distal anchors 80 can be released/flipped above where all the chordae 110 attach to the free edge of the native leaflets 108. In some embodiments, the distal anchors 80 can be released/flipped above the mitral valve annulus 106. In some embodiments, the distal anchors 80 can be released/flipped above the mitral valve leaflets 108. In some embodiments, the distal anchors 80 can be released/flipped generally in line with the mitral valve annulus 106. In some embodiments, the distal anchors 80 can be released/flipped generally in line with the mitral valve leaflets 108. In some embodiments, the tips of the distal anchors 80 can be released/flipped generally in line with the mitral valve annulus 106. In some embodiments, the tips of the distal anchors 80 can be released/flipped generally in line with the mitral valve leaflets 108. In some embodiments the distal anchors 80 can be released/flipped below where some the chordae 110 attach to the free edge of the native leaflets 108. In some embodiments the distal anchors 80 can be released/flipped below where all the chordae 110 attach to the free edge of the native leaflets 108. In some embodiments, the distal anchors 80 can be released/flipped below the mitral valve annulus 106. In some embodiments, the distal anchors 1024 can be released/flipped below the mitral valve leaflets 108.

Once the distal anchors 80 are released and flipped, the delivery system 10 can be translated towards the left ventricle 1080 through the mitral valve annulus 106 so that the distal anchors 80 enter the left ventricle 1080. In some embodiments, the distal anchors 80 can compress when passing through the mitral valve annulus 106. In some embodiments, the prosthesis 70 can compress when passing through the mitral valve annulus 106. In some embodiments, the prosthesis 70 does not compress when it passes through the mitral annulus 106. The distal anchors 80 can be delivered anywhere in the left ventricle 1080 between the leaflets 108 and the papillary heads.

In some embodiments, the distal anchors 80 are fully expanded prior to passing through the mitral valve annulus 106. In some embodiments, the distal anchors 80 are partially expanded prior to passing through the mitral valve annulus 106 and continued operation of the delivery system 10 can fully expand the distal anchors 80 in the left ventricle 1080.

When the distal anchors 80 enter the left ventricle 1080, the distal anchors 80 can pass through the chordae 110 and move behind the mitral valve leaflets 108, thereby capturing the leaflets 108. In some embodiments, the distal anchors 80 and/or other parts of the prosthesis 1010 can push the chordae 110 and/or the mitral valve leaflets 108 outwards.

Thus, after release of the distal anchors 80, the delivery system 10 can then be repositioned as needed so that the ends of the left distal anchors 80 are at the same level of the free edge of the native mitral valve leaflets 108. The delivery system 10 can also be positioned to be coaxial to the mitral annulus 106 if possible while still reducing contact with the left ventricular wall, the left atrial wall, and/or the annulus 106.

In some embodiments, only the distal anchors 80 are released in the left atrium 1078 before the prosthesis 70 is move to a position within, or below, the annulus. In some alternate embodiments, the distal end of the prosthesis 70 can be further expanded in the left atrium 1078. Thus, instead of the distal anchors 80 flipping and no portion of the prosthesis 70 body expanding, a portion of the prosthesis 70 can be exposed and allowed to expand in the left atrium 1078. This partially exposed prosthesis 1010 can then be passed through the annulus 106 into the left ventricle 1080. Further, the proximal anchors, if any, can be exposed. In some embodiments, the entirety of the prosthesis 70 can be expanded within the left atrium 1078.

To facilitate passage through the annulus 106, the delivery system 10 can include a leader element (not shown) which passes through the annulus 106 prior to the prosthesis 70 passing through the annulus 106. For example, the leader element can include an expandable member, such as an expandable balloon, which can help maintain the shape, or expand, the annulus 106. The leader element can have a tapered or rounded shape (e.g., conical, frustoconical, semi-spherical) to facilitate positioning through and expansion of the annulus 106. In some embodiments, the delivery system 10 can include an engagement element (not shown) which can apply a force on the prosthesis 70 to force the prosthesis 70 through the annulus 106. For example, the engagement element can include an expandable member, such as an expandable balloon, positioned within or above the prosthesis 70.

In some embodiments, to facilitate passage through the annulus 106, a user can re-orient the prosthesis 70 prior to passing the prosthesis 70 through the annulus 106. For example, a user can re-orient the prosthesis 70 such that it passes through the annulus 106 sideways.

However, if only the distal anchors 80 are flipped, and no other expansion occurs, the prosthesis can be partially expanded in the ventricle 1080. Thus, when the prosthesis 70 is in the proper location, the distal end can be allowed to expand to capture the leaflets 108. If the distal end is already expanded, no more expansion may take place or the distal end can be further expanded.

Further, the PML, and AML 106 can be captured, for example by adjusting the depth and angle of the prosthesis 70. If a larger prosthesis diameter is needed to capture the leaflets 106, the outer sheath assembly 22 can be retracted until the desired diameter of the prosthesis 70 is achieved. Capture of the leaflets 106 can be confirmed through echo imaging. In some embodiments, a user can confirm that the prosthesis 70 is still in the appropriate depth and has not advanced into the left ventricle 1080. The position can be adjusted as needed.

In some embodiments, once the distal anchors 80 enter the left ventricle 1080 the system 10 can be pulled backwards (e.g., towards the left atrium 1078) to fully capture the leaflets 108. In some embodiments, the system 10 does not need to be pulled backwards to capture the leaflets 108. In some embodiments, systolic pressure can push the leaflets 108 upwards to be captured by the distal anchors 80. In some embodiments, systolic pressure can push the entire prosthesis 70 up towards the mitral annulus 106 after the leaflets 108 are captured and the prosthesis 70 is fully or partially released. In some embodiments, a user can rotate the delivery system 10 and/or prosthesis 70 prior to and/or while pulling the delivery system 10 backwards. In some instances, this can beneficially engage a greater number of chordae tendineae.

The outer sheath assembly 22 can be further retracted to fully expand the prosthesis. Once the prosthesis 70 is fully exposed, the delivery system 10 can be maneuvered to be coaxial and height relative to the mitral annulus 106, such as by flexing, translating, or rotating the delivery system 10. As needed, the prosthesis 70 can be repositioned to capture the free edge of the native mitral valve leaflets 108. Once full engagement of the leaflets 108 is confirmed, the prosthesis 70 can be set perpendicular (or generally perpendicular) to the mitral annular plane.

Following, the mid shaft assembly 21 can be withdrawn. The mid shaft assembly 21 can then be reversed in direction to relieve any tension on the delivery system 10.

Below is a discussion of proximal anchors 82, though some embodiments of the prosthesis 70 may not include them. In some embodiments, proximal anchors 82 may not be released from the system 10 until the distal anchors 80 have captured the leaflets 108. In some embodiments, proximal anchors 82 may be released from the system 10 prior to the distal anchors 80 capturing the leaflets 108. In some embodiments, the proximal anchors 82 can be released when the distal anchors 80 are super or intra annular and the expanded prosthesis 70 (either partially or fully expanded) can be translated through the mitral annulus 106. In some embodiments, the proximal anchors 82 could be released when the distal anchors 80 are sub-annular and the entire prosthesis 70 can be pulled up into the left atrium 1078 such that the proximal anchors 82 are supra-annular prior to release. In some embodiments, the proximal anchors 82 could be intra-annular prior to release and the systolic pressure could push the prosthesis 70 atrially such that the proximal anchors 82 end up supra-annular.

After, the leaflet capture and positioning of the prosthesis 70 can be confirmed, along with the relatively perpendicular position with respect to the mitral annular plane. In some embodiments, the nosecone 28 can then be withdrawn until it is within the prosthesis 70. The mid shaft assembly 21 can be further retracted until the prosthesis 70 is released from the delivery system 10. Proper positioning of the prosthesis 70 can be confirmed using TEE and fluoroscopic imaging.

Following, the delivery system 10 can be centralized within the prosthesis 70. The nosecone 28 and delivery system 10 can then be retracted into the left atrium 1078 and removed.

This intra-super annulus release can have a number of advantages. For example, this allows the distal anchors 82 to be properly aligned when contacting the chordae 110. If the distal anchors 82 were released in the left ventricle 1080, this could cause misalignment or damage to heart tissue, such as the leaflets 108 or chordae 110.

In an alternate delivery approach, the delivery system 10 can be translated into the left ventricle 1080 prior to release of the prosthesis 70. Thus, the distal end of the prosthesis 70, and thus the distal anchors 82, can be released and flipped partially, or fully within the left ventricle 1080. Accordingly, in some embodiments the anchors 70 can be released/flipped below the mitral annulus 106, just below the mitral annulus 106, and/or below the free edges of the leaflets 108. Further, the anchors 70 can be released above the papillary heads. Similar methodology as discussed above can then be used to properly position the prosthesis 70 and remove the delivery system 10 to deliver the prosthesis 1010. Further, in some embodiments the distal anchors 82 can be released without expanding the prosthesis initially in the ventricle 1080.

Torsional Pull Wire

Figure 30:
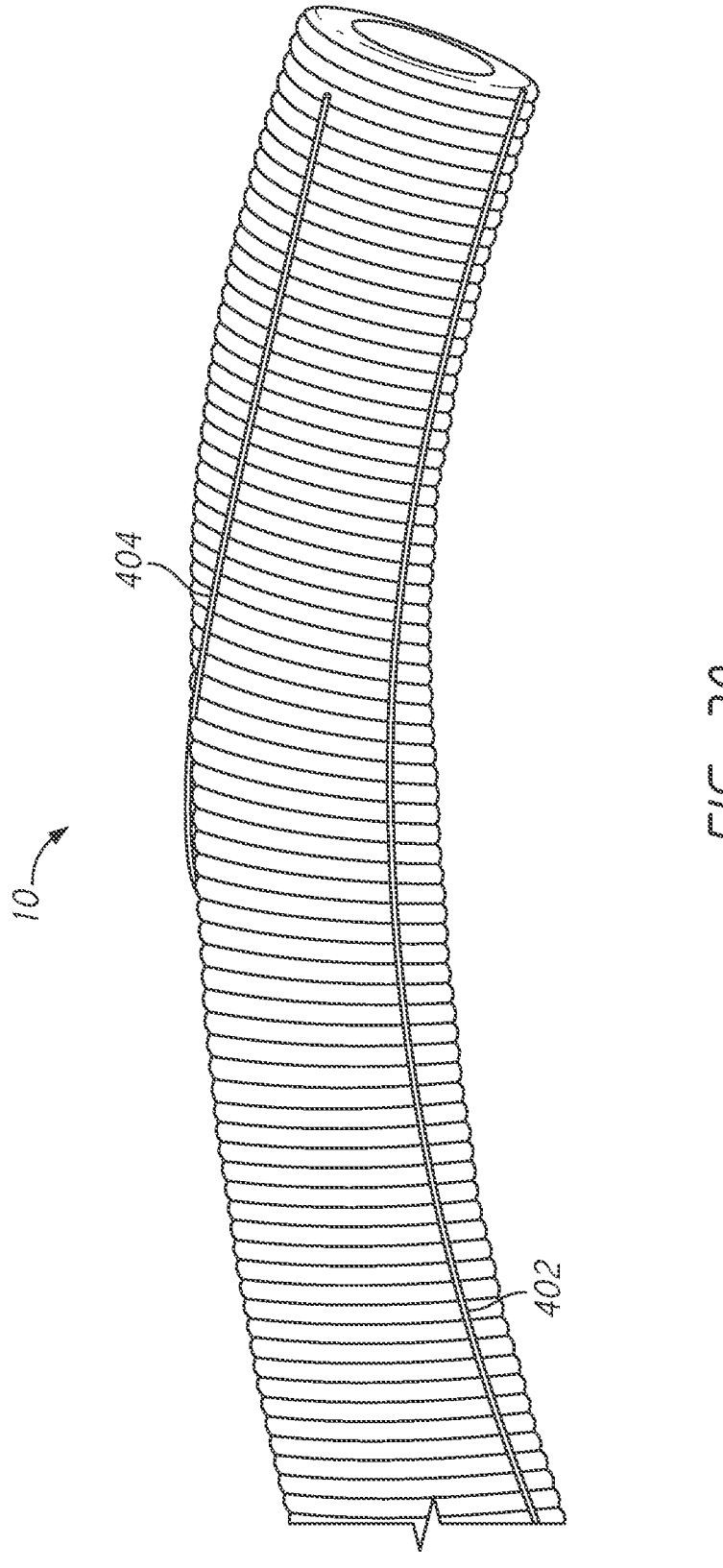
FIGS. 30-31 illustrate a torsional pull wire.
Figure 31:
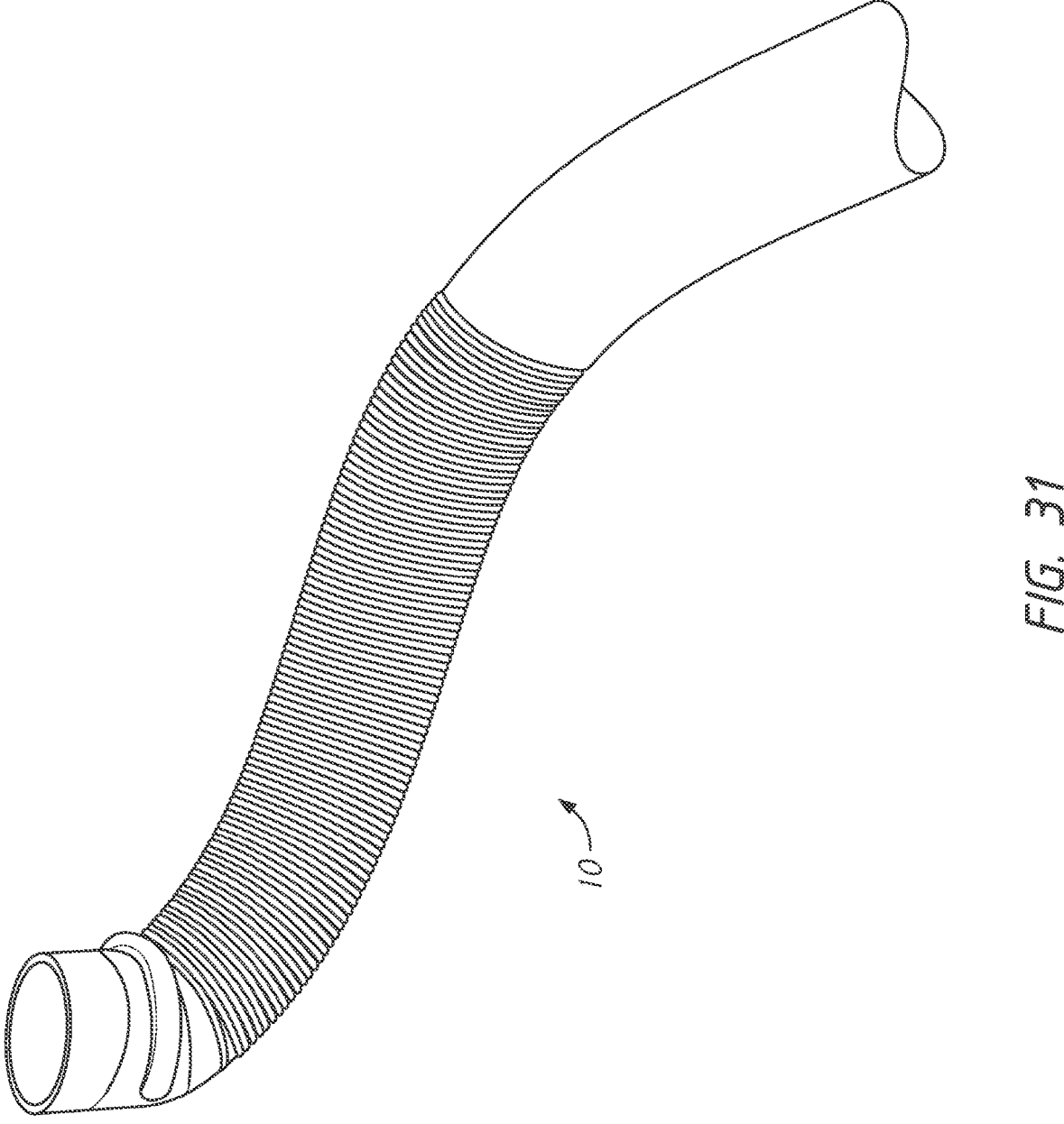

FIGS. 30-31 illustrate embodiments of a modified pull wire configuration that may be utilized with the delivery systems described herein or in other delivery systems. The pull wires may be attached to different assemblies, such as the outer sheath assembly 22, the inner assembly 18, or the rail assembly 20. While FIG. 30 shows the pull wires wrapped around an outer surface of a shaft, such as the rail 136, in some embodiments the pull wires can be located within a lumen of the shaft. Discussed above are embodiments of a delivery system 10 that can have multiple pull wires attached at different locations in order to provide multi-plane bending.

In some embodiments, two pull wires can be attached at two points at generally the same circumferential area, as shown in FIG. 30 (distal end towards the right). In some embodiments, a first pull wire 402 can extend directly along the delivery system 10 from the handle 14 to the distal end and attached to the rail hypotube 136. This wire 402 can create a single plane of deflection.

A second pull wire 404 can then be offset from the first section and wrapped around the outer diameter of the rail hypotube 136. In some embodiments, the second pull wire 404 can be approximately 45, 90, 135, etc. off-set from the first wire 402. The second wire 404 may wrap fully around the outer diameter, or may only partially wrap around the diameter, such as shown in FIG. 30. In some embodiments, the second wire 404 may extend straight for a portion of the tube, and then start to circumferentially curve around the tube. Thus, when forces are applied to the second wire 404, this creates a torsional force and thereby a twisting effect which provides for the second pulling plane. FIG. 31 illustrates the curve that can be achieved using the two pull wire embodiment. As shown, two bends can appear, allowing for maneuvering in a patient's vascular system.

In some embodiments, more than two pull wires can be used to create the curve shown in FIG. 31, including multiple straight and/or multiple curved wires.

Steerable Integrated Sheath

Figure 32:
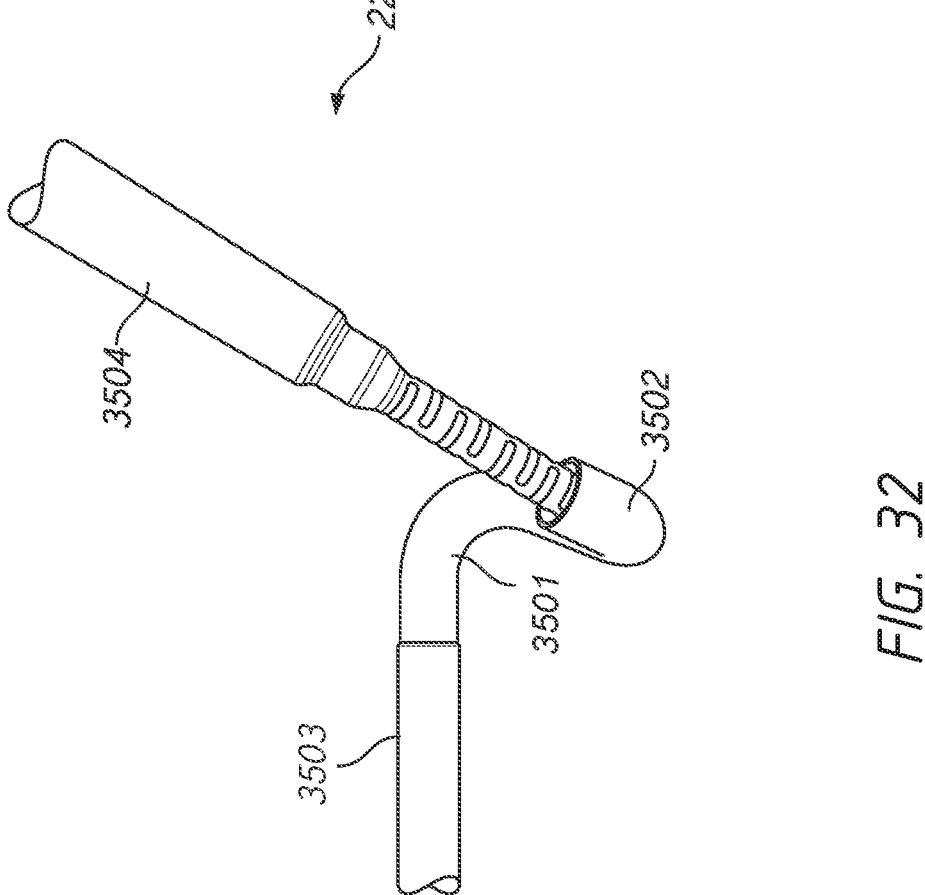
FIG. 32 illustrates an embodiment of a steerable integrated sheath.

In some embodiments, an integrated sheath can be used for steering of the delivery system 10 such as shown in FIG. 32. The integrated sheath 3502 can extend from the handle to radially surround the outer sheath assembly 22. This integrated sheath 3502 can be used in conjunction with, or as a replacement to, the rail assembly 20. FIG. 32 shows the integrated sheath 3502 located over the outer sheath assembly 22. In some embodiments, the distalmost bend of the integrated sheath 3502 can allow for at least 180 degrees of bending. In some embodiments, the proximalmost bend of the integrated sheath 3502 can allow for at least 90 degrees of bending. As discussed above, the proximalmost bend and the distalmost bend can be made independently or at the same time. In some embodiments, kinking/crushing/ovalization can be avoided during bending/deflection. In some embodiments, the integrated sheath 3502 can be atraumatic, especially for vessel structure.

The integrated sheath 3502 can extend distally so that its distal end is located proximal to the capsule 3504. It can be advantageous for the integrated sheath 3502 to extend as distally as possible for more precise steering. In some embodiments, the integrated sheath 3502 can cover the capsule 3504 during deployment, where it could then be retracted. In other embodiments, the integrated sheath 3502 can extend to approximately a proximalmost portion of the capsule 3504. In other embodiments, the integrated sheath 3502 can be spaced proximally from the capsule 3504. Thus, when the capsule 3504 is retracted to release the implant 70, it may impact the integrated sheath 3502, causing bending or changing the position of the integrated sheath 3502. In some embodiments, the integrated sheath 3502 can be formed of a flexible distal portion 3501 connected at a proximal end to a rigid proximal portion 3503.

The capsule 3504 can be formed from a collapsible material. This allows the collapsible capsule 3504 to be withdrawn into the integrated sheath 3502 upon retraction. In some embodiments, the collapsible capsule 3504 can include a flared distal section for potential recapture of the implant 70. In some embodiments, the collapsible capsule 3504 can be formed of material that can be collapsed, such as ePTFE, cloth, polymer, etc. In some embodiments, the collapsible capsule 3504 can taper in outer diameter from the distal end to the proximal end for withdrawing into the integrated sheath 3502. Thus, the integrated sheath 3502 can "swallow" the collapsible capsule 3504 upon retraction, allowing the steering to be as distal as possible.

Figure 33:
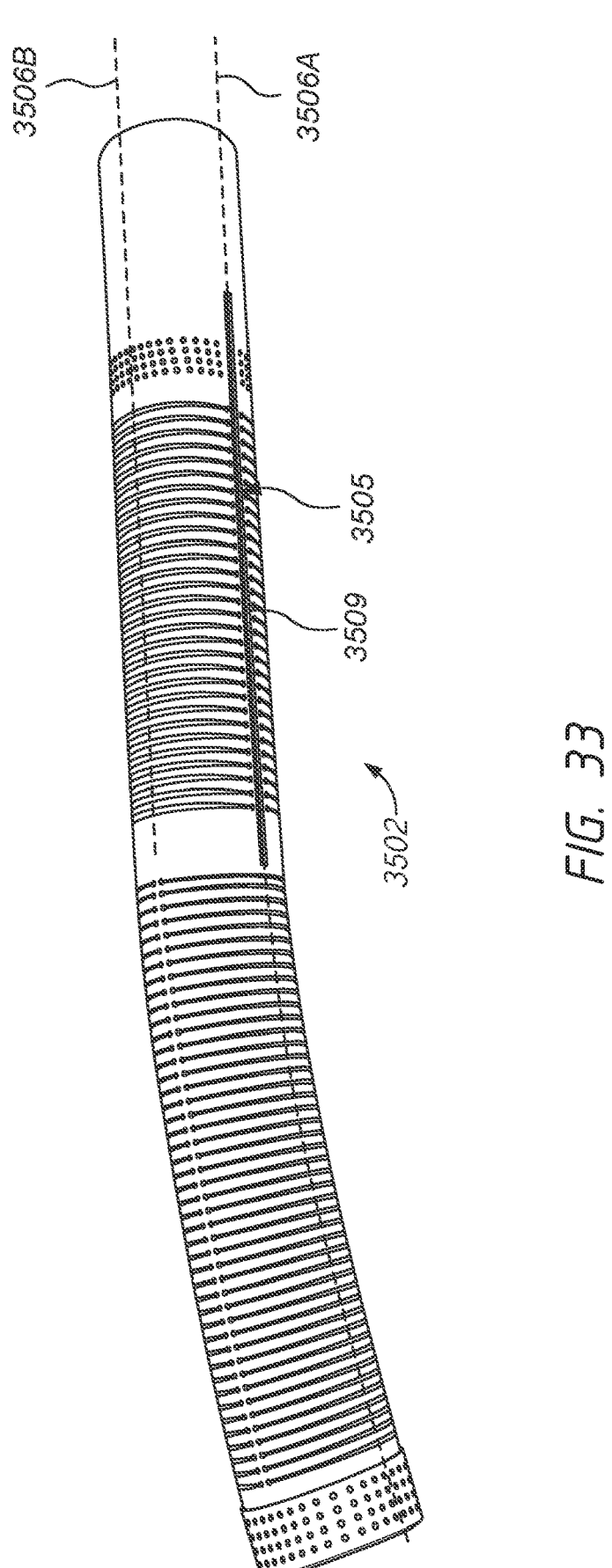
FIG. 33 illustrates an embodiment of a pull wire lumen.
Figures 34A, 34B, 34C:
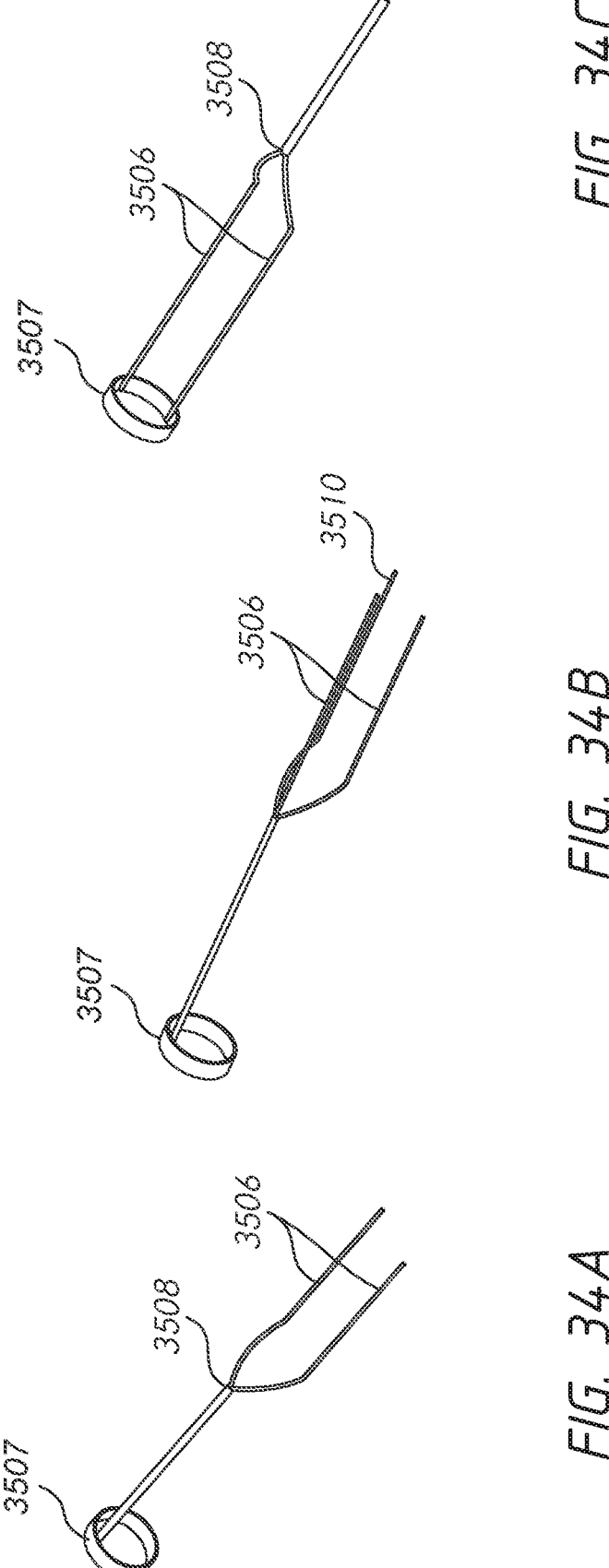
FIGS. 34A-C illustrate various pull wire configurations.

FIGS. 33-34C illustrate various configurations of the steerable integrated sheath 3502, which can be used with the above described delivery system 10 or in other delivery systems. Further, the solutions and pull wire configurations discussed below can be incorporated into the rail assembly 20.

In some embodiments, a "laser-cut solution", shown in FIG. 33 (distal end towards the left) can be used for steering the integrated sheath 3502. Similar to the rail 136 discussed above, the integrated sheath 3502 can be a lasercut hypotube having a number of cuts along its length and pull wires 3506 extending through. Slots can form a spine 3505 in the tube. However, the spine 3505 can be partially (or fully) cut out forming a channel, and a lumen 3509 can be attached into the cut out. The distal pull wire 3506A can then extend through the lumen 3509 and towards the distal end. The proximal pull wire 3506B remains within an inner lumen of the integrated sheath 3502. Accordingly, when the distal pull wire 3506A is pulled, it only affects the distal end of the integrated sheath 3502 and would not affect the proximal portion.

Alternatively, a different solution can be used which can steer the integrated sheath 3502. This can be a "polymer solution" as plastic/polymer/braid/coil materials can be used in conjunction with or instead of a metal lasercut hypotube. The polymer solution can utilize a number of different wire configurations that can achieve the bending. For example, FIG. 34A-C illustrates different wire configurations that can be used (distal end towards the left) in the integrated sheath 3502.

The first configuration shown in FIG. 34A includes a ring 3507 at the distal end of the integrated sheath 3502 (not shown). The configuration can include two wires 3506 extending down a length of the integrated sheath 3502 spaced apart approximately 180 degrees. They can then meet together approximately midway 3508 through the integrated sheath 3502 and extend to the distal ring 3507. Accordingly, pulling both wires 3506 gives a single plane bend (bent towards the top in FIG. 34A). If either of the wires 3506 are relaxed, the integrated sheath 3502 will bend in the direction of the wire still under tension at a proximal section, and thus the integrated sheath 3502 can bend in both directions. In some embodiments, the wires 3506 can be connected for about 40 mm from the ring 3507, can separate away from each other for about 10 mm, and can separately extend for 20 mm or more to connect to the handle 14.

For FIG. 34B, this is generally the same configuration as FIG. 34A, but a third wire 3510, extending approximately 90 degrees (or about mid-way) between the two offset wires 3506. The third wire 3510 can connect with the other two wires 3506 when they come together. This will achieve generally the same performance as FIG. 34A, but the extra wire 3510 will provide more strength and resolution. In some embodiments, the wires 3506 can be connected for about 40 mm from the ring 3507, can separate away from each other for about 10 mm, and can separately extend for 20 mm or more to connect to the handle 14. Thus, the third wire 3510 may extend 30 mm or more to the handle 14.

FIG. 34C has a configuration generally the opposite of FIG. 34A. More specifically, the two wires 3506 extend together on the proximal end and then split apart 3508 to approximately 180 degrees separated at the distal end to attach to the ring 3507. Accordingly, pulling both wires still causes an upward bend, but relaxing one wire creates a distal bend instead of the proximal bend of FIG. 34A. In some embodiments, the wires 3506 can be separated for about 40 mm from the ring 3507, can connect towards each other for about 10 mm, and can connectedly extend for 20 mm or more to connect to the handle 14.

Axial Runners

In some embodiments, it can be advantageous for a delivery system to use a flexible shaft with a number of wires which can act as axial runners as shown in FIG. 35-C. The wires can extend through separate lumens in the shaft as shown in the figure. The shaft can be any of the shafts discussed herein, such as in the outer sheath assembly 22, the rail assembly 20, the inner assembly 18, or the integrated sheath 3502.

Figures 35A, 35B, 35C:
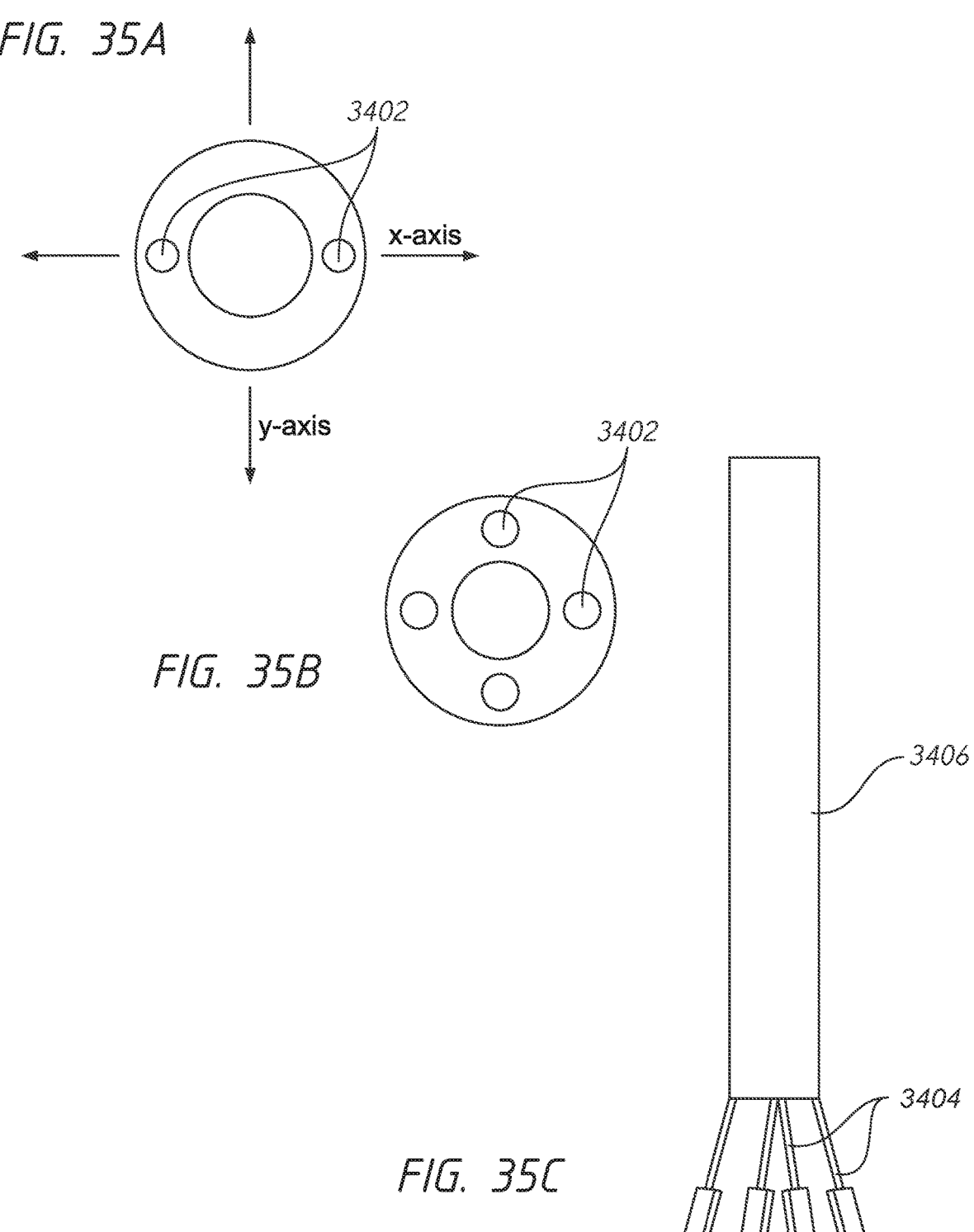
FIGS. 35A-C illustrates embodiments of axial runners.

In order to achieve improved tensile strength in a shaft, one or more wires can be used. The drawback of adding spines or runners to a shaft, as done previously, is that they create a directional bias. Sometimes the bias is so extreme that the shaft is practically incapable of bending in one or more directions. For example, two axial runners 3402 arranged as shown in FIG. 35A will only be able to bend along the y-axis and not the x-axis. If bent on the y-axis, the runners 3402 are taking the same curve and flexibility is unhindered. However, if bent on the x-axis, the runner on the inner curve and the runner on the outer curve have different arc lengths, causing them to lock up on each other. Further, adding four large axial runners, shown in FIG. 35B, causes the shaft to lose most of its flexibility.

However, if the wires were not terminated on the proximal end but allowed to float within their lumens, the shaft would retain its flexibility, as shown in FIG. 35C. Accordingly, embodiments of the disclosure allow for floating wires within lumens of one of the shafts of the delivery system 10. The wires 3404 can extend along a length of the shaft 3406 and exit the proximal and distal ends of the shaft 3406. The wires 3404 can be permanently affixed in the handle 14, such as at a knob, or can be hand tensioned. In some embodiments, four axial wires can be used (separated by 90 degrees or about 90 degrees), though other numbers of wires, such as 1, 2, 3, 4, 5, 6, 7, or 8 wires, and positioning can be used as well.

The wires 3404 can be configured to have two configurations, free floating and tensioned, which can be operated at the handle 14. When free floating, the wires 3404 have no tension in them. Thus, the shaft 3406 can be configured to bend in any direction as needed, and thus can have "universal flexibility". However, when the wires 3404 are placed under tension (or locked), they force the shaft 3406 into a straight rigid configuration along that wire with the wires bearing the load, allowing for high ultimate tensile strength. In some embodiments, each of the wires 3404 can be individually tensioned and released, or multiple wires 3404 can be tensioned and released at the same time.

It will be understood that steering (and thus bending) the shaft 3406 would cause the relative distance from handle 14 to the distal end of the shaft to change depending on the direction and magnitude of the bend. If the shaft 3406 is pulled in tension with the wires, the force will translate through the wires 3404 instead of purely the shaft 3406. As a result, this will create a tensile strength similar to standard axial runners with significantly less elongation than one would see with just the shaft. Additionally, the shaft 3406 would exhibit similar flexibility to a shaft with no axial runners when the wires 3404 were free floating. Accordingly, embodiments of the flexible axial wires/runners would provide an advantageous way to have universal flexibility with great tensile strength.

Capsule with Spring Pattern

It can be advantageous for the capsule 106 to be both flexible and resistant to compression during use of the delivery system 10. For example, flexibility can allow the capsule 106 to retract back over the delivery system 10 curvature while deploying the prosthesis 70, and the compression resistance can allow for controlled deployment of the prosthesis 70 and the potential to reposition or recapture the prosthesis 70. Embodiments of the disclosure describe a capsule 106 which has both the flexibility and compression resistance.

FIGS. 36-39 illustrate an embodiment of a capsule 106 construction that can be used with embodiments of the disclosure. The covering material of the capsule 106 can be the same as described above. In some embodiments, as shown, the capsule 106 can have a generally spiral (e.g., coil, revolving) backbone(s)/spine(s) extending a longitudinal length, or a partial longitudinal length, of the capsule 106. In some embodiments, the capsule 106 can be made of a number of attached separate rings having the below-described features. In some embodiments, the capsule 106 can have thicker/stronger sections at its ends in order to provide additional support to the prosthesis 70 during deployment. Embodiments of the capsule 106 can be a metal, polymer, or ceramic and the particular material does not limit the disclosure. In some embodiments, the capsule 106 can be laser cut to form the below-discussed design.

Figure 36:
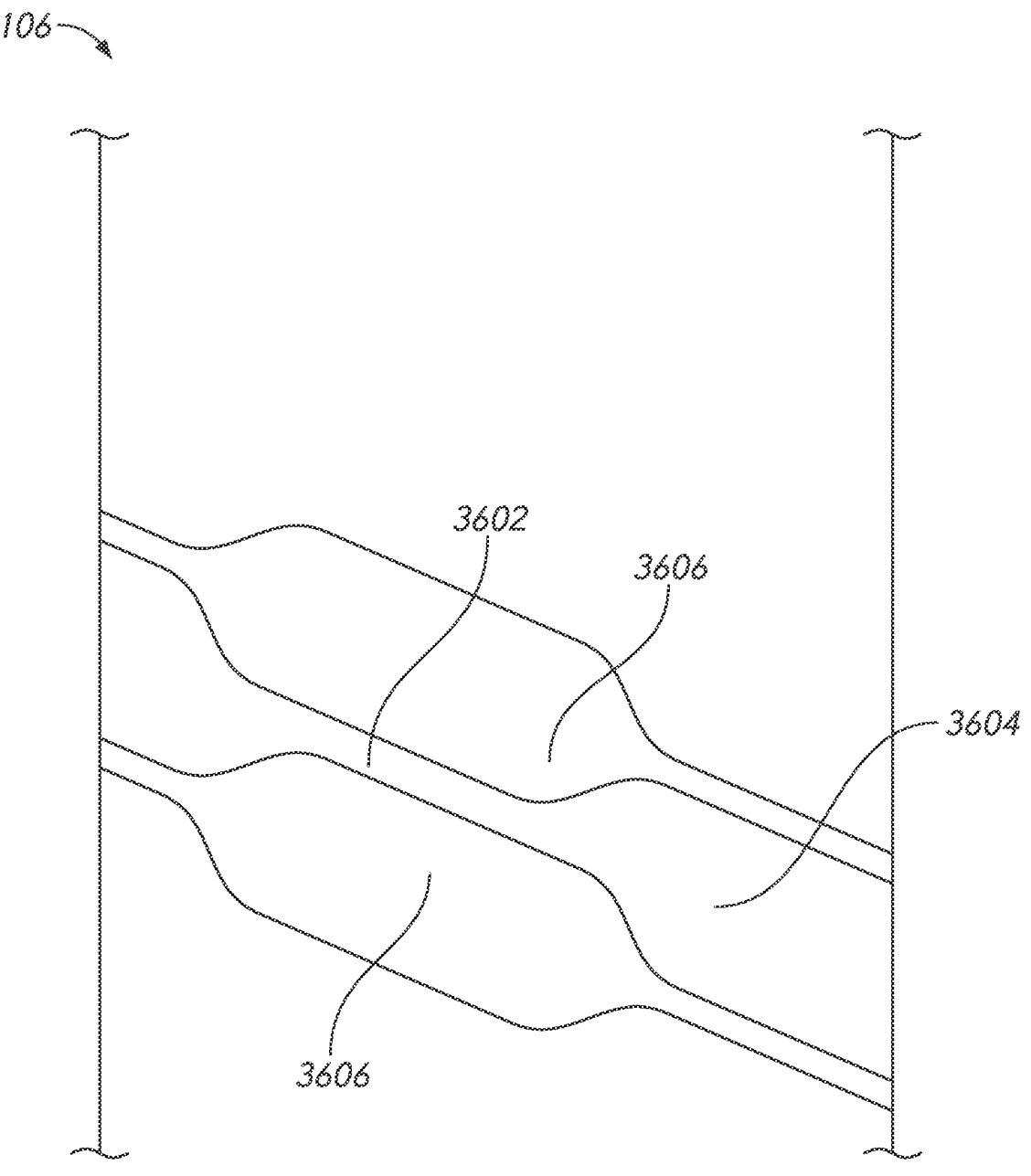
FIGS. 36-39 illustrate embodiments of a capsule having improved flexibility and compression resistance.

FIG. 36 illustrates a two-dimensional view of a cut pattern of the capsule 106. As shown, the capsule can contain a thin portion 3602 and a thick portion 3604 formed by the cut pattern (e.g., empty spaces or gaps with no material) 3606. In some embodiments, the thick portion 3604 can have a thickness of 1.5, 2.0, 2.5, 3.0, 3.5, or 4.0 (or about 1.5, about 2.0, about 2.5, about 3.0, about 3.5, or about 4.0) times the thickness of the thin portion 3602. In some embodiments, the thick portion 3604 can have a thickness of greater than 1.5, 2.0, 2.5, 3.0, 3.5, or 4.0 (or greater than about 1.5, about 2.0, about 2.5, about 3.0, about 3.5, or about 4.0) times the thickness of the thin portion 3602. In some embodiments, the thick portion 3604 can have a thickness of less than 1.5, 2.0, 2.5, 3.0, 3.5, or 4.0 (or less than about 1.5, about 2.0, about 2.5, about 3.0, about 3.5, or about 4.0) times the thickness of the thin portion 3602. However, the particular thickness is not limiting.

Figure 37:
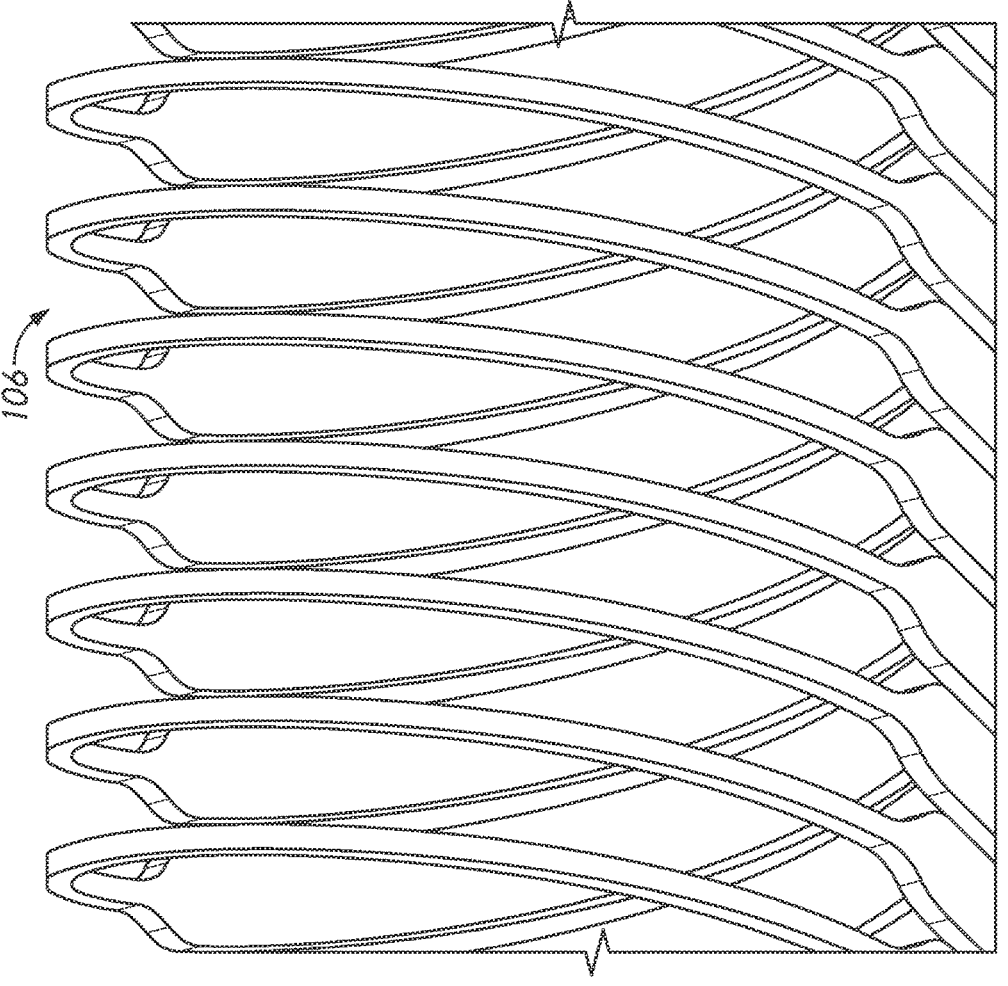
Figure 38:
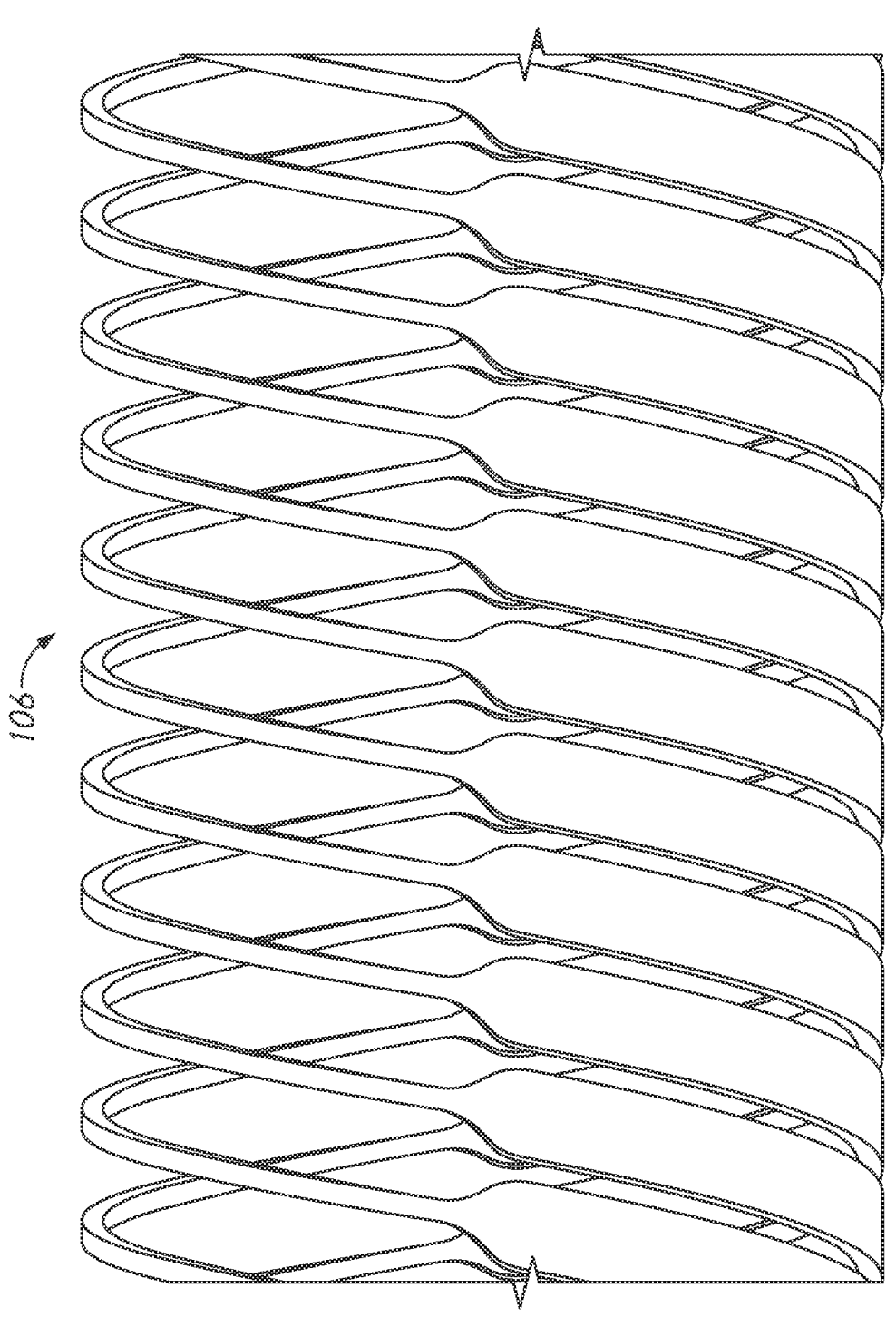

FIGS. 37-38 show a three dimensional view of the capsule 106. As shown, the backbone of the material can spiral between the proximal and distal ends with repeating patterns of thick portions 3604 and thin portions 3602, thereby forming a tube shape with a lumen running through it. Thus, every "rotation" around the capsule 106 can contain one thick portion 3604 and one thin portion 3602. In some embodiments, the capsule 106 can be designed such that for each ring of the spiral/coil (e.g., each approximately 360°), part of the spiral is a thin portion 3602 and part of the spiral is a thick portion 3604. In some embodiments, greater or less than 360° can include both the thin portion 3602 and the thick portion 3604. In some embodiments, multiple thin portions 3602 and thick portions 3604 can be used in a single turn to provide further bending axes.

In some embodiments, all of the thick portions 3604 can be circumferentially aligned throughout a length of the capsule 106, such as shown in FIG. 38. Thus, there is more space between longitudinally adjacent thin portions 3602 than between longitudinally adjacent thick portions 3604, allowing for more flexibility in the thin portions 3602. In some embodiments, the thick portions 3604 can change alignment from the distal to the proximal end.

In some embodiments, for each full rotation (e.g., 360 degrees), approximately half can be thick portion 3604 and half can be thin portion 3602. In some embodiments, for each full rotation (e.g., 180 degrees), greater than half can be thick portion 3604. In some embodiments, for each full rotation (e.g., 180 degrees), less than half can be thick portion 3604. In some embodiments, for each full rotation (e.g., 180 degrees), greater than half can be thin portion 3602. In some embodiments, for each full rotation (e.g., 180 degrees), less than half can be thin portion 3602. The capsule 106 can be modified to provide a desired bending pattern.

Figure 39:
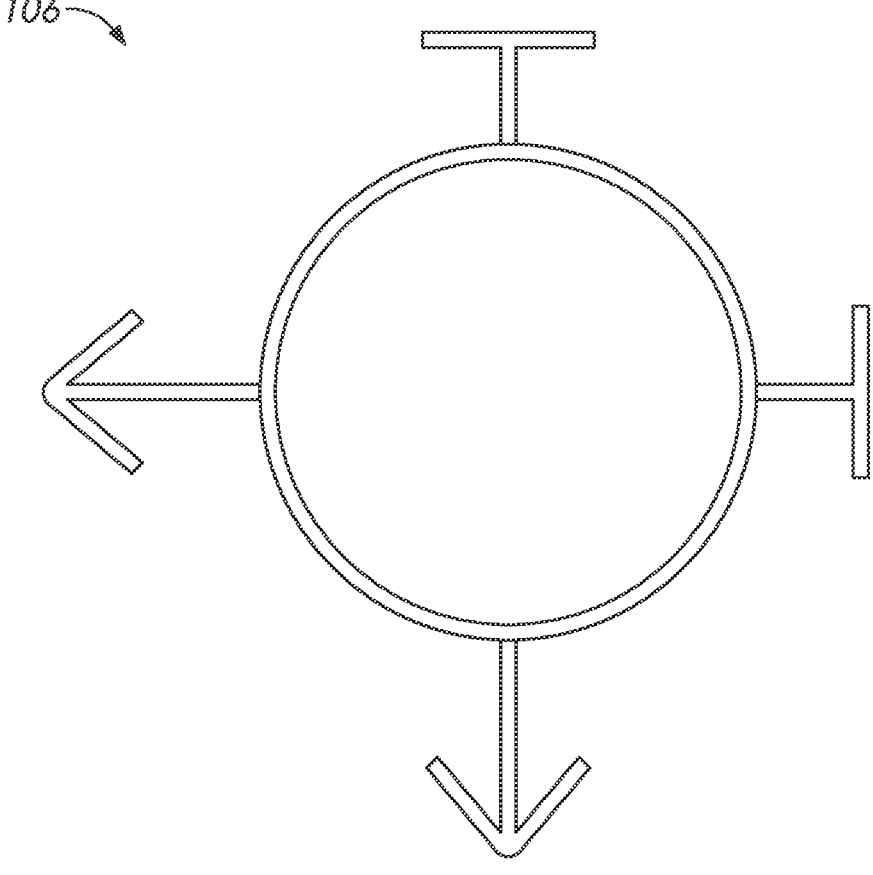

The particular design of the capsule 106 disclosed herein can, in particular, allow for forward flexibility in two planes (in particular bending along the thin portion 3602). Further, the capsule 106 can bottom out when flexed backwards or under compression, due to the adjacent thick portions 3604. In this way, the coil can achieve the flexibility and compression requirements. This is generally illustrated in FIG. 39, where the capsule 106 can have greater bending in the direction of the thin portions 3602 (shown by the arrows) and less bending ability in the thick sections 3604 (shown by the blocked lines). With this design, the capsule 106 can bend towards the thin portions 3602 uninhibited, but the thick portions 3604 bottom out under compression. In this way, the capsule 106 achieves the flexibility and compression requirements. Thus, the capsule 106 can achieve uniform, intra-ring pitch variation, allowing flexibility in two planes while maintaining compression resistance. In some embodiments, the capsule 106 can have additional degrees of freedom, such as along 1, 2, 3, 4, 5, or 6 planes of freedom, but adding further thin portions 3602. In some embodiments, the capsule 106 can bend at a particular angle or curvature by varying the location of the thin portions 3602.

Capsule with Laser Cut Pattern for Reducing Bend Strain

Disclosed herein are embodiments of a capsule 106 with a particular cut/slot pattern that can have reduced recoiling. Further, the cut configuration can allow for improved amount of flex cycles. Embodiments of the disclosed capsule 106 can include features in conjunction with those discussed above. The configuration discussed herein can also apply to hypotube 104, or other components/shafts in the disclosed delivery system 10.

Figure 40:
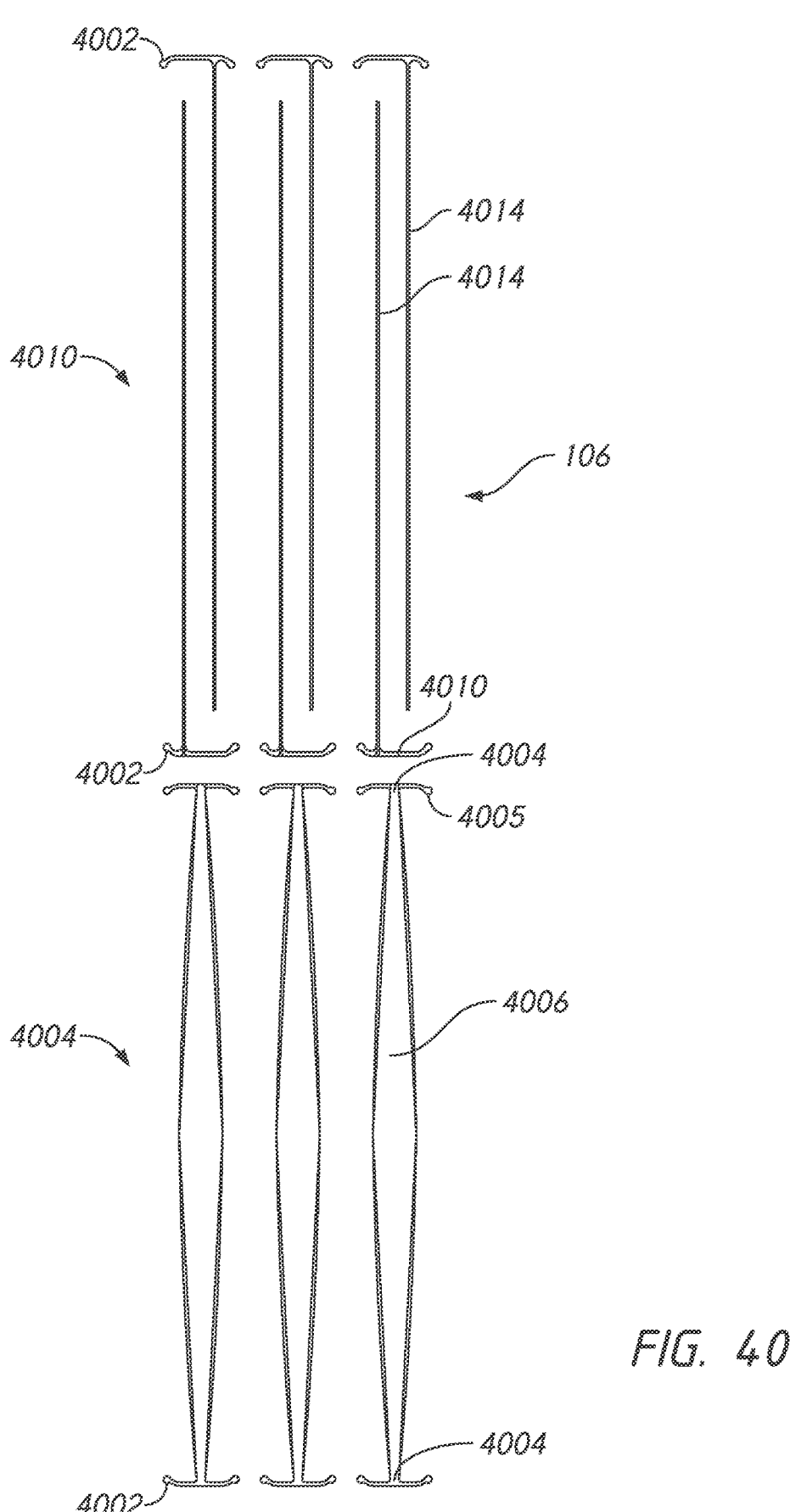
FIG. 40 illustrates a flat cut pattern of an embodiment of a capsule with improved recoiling.
Figure 41:
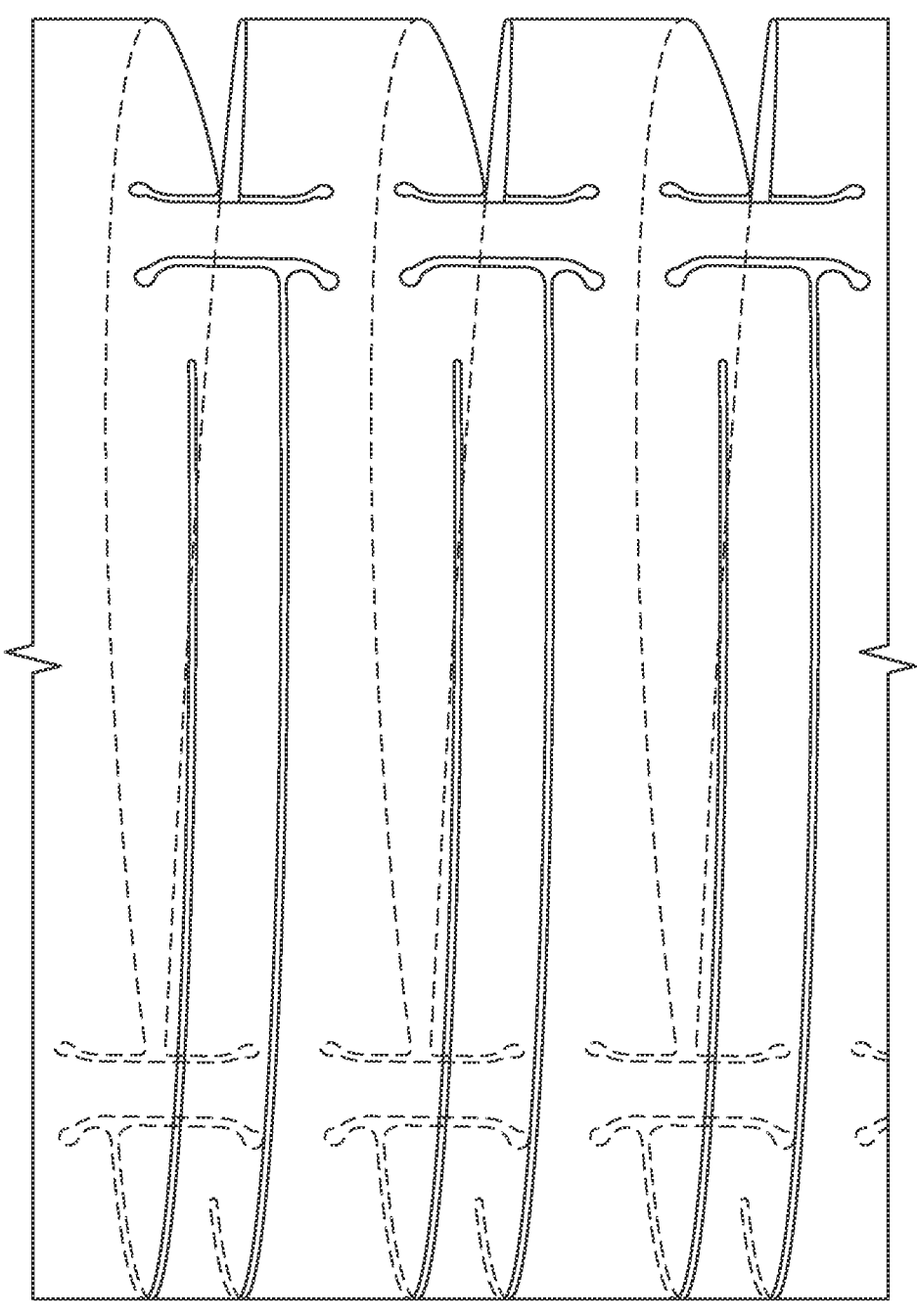
FIG. 41 illustrates an embodiment of a capsule with improved recoiling.

FIGS. 40 and 41 illustrate an embodiment of a cut pattern on a capsule 106, with FIG. 40 showing the flat pattern and FIG. 41 illustrating the pattern in a tube. In some embodiments, the cut pattern can minimize strain while retaining a tight bend radius and tubing sizing, while preventing binding of any outer layer, such as a polymer later, on the edges. In some embodiments, the capsule 106 can be bent into a small radius with a large tubing while also recoiling back to its original straight configuration (for example, 0.5" radius and 180° bending with 0.246" outer diameter tubing). Thus, plastic deformation during bending can be minimized.

As shown in FIG. 40, a "half-spring" dual-spine cut pattern can effectively distribute strain away from the spines. The spines 4002 can be approximately spaced 180° apart, though this positioning is not limiting and can be adjusted with respect to one another. Further, more spines can be included, and the number of spines is not limiting. As shown, the capsule 106 can have two different cut patterns, each cut pattern located circumferentially between the spines 4002. The first cut pattern is an open cut pattern 4004 and the second cut pattern is a spring cut pattern 4010, thus forming the "half-spring" dual-spine.

The open cut pattern 4004 includes a pair of arc cuts 4004 located circumferentially spaced away between the spines 4002. In some embodiments the arc cuts 4004 can be generally circumferentially adjacent to the spines 4002. The arc cuts 4004 can have their openings facing towards one another as shown in FIG. 40. In some embodiments, the arc cuts 4004 can include enlarged end portions 4005.

Between and connecting the arc cuts 4004 is a slot/cut/ opening 4006. The slot 4006 can vary in longitudinal thickness between the arc cuts 4004. In some embodiments, the slot 4006 can be thinnest near the arc cuts 4004 and be longitudinally thickest at the midpoint between the arc cuts 4004. In some embodiments, the thickest dimension of the slot 4006 is approximately 1.1, 1.3, 1.5, 1.7, 2.0, 2.5, or 3.0 times the thickness of the thinnest portion of the slot 4006. In some embodiments, the thickest dimension of the slot 4006 is greater than 1.1, 1.3, 1.5, 1.7, 2.0, 2.5, or 3.0 times the thickness of the thinnest portion of the slot 4006. In some embodiments, the thickest dimension of the slot 4006 is less than 1.3, 1.5, 1.7, 2.0, 2.5, or 3.0 times the thickness of the thinnest portion of the slot 4006. In some embodiment, the slot 4006 can be formed of generally curved lines, and thus having two elongated arc cuts facing to form the slot. In some embodiments, the slot 4006 can be formed of generally straight lines.

The spring cut pattern 4010 can also include two arc cuts 4012 spaced circumferentially apart, similar to that discussed above. However, instead of being connected by the slot 4006, the arc cuts 4012 are not connected to one another. Each pair of arc cuts 4012 includes a pair of circumferentially extending cuts 4014 spaced longitudinally apart. Each cut 4014 extends in the opposite direction from the arc cut 4012. The cut 4014 can extend at least 70%, 75%, 80%, 85%, 90%, or 95% of the circumferentially distance between the pair of arc cuts 4012. Further, each cut 4014 can extend from the arc cut 4012 spaced apart from the midpoint, such as approximately 15, 25, or 30% from an end the arc cut 4012, thereby preventing overlap of the cuts 4014 and keeping them longitudinally spaced apart. In some embodiments, the cuts 4014 are generally line cuts and do not change longitudinal thickness.

Figure 42:
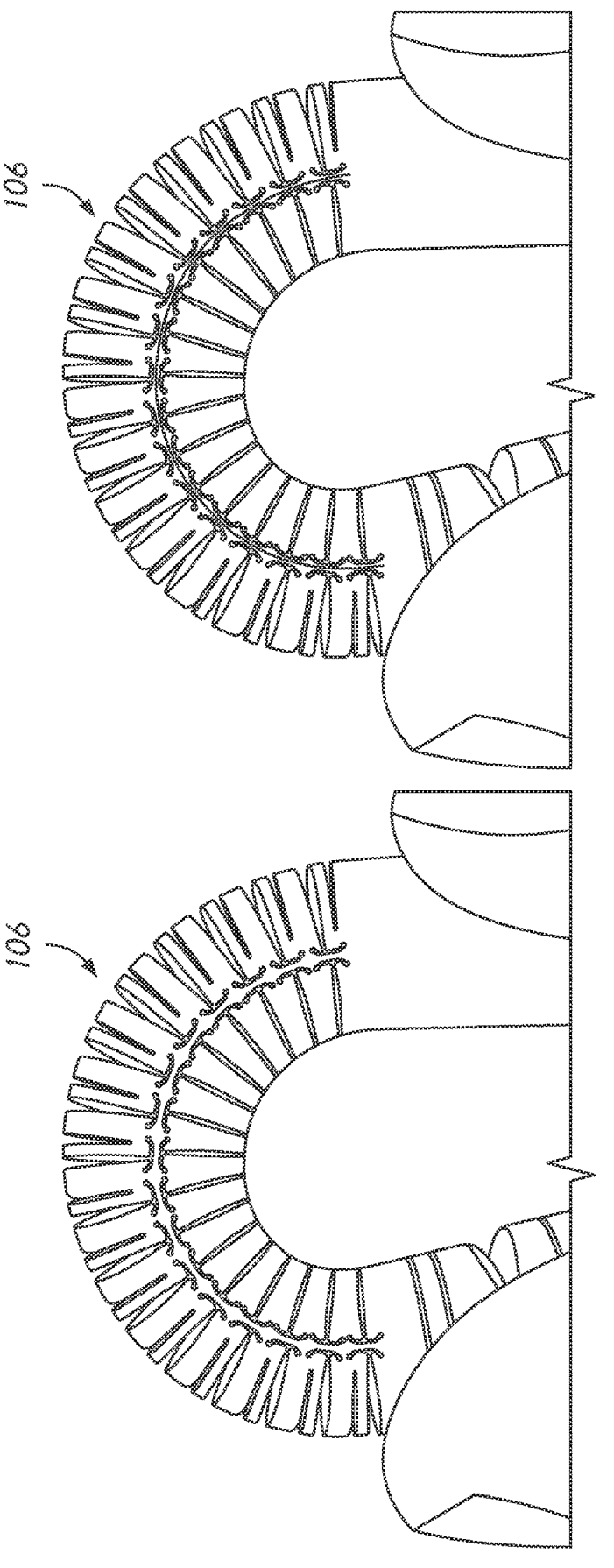
FIGS. 42-44 illustrate embodiments of a capsule with improved recoiling.
Figure 43:
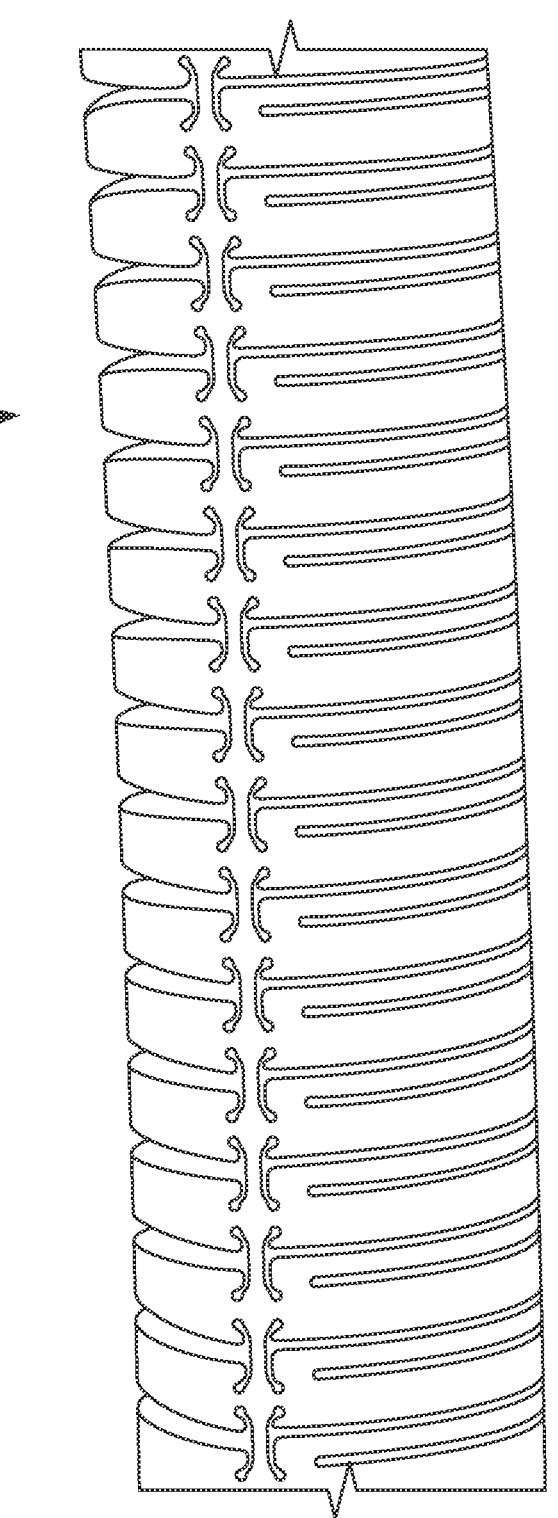
Figure 44:
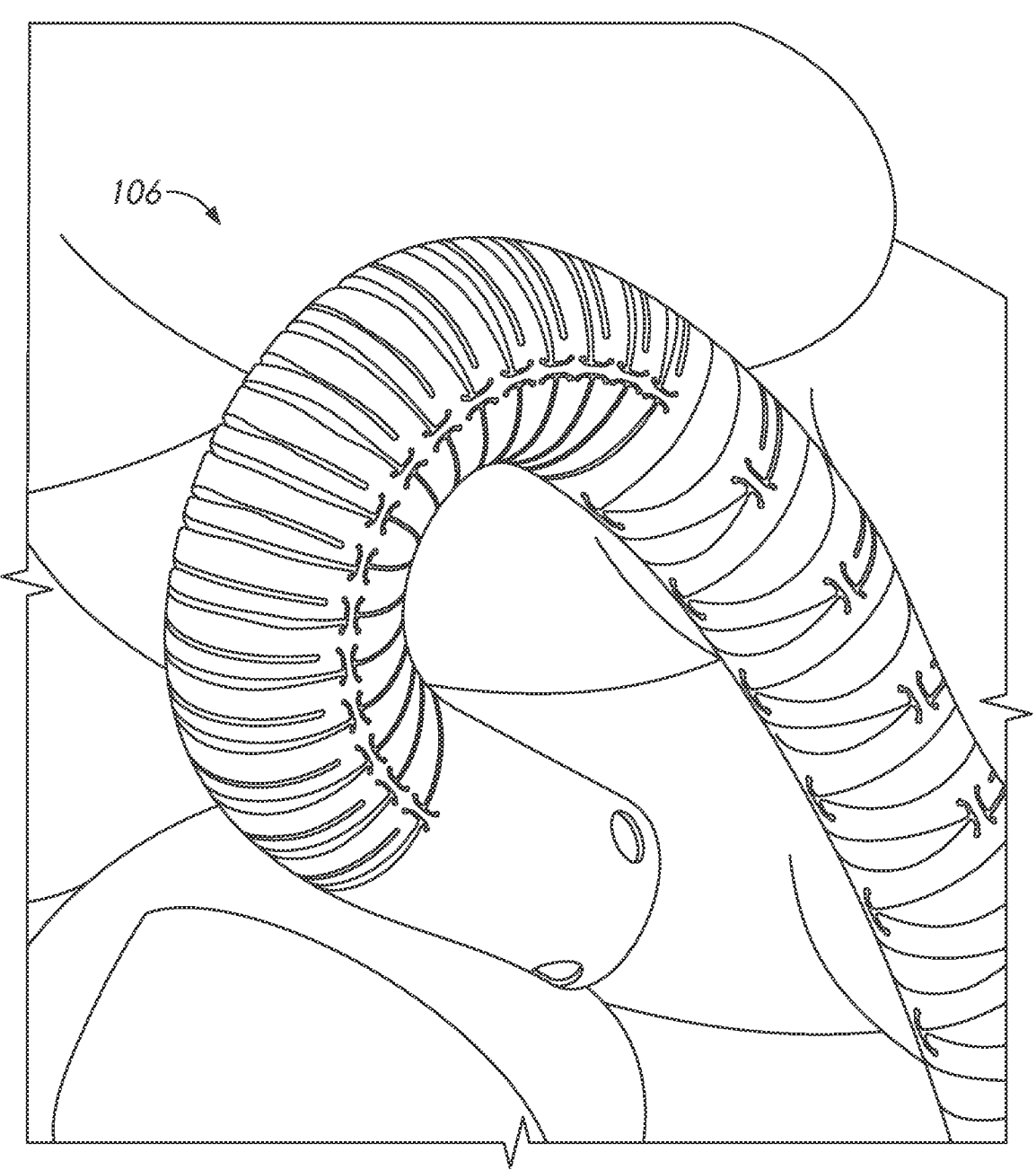

FIG. 41 illustrates the capsule 106 in bending action. As shown, strain can be distributed from the spine 4002 into the spring cut pattern 4010. Further, bending of the capsule 106 allows the different cuts to open up to allow for bending. FIGS. 42 and 43 illustrate the spine in the unbent (FIG. 42) and bent (FIG. 43) configuration.

The cut pattern discussed above can distribute part of the strain on the spines to the material between the cut and the strain relief. In this way, the strain is effectively distributed, reducing plastic deformation even at extreme bend radii and increasing recoil force. In addition, the spring element partially fills the open cut, reducing the chance of an outer layer binding on the cut edge.

Shaft/Tube Reflow Prevention Layer

In some embodiments, manufacture of the delivery system 10 can encounter a situation wherein an outer "jacket" layer covering the hypotube 104 (or any of the other tubes), such as a polymer/rubber/plastic coating, flows onto and around the interior reinforced layer, thereby reducing flexibility. In particular, the jacket layer can flow into gaps/slots/cuts/braids, limiting flexibility. This can be particularly problematic in the outer hypotube 104, though it can affect other components/shafts/tubes as well and the particular component is not limiting. Embodiments of the disclosure can avoid such an issue by including an additional layer into the delivery system 10.

In some embodiments, a high melting temperature and/or a high flexibility polymer layer can be added above the typical shaft reinforcement layer but below the typical outer jacket layer. This additional layer can prevent the outer jacket material from flowing into typical shaft reinforcement layers (braid, coil, axial runners, pull wires, etc.) during typical shaft reflow processing, which significantly increases shaft flexibility while maintaining standard reinforced shaft performance features. In some embodiments, a smooth outer diameter (e.g., polymer material) can be maintained.

Figure 45A:
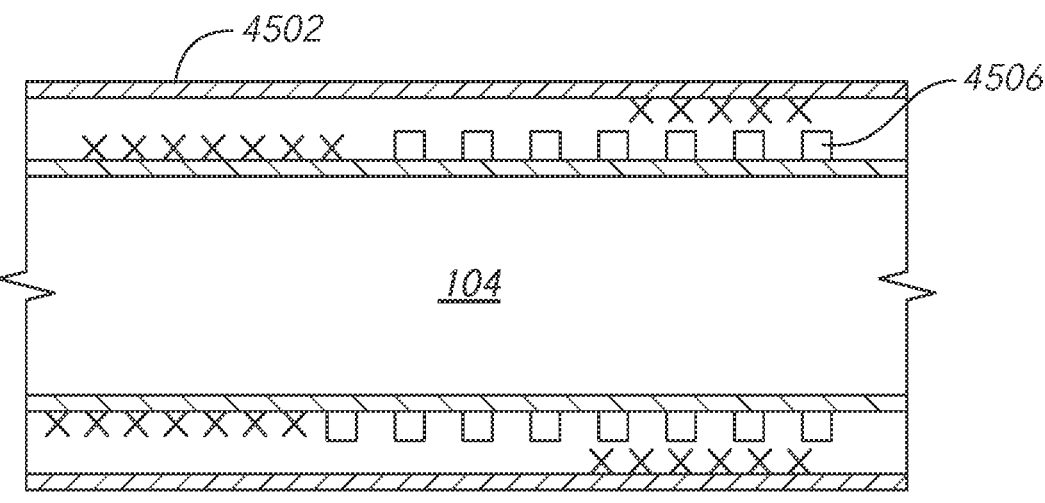
FIG. 45A illustrates a standard hypotube construction.

FIG. 45A illustrates a standard reinforced shaft construction. As shown, the polymer jacket (e.g., outer layer) 4502 is constrained and melted onto the reinforced inner layer 4506, such as hypotube 104. However, this can significantly reduce shaft flexibility, leading to breakage of certain components during use.

Figure 45B:
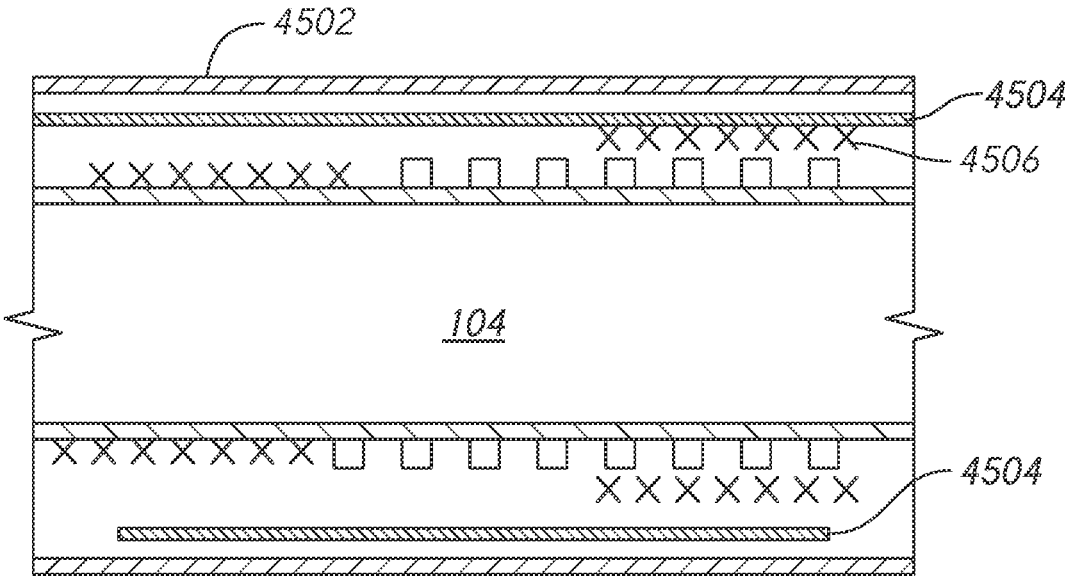
FIG. 45B illustrates an improved hypotube construction including an additional high temperature polymer layer.

FIG. 45B illustrate a reinforced shaft with reflow prevention layer as described herein. Accordingly, an additional layer 4504 can be located radially on top of the outer hypotube 104 and/or reinforced inner layer 4506, whether the braid, laser cut, or combination of the two discussed above, but below the jacket layer 4502. This feature can be used on any of the shafts discussed herein, including the capsule 106. In some embodiments, a PTFE tape reflow prevention layer 4504 can be used for high melting temperature, low surface friction, ultra-thin, and high flexibility. The additional layer 4504 material can be PTFE, ePTFE, or other high melting temperature polymer, such as having a melting temperature greater than 100, 110, 120, 130, 140, or 150° C., and the particular material is not limiting. In some embodiments, the reflow prevention layer 4504 may be shorter than the hypotube 104/capsule 106/jacket 4502 length, or whichever tube/portion is being covered. In some embodiments, the reflow prevention layer 4504 may be greater than the hypotube 104/capsule 106/jacket 4502 length. In some embodiments, the reflow prevention layer 4504 may be the same longitudinal length as the hypotube 104/capsule 106/jacket 4502 length. The reflow prevention layer 4505 can advantageously prevent the outer jacket material 4502 from flowing onto and/or around the interior reinforced layer and components 4506 (e.g., braid, coil, axial runners, pull wires).

Alternative Valve Attachment Mechanism

Disclosed herein are prosthesis attachment mechanisms that can be incorporated into the above. In some embodiments, multiple of the disclosed can be incorporated into the delivery system 10. In some embodiments, certain components disclosed herein can be incorporated.

As discussed above, in some embodiments the delivery system 10 can include an inner retention member 40, an outer retention member 42, and an outer capsule 106 to attach the prosthesis 70 to the delivery system 10. In some variations, it can be advantageous to remove the outer retention member 42 and/or the mid shaft 43 to conserve space.

For example, FIG. 46A illustrates an embodiment where an oversizing of the inner retention member 40 can be used in conjunction with the outer capsule 106 to retain the prosthesis 70 during deployment.

In some embodiments, the standard inner retention member 40 discussed above can be used. However, an additional material can then coat/overmold/cover the inner retention member 40 to increase the radial thickness of the inner retention member 40. This can allow an outer radius of the expanded inner retention member 40 to be close to or in contact with a radially inner surface of the capsule 42.

In some embodiments, this modification can be achieved through machining or dip-coating the inner retention member 40 in a softer material 4602 in order to provide a better locking seal against the capsule. Examples of a softer material are a soft rubber or plastic, such as for a polymer overmold. Some examples of softer material are silicone, EPDM, or Pebax®. The soft material 4602 can cover a portion of or all of the inner retention member 40. In some embodiments, the soft material 4602 can only cover the radial outer surface of the inner retention member 40. The soft material 4602 can be configured to still allow the capsule 106 and inner retention member 40 to translate with respect to one another. Thus, the softer material could interfere and compress with the capsule 106 causing increased friction. In some embodiments, the capsule 106 can have an inner surface with the softer material, and the inner retention member 40 may be made of a harder plastic, and or may be oversized.

Additionally, though not required, the capsule 106 can be reinforced to provide further strengthening against the radially expanding force of the prosthesis 70. In some embodiments, a distal end of the capsule 106 can include a reinforcing material. For example, a ring 4604 formed of a stronger material than the capsule 106 can be added on the distal end of the capsule 106. This ring 4604 can be added onto the distal end of the capsule 106. In some embodiments, the ring 4604 is attached radially inward of the capsule 106 so that the capsule 106 is not further distally extended. In some embodiments, the ring 4604 is attached radially outward of the capsule 106. The ring 4604 can be made of metal, hard plastic, or other material to strengthen the capsule 106. The ring 4604 can be used to stage deployment of the prosthesis 70, depending on the location and interference during use.

In some embodiments, an additional spine 4606 can be used instead of or in conjunction with the above. As shown in FIG. 46A, the spine 4606 can extend along a portion or all of the longitudinal length of the capsule 106. In some embodiments, multiple spines 4606 can be used. The spine 4606 can be lasercut in some embodiments. In some embodiments, the spine 4606 can be fluorinated ethylene propylene, metal, or other stiff material, and the particular material is not limiting. In some embodiments, the capsule 106 can include a number of rings 4608 extending around a circumference of the capsule 106. They can be made of similar or different material than the spine 4606. The rings 4608 and spine 4606 can be used with each other or separately. In some embodiments, 1, 2, 3, 4, 5, or 6 rings 4608 can be used. The rings 4608 can extend fully or partially around a circumference of the capsule 106. In some embodiments, the rings/spine 4608/4606 can be located radially inwards or radially outwards, or both, of the capsule 106. In some embodiments, one or more wires or stiff material axial runners can be added to the capsule 106 similar as discussed above.

FIG. 46B illustrates another modification, which includes a track and pin mechanism. As shown, the capsule 106 can include a track 4610 that extends along at least a portion of the inner surface of the longitudinal length of the capsule 106. Additionally, the inner retention member 40 can include a pin/protrusion/extension 4612 on its outer surface. The pin 4612 can be configured to mate with the track 4610 and follow along the track 4610 when the capsule 106 is withdrawn. The track 4610 can be located on an outer surface of the capsule 106 in some embodiments, and the pin 4612 can extend through the capsule 106.

In some embodiments, the track 4610 can include a portion 4611 that changes direction and moves circumferentially, or both circumferentially and longitudinally, such as shown in FIG. 46B. Thus, the inner retention member 40 can be rotated in order to release the prosthesis 70. This can be done by a user or automatically during operation. Other locking or release prevention mechanisms can be used as well.

Figures 47A, 47B:
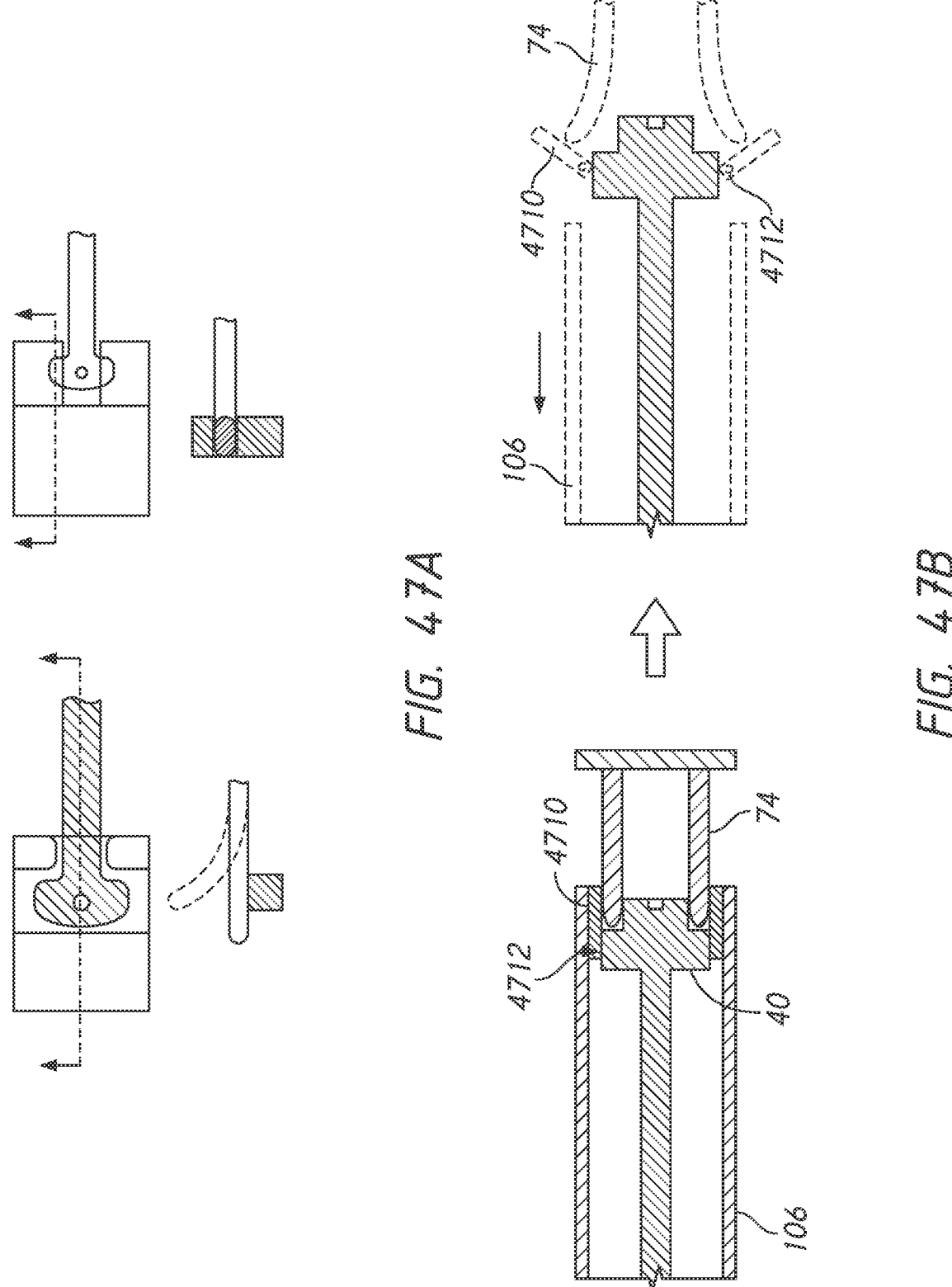
FIG. 47A illustrates an angled inner retention member groove structure.
FIG. 47B illustrates an inner retention ring including attachment flaps.

As shown in FIG. 47A, alternatively, or in conjunction, the inner retention member 40 geometry can be modified to lock the prosthesis 70 into the delivery system 10 without the need for an outer retention member 42. For example, as shown, the modification can be adding an angle to the inner retention ring 40 grooves such that the prosthesis 70 is held to the inner retention ring 40 while under tension. Thus, the angled section of the inner retention ring 40 can extend to partially cover the locking tab 74 of the prosthesis 70. Accordingly, this restricts radially outward motion of the locking tab 74 until the inner retention ring is transition distally to uncover the locking tab 74.

FIG. 47B illustrates another modification of the inner retention member 40 that can be used in conjunction with, or in alternative to, any of the configurations discussed above. As shown, the inner retention member 40 can be modified to include fins/flaps 4710 extending from a circumferentially outside surface. The flaps 4710 can be rotatably connected to the inner retention member 40 in some embodiments, such as at a pivot point 4712. In some embodiments, the flaps 4710 are flexible and can flex/bend outwards once released from the capsule 106.

In some embodiments, the flaps 4710 can be made of a soft material, for example a polymer, plastic, rubber, etc. such that as the inner retention member 40 and the capsule 106 transition so that the inner retention member 40 extends distal of the capsule 106, the flaps 4710 fold over the grooves and lock the prosthesis 70 into place. FIG. 47B illustrates the inner retention member 40 in the closed (left) and released (right) position.

In some embodiments, the delivery system 10 can also include a two-layer twist lock mechanism. For example, the ring 40 or the capsule 106 can be twisted to block the grooves in the ring 40. Thus, the grooves can be covered and lock the prosthesis 70 into place. The twisting could be activated by the user or could occur automatically as the inner retention ring 40 is transitioned with respect to the capsule 106.

Figure 48A:
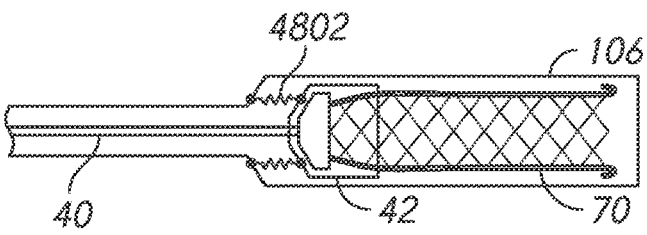
FIGS. 48A-D illustrate embodiments of a tethered outer retention member.

Alternatively, or in conjunction, as shown in FIGS. 48A-D, the outer retention member 42 can be tethered to the base of the capsule 106, which eliminates the mid shaft while retaining the current valve attachment mechanism. As shown in FIG. 48A, the outer retention member 42 can be free floating within the capsule 106. In some embodiments, the outer retention member 42 may follow tracks or otherwise be movably connected to the capsule 106. The outer retention member 42 can be attached to the capsule 106 through the use of at least one suture 4802 attached at a proximal end of the outer retention member 42. In some embodiments, two sutures 4802 located circumferentially opposite can be used. The suture 4802 can attach to the capsule 106, such as at an internal proximal portion of the capsule 106, for example where the capsule 106 reduces in diameter. Thus, as shown in FIG. 48A, when in the retracted position, the suture 4802 can be slackly held within the capsule 106.

Figure 48B:
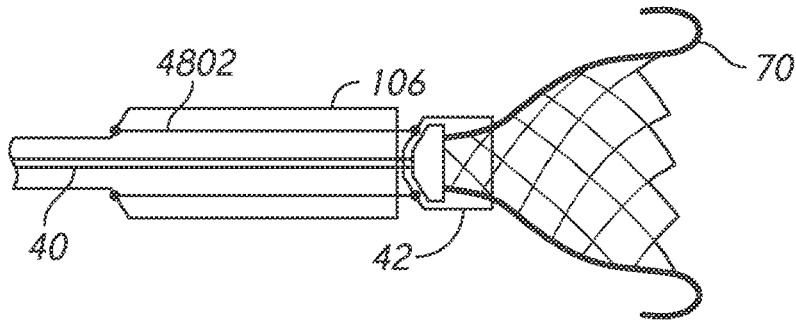

Once the capsule 106 is retracted, as shown in FIG. 48B, the suture 4802 can be extended to be tight between the capsule 106 and the outer retention member 42. Thus, the outer retention member 42 can be outside of the capsule 106 retaining the proximal end of the prosthesis 70.

Figure 48C:
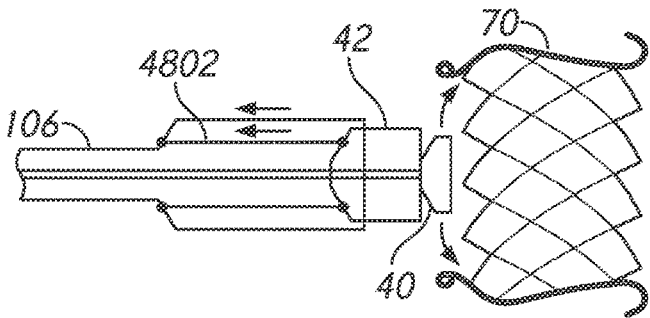
Figure 48D:
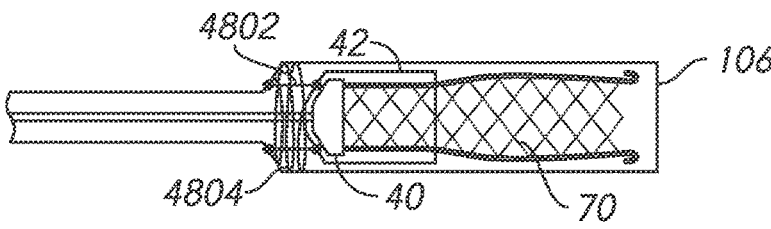

Continuing to retract the capsule 106, as shown in FIG. 48C, proximally retracts the outer retention member 42 connected by the sutures 4802, thereby releasing the prosthesis 70.

In some embodiments, a spring 4804 can be used in addition to or instead of the sutures 4802. Like the suture 4802, the spring 4804 can be attached between a proximal end of the outer retention member 42 and the capsule 106. The spring 4804 can provide active forward pressure on the outer retention member 42 to ensure the prosthesis 70 remains attached. The spring 4804 would compress during loading and stretch during deployment.

Figure 49:
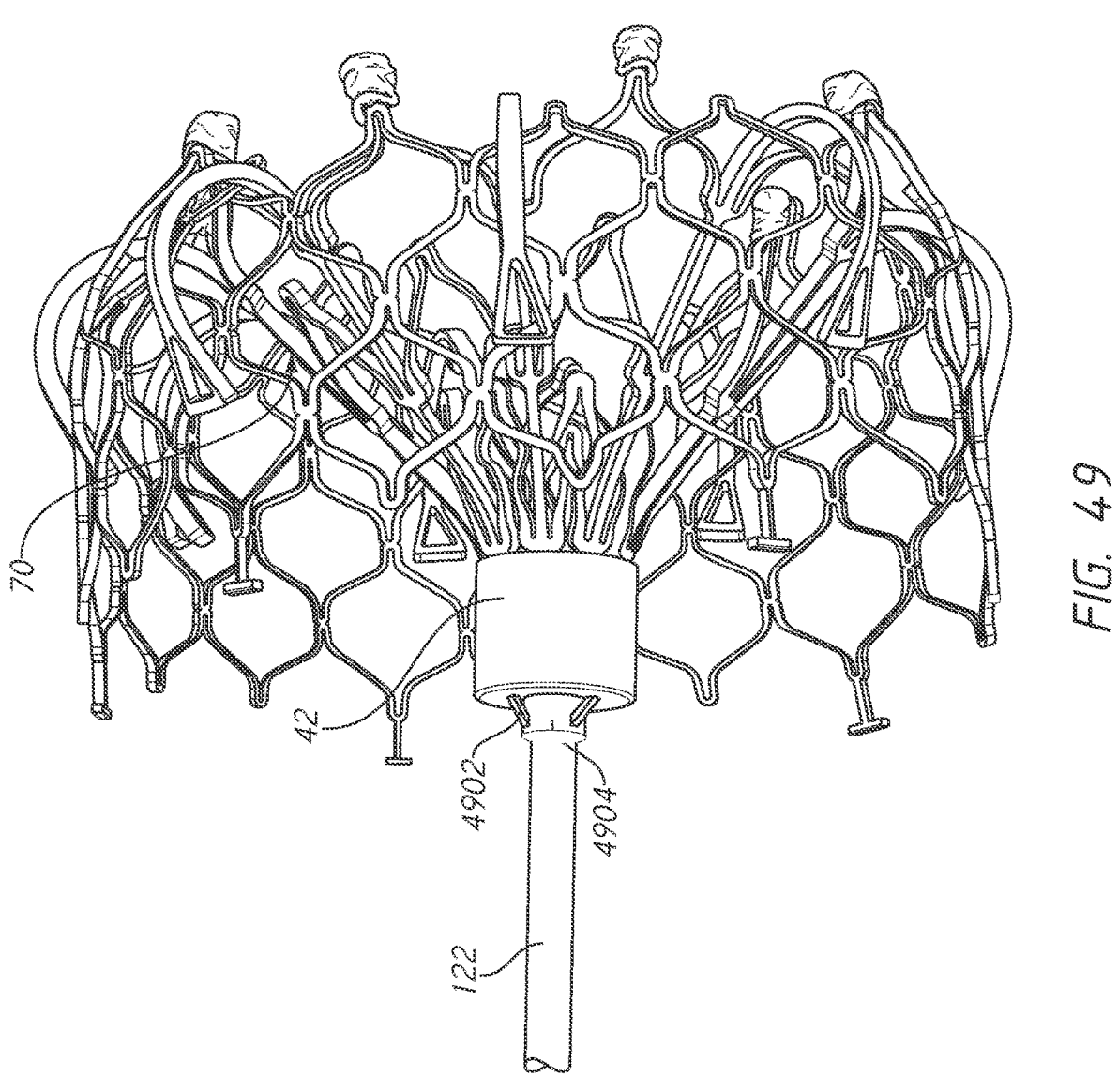
FIG. 49 illustrates an embodiment of an outer retention ring backstop.

FIG. 49 illustrates another prosthesis attachment mechanism which can utilize an outer retention ring backstop or locking feature. As shown, the outer sheath assembly 22 has been removed, and there is no mid shaft in this embodiment. Therefore, the inner shaft 122 can be more clearly seen.

At or near the distal end of the inner shaft 112, but proximal to the inner retention ring 40, the inner shaft 112 can include a number of tab s/protrusions/extensions/backstops/locking features 4902. In some embodiments, the tabs 4902 can extend directly from the inner shaft 112. In some embodiments, the delivery system 10 can include an additional collar 4904, which can fully or partially surround the inner shaft 112. In some embodiments, the collar 4904 can be permanently attached to the inner shaft 112. In some embodiments, the collar 4904 may be movable along the inner shaft 112.

The tabs 4902 may have a radially compacted and a radially extended position. In the radially compacted position, an outer retention ring 42 can slide distally over the tabs 4902. Once the outer retention ring 42 has moved distally over the tabs 4902, the tabs may extend radially outwards, as shown in FIG. 49. The tabs 4902 in the radially extended position may be larger than an inner diameter of the outer retention ring 42, thus preventing the outer retention ring 42 from moving proximally once the outer retention ring 42 has passed over the tabs 4902. In some embodiments, advancing the outer retention ring 42 distally over the tabs 4902 can collapse the tabs 4902 radially inwards to allow the outer retention ring 42 to pass over them. The tabs 4902 can prevent inadvertent release of the prosthesis 70, such as when the delivery system 10 is flexed or there is a length change of any of the shafts.

In some embodiments, the tabs 4902 can be translated to their radially compressed position by an operator in order to proximally translate the outer retention ring 42. For example, sutures may be attached to the tabs 4902. Thus, an operator may pull proximally on the sutures, such as by hand or through a knob on the handle, to compact the tabs 4902. By compacting the tabs 4902, the outer retention ring 42 can automatically move proximally to release a portion of the prosthesis 70. In some embodiments, the collar 4904 may be withdrawn proximally, again by an operator such as the use of a suture or pull wire, to allow the outer retention ring 42 to be withdrawn proximally.

The tabs 4902 may be a laser cut of a tube in some embodiments. The tabs 4902 may be radially compressible inwards, e.g., becoming more parallel to the inner shaft 112.

As shown, the tabs 4902 can extend at an angle away from the inner shaft 112 in a distal direction. In some embodiments, an angled between the tab 4902 and the inner shaft 112 or collar 4904 in an extended position can be 5, 10, 15, 20, 25, 30, 35, 40, 45, 50, 55, 60, 65, 70, 75, 80, 85, or 90 degrees.

In some embodiments, there may be 1, 2, 3, 4, 5, or 6 tabs 4902. In some embodiments, the tabs 4902 may be evenly spaced around a circumference of the inner shaft 112 or collar 4904. In some embodiments, the tabs 4902 are not evenly spaced.

Additional Valve Prostheses

Figure 50:
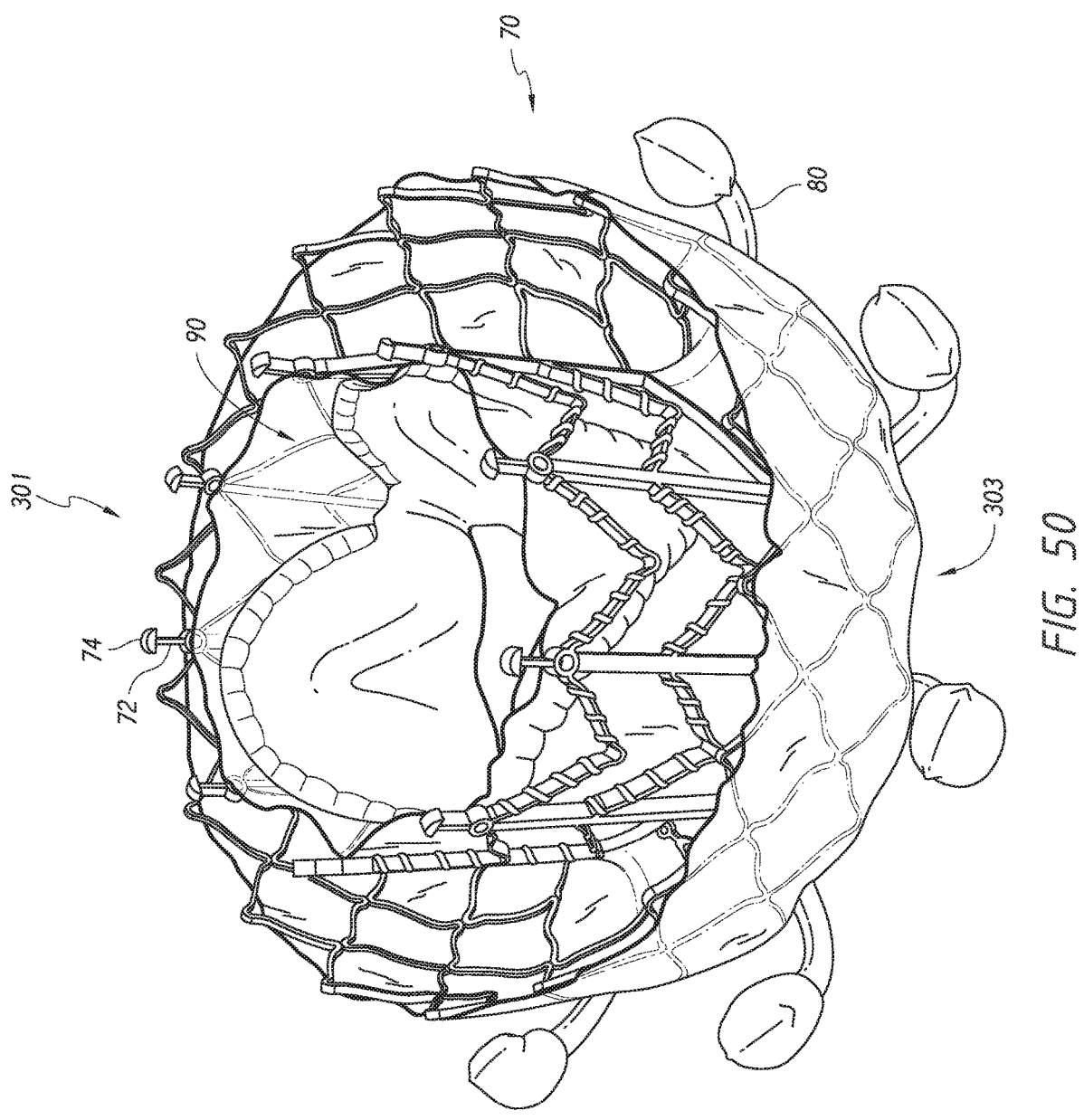
FIG. 50 shows a side view of an embodiment of a valve prosthesis that may be delivered using the delivery systems described herein.

FIGS. 50-53 illustrate alternative embodiments of a prosthesis that can used with the disclosed delivery systems 10 and methodology discussed herein. FIG. 50 illustrates one alternate embodiment of a prosthesis. Reference numbering of FIG. 50 are the same as discussed above with respect to FIG. 3A and further discussion can be found with respect to FIGS. 39-41 of U.S. Pat. Pub. No. 2018/0055629, hereby incorporated by reference in its entirety. FIGS. 51A-53 illustrates another alternate embodiment of a prosthesis and further discussion can be found with respect to FIG. 33-35 of U.S. Pat. Pub. No. 2018/0055629 except that an outer frame anchoring feature is described in this publication. These embodiments can have similar or the same features to the prostheses discussed herein. In some embodiments, the prosthesis may be a single frame prosthesis. In some embodiments, the prosthesis may be a dual frame prosthesis. In some embodiments for use as a replacement mitral valve, the prosthesis includes distal or ventricular anchors similar to those described above (see, for example, anchoring feature 1524 described below), but does not include proximal or atrial anchors.

Figure 51A:
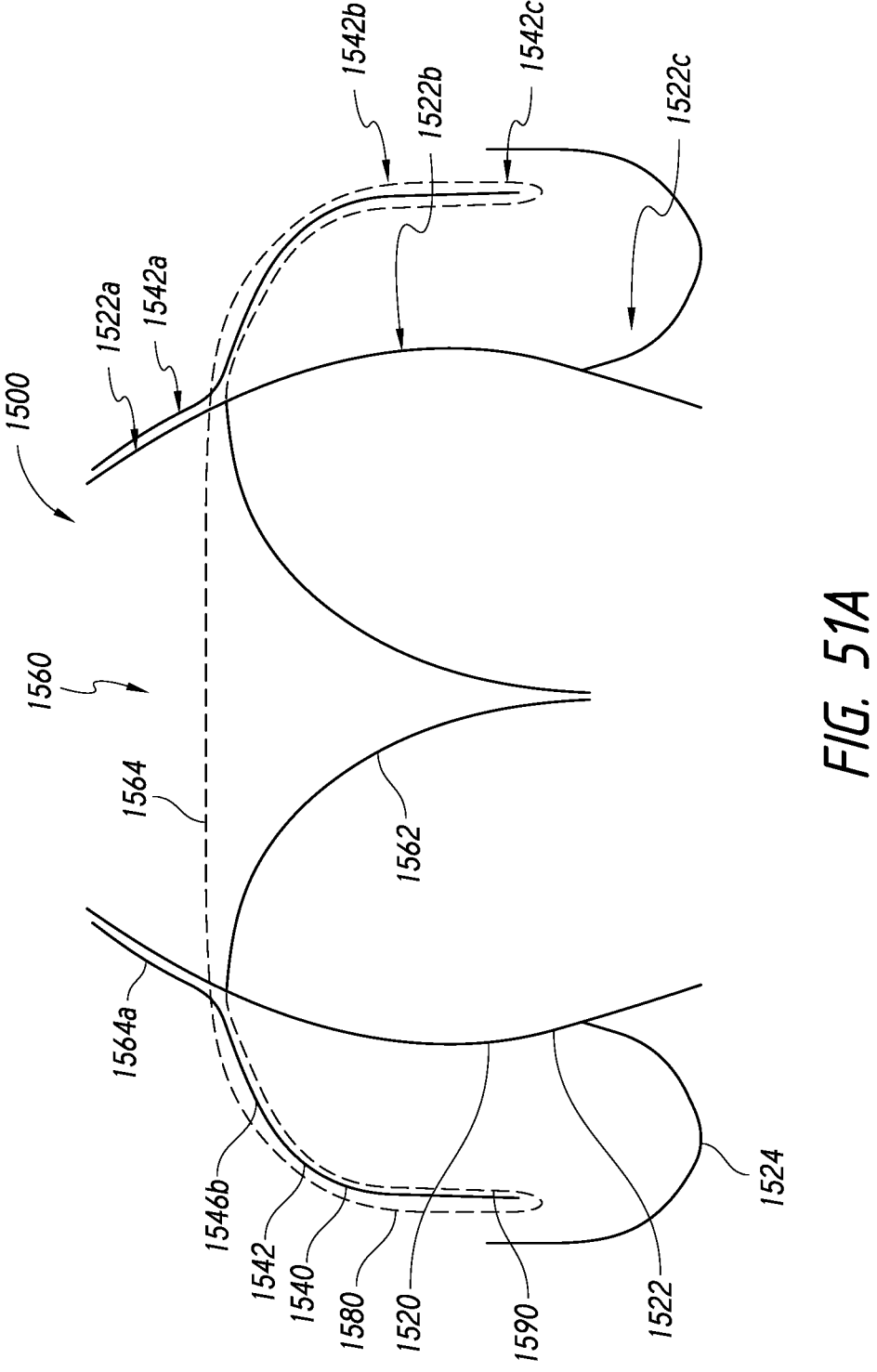
FIG. 51A-53 show views of an embodiment of a valve prosthesis that may be delivered using the delivery systems described herein.

With reference next to FIG. 51A, an embodiment of a prosthesis 1500 in an expanded configuration is illustrated. The prosthesis 1500 can include an inner frame 1520, an outer frame 1540, a valve body 1560, and one or more skirts, such as an outer skirt 1580 and an inner skirt 1590.

With reference first to the inner frame 1520, the inner frame 1520 can include an inner frame body 1522 and an inner frame anchoring feature 1524. The inner frame body 1522 can have an upper region 1522a, an intermediate region 1522b, and a lower region 1522c. As shown, the inner frame body 1522 can have a generally bulbous shape such that the diameters of the upper region 1522a and the lower region 1522c are less than the diameter of the intermediate region 1522b. The diameter of the upper region 1522a can be less than the diameter of the lower region 1522c. This can beneficially allow the use of a smaller valve body 1560 within the inner frame 1520 while allowing the inner frame body 1522 to have a larger diameter proximate the connection between the inner frame body 1522 and the inner frame anchoring feature 1524. This larger diameter can reduce the radial distance between the connection and the tip or end of the inner frame anchoring feature 1524. This can beneficially enhance fatigue resistance of the inner frame anchoring feature 1524 by reducing the length of the cantilever.

While the illustrated inner frame body 1522 is bulbous, it is to be understood that the diameters of the upper region 1522a, the intermediate region 1522b, and/or the lower region 1522c can be the same such that the inner frame body 1522 is generally cylindrical along one or more regions. Moreover, while the illustrated embodiment includes a lower region 1522a having a greater diameter than the upper region 1522c, it is to be understood that the diameters of the upper and lower regions 1522a, 1522c can be the same or the diameter of the upper region 1522a can be greater than the diameter of the lower region 1522c. Moreover, although the inner frame body 1522 has been described and illustrated as being cylindrical or having circular cross-sections, it is to be understood that all or a portion of the inner frame body 1522 can have a non-circular cross-section such as, but not limited to, a D-shape, an oval or an otherwise ovoid cross-sectional shape.

With reference next to the outer frame 1540 illustrated in FIG. 51A, the outer frame 1540 can be attached to the inner frame 1520 using any suitable fastener and/or other technique. Although the outer frame 1540 is illustrated as a separate component from the inner frame 1520, it is to be understood that the frames 1520, 1540 can be unitarily or monolithically formed.

As shown in the illustrated embodiment, the outer frame 1540 can include an outer frame body 1542. The outer frame body 1542 can have an upper region 1542a, an intermediate region 1542b, and a lower region 1542c. When in an expanded configuration such as a fully expanded configuration, the outer frame body 1542 can have an enlarged shape with the intermediate region 1542b and the lower region 1542c being larger than the upper region 1542a. The enlarged shape of the outer frame body 1542 can advantageously allow the outer frame body 1542 to engage a native valve annulus, native valve leaflets, or other tissue of the body cavity, while spacing the upper end from the heart or vessel wall.

The upper region 1542a of the outer frame body 1542 can include a first section 1546a and a second section 1546b. The first section 1546a can be sized and/or shaped to generally match the size and/or shape of the inner frame 1520. For example, the first section 1546a can have a curvature which matches a curvature of the upper region 1522a of the inner frame body 1522. The second section 1546b can extend radially outwardly away from the inner frame 1520. As shown in the illustrated embodiment, the transition between the first section 1546a and the second section 1546b can incorporate a bend such that the second section 1546b extends radially outwardly at a greater angle relative to the longitudinal axis.

The intermediate region 1542b of the outer frame body 1542 can extend generally downwardly from the outwardly-extending section 1546b of the upper region 1542a. As shown, the intermediate region 1542b can have a generally constant diameter from an upper end to a lower end such that the intermediate region 1542*b* forms a generally cylindrical shape. The lower region 1542*c* of the outer frame body 1542 can extend generally downwardly from the lower end of the intermediate region 1542*b*. As shown, the lower region 1542*c* of the outer frame body 1542 can have a generally constant diameter from an upper end to a lower end such that the lower region 1542*c* forms a generally cylindrical shape. As shown, the diameters of the intermediate region 1542*b* and the lower region 1542*c* are generally equivalent such that the intermediate region 1542*b* and the lower region 1542*c* together form a generally cylindrical shape.

While the intermediate and lower regions 1542*b*, 1542*c* have been described as cylindrical, it is to be understood that the diameters of the upper end, the lower end, and/or the portion therebetween can be different. For example, a diameter of the portion between the upper end and the lower end can be larger than the upper end and the lower end such that the intermediate region 1542*b* and/or lower region 1542*c* forms a generally bulbous shape. In some embodiments, the diameter of the lower end can be larger than the diameter of the upper end. In other embodiments, the diameter of the upper end can be larger than the diameter of the lower end. Moreover, although the outer frame body 1542 has been described and illustrated as being cylindrical or having circular cross-sections, it is to be understood that all or a portion of the outer frame body 1542 can be have a non-circular cross-section such as, but not limited to, a D-shape, an oval or an otherwise ovoid cross-sectional shape.

The outer frame 1540, such as the outer frame body 1542 can be used to attach or secure the prosthesis 1500 to a native valve, such as a native mitral valve. For example, the intermediate region 1542*b* of the outer frame body 1542 and/or the outer anchoring feature 1544 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1542 can be sized and positioned relative to the inner frame anchoring feature 1524 such that tissue of the body cavity positioned between the outer frame body 1542 and the inner frame anchoring feature 1524, such as native valve leaflets and/or a native valve annulus, can be engaged or pinched to further secure the prosthesis 1500 to the tissue.

With continued reference to the prosthesis 1500 illustrated in FIG. 51A, the valve body 1560 is attached to the inner frame 1520 within an interior of the inner frame body 1522. The valve body 1560 functions as a one-way valve to allow blood flow in a first direction through the valve body 1560 and inhibit blood flow in a second direction through the valve body 1560.

The valve body 1560 can include a plurality of valve leaflets 1562, for example three leaflets 1562, which are joined at commissures. The valve body 1560 can include one or more intermediate components 1564. The intermediate components 1564 can be positioned between a portion of, or the entirety of, the leaflets 1562 and the inner frame 1520 such that at least a portion of the leaflets 1542 are coupled to the frame 1520 via the intermediate component 1564. In this manner, a portion of, or the entirety of, the portion of the valve leaflets 1562 at the commissures and/or an arcuate edge of the valve leaflets 1562 are not directly coupled or attached to the inner frame 1520 and are indirectly coupled or "float" within the inner frame 1520. For example, a portion of, or the entirety of, the portion of the valve leaflets 1562 proximate the commissures and/or the arcuate edge of the valve leaflets 1562 can be spaced radially inward from an inner surface of the inner frame 1520. By using one or more intermediate components 1564, the valve leaflets 1562 can be attached to non-cylindrical frames 1520 and/or frames 1520 having a diameter larger than that of the diameter of the valve leaflets 1562.

With reference next to the outer skirt 1580 illustrated in FIG. 51A, the outer skirt 1580 can be attached to the inner frame 1520 and/or outer frame 1540. As shown, the outer skirt 1580 can be positioned around and secured to a portion of, or the entirety of, the exterior of the outer frame 1540. The skirt 1580 can also be secured to a portion of the valve body 1560 such as, but not limited to, the intermediate components 1564. For example, the skirt 1580 can be attached to an inflow region of the intermediate components 1564. As shown, the outer skirt 1580 can follow the contours of the outer frame 1540; however, it is to be understood that at least a portion of the skirt 1580 can be spaced apart from at least a portion of both the inner frame 1520 and the outer frame 1540.

With reference next to the inner skirt 1590 illustrated in FIG. 51A, the inner skirt 1590 can be attached to the valve body 1560 and the outer skirt 1580. As shown, a first end of the inner skirt 1590 can be coupled to the valve body 1560 along portions of the valve body 1560 which are proximate the inner frame 1520. A second end of the inner skirt 1590 can be attached to the lower region of the outer skirt 1580. In so doing, a smooth surface can be formed under each of the leaflets. This can beneficially enhance hemodynamics by allowing blood to more freely circulate and reducing areas of stagnation. In some embodiments, the inner skirt 1590 can beneficially reduce contact between the outer frame body 1542 and the inner frame body 1522.

Although the prosthesis 1500 has been described as including an inner frame 1520, an outer frame 1540, a valve body 1560, and skirts 1580, 1590, it is to be understood that the prosthesis 1500 need not include all components. For example, in some embodiments, the prosthesis 1500 can include the inner frame 1520, the outer frame 1540, and the valve body 1560 while omitting the skirt 1580. Moreover, although the components of the prosthesis 1500 have been described and illustrated as separate components, it is to be understood that one or more components of the prosthesis 1500 can be integrally or monolithically formed. For example, in some embodiments, the inner frame 1520 and the outer frame 1540 can be integrally or monolithically formed as a single component.

Figure 51B:
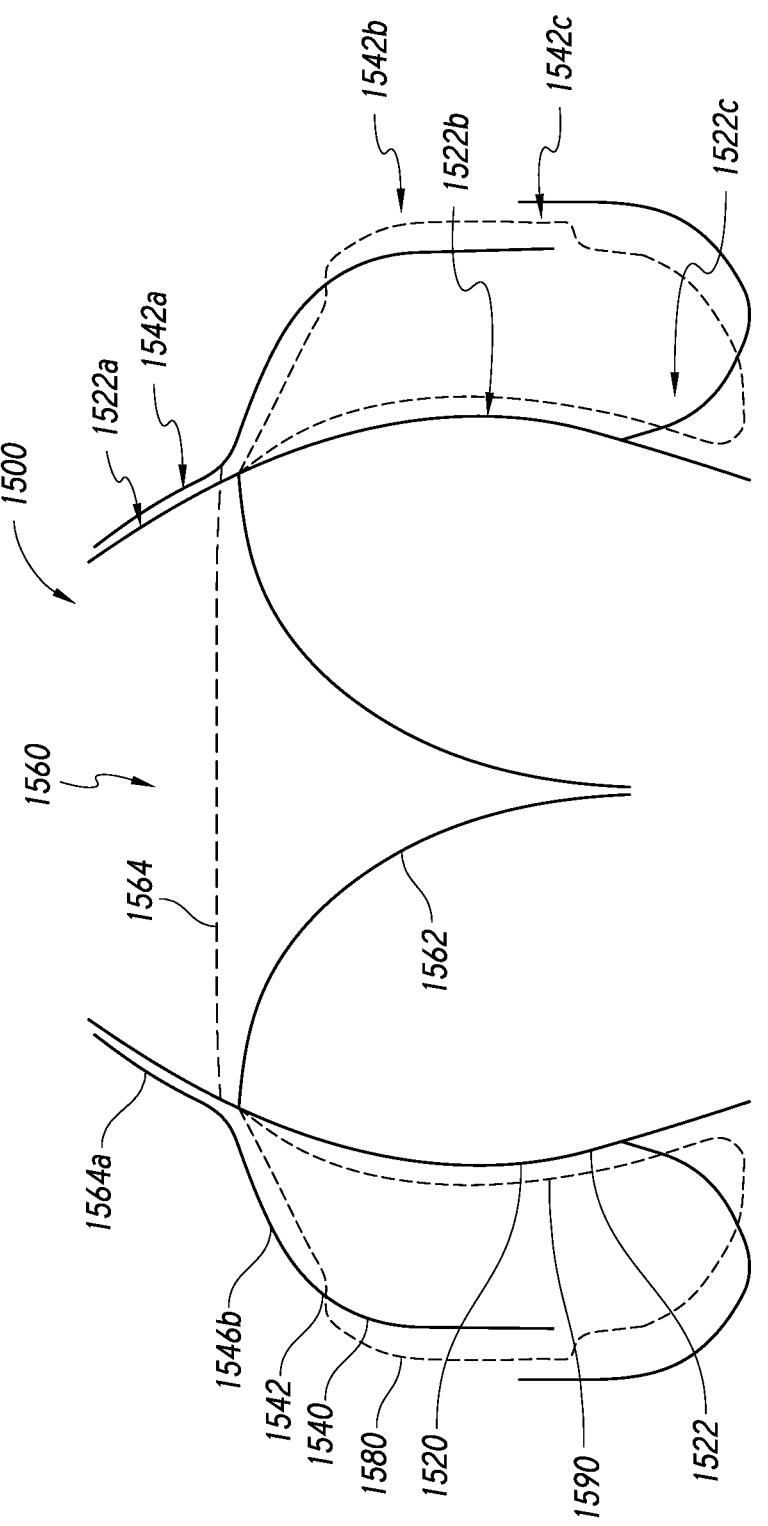

FIG. 51B illustrates an alternate embodiment of FIG. 51A with modifications to the design of the skirts (or cloth) 1580/1590. As shown, the skirts 1580/1590 can contact both the inner frame 1520 and outer frame 1540. The skirts 1580/1590 can start on the inside of the outer 1540, transition to the outside of the outer frame 1540, then attach to the bottom of the outside of the inner frame 1520, then proceed up along the outside of the inner frame 1520. By closing the skirts 1580/1590, this could avoid/reduce clot formation/embolization.

Figure 52:
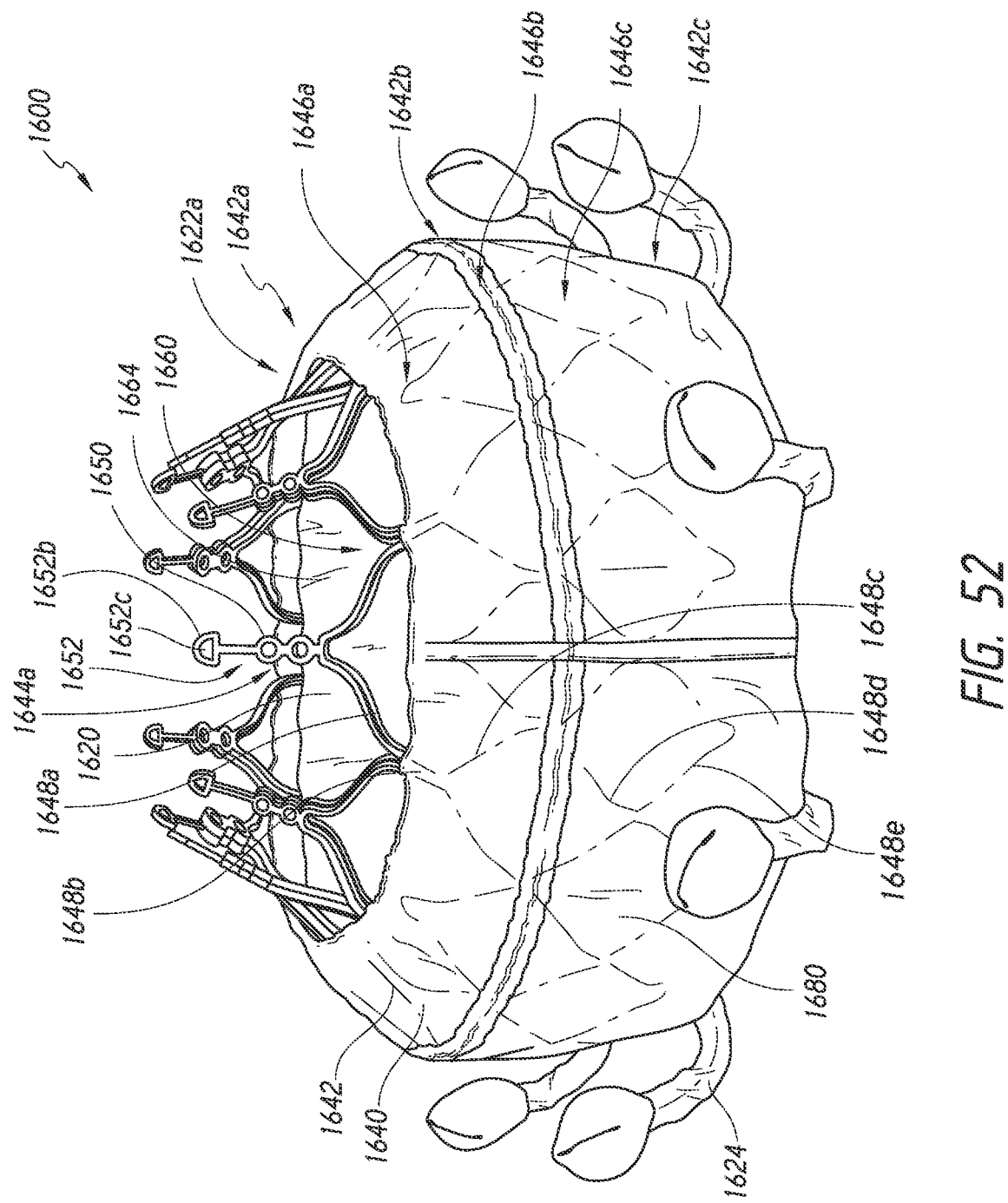
Figure 53:
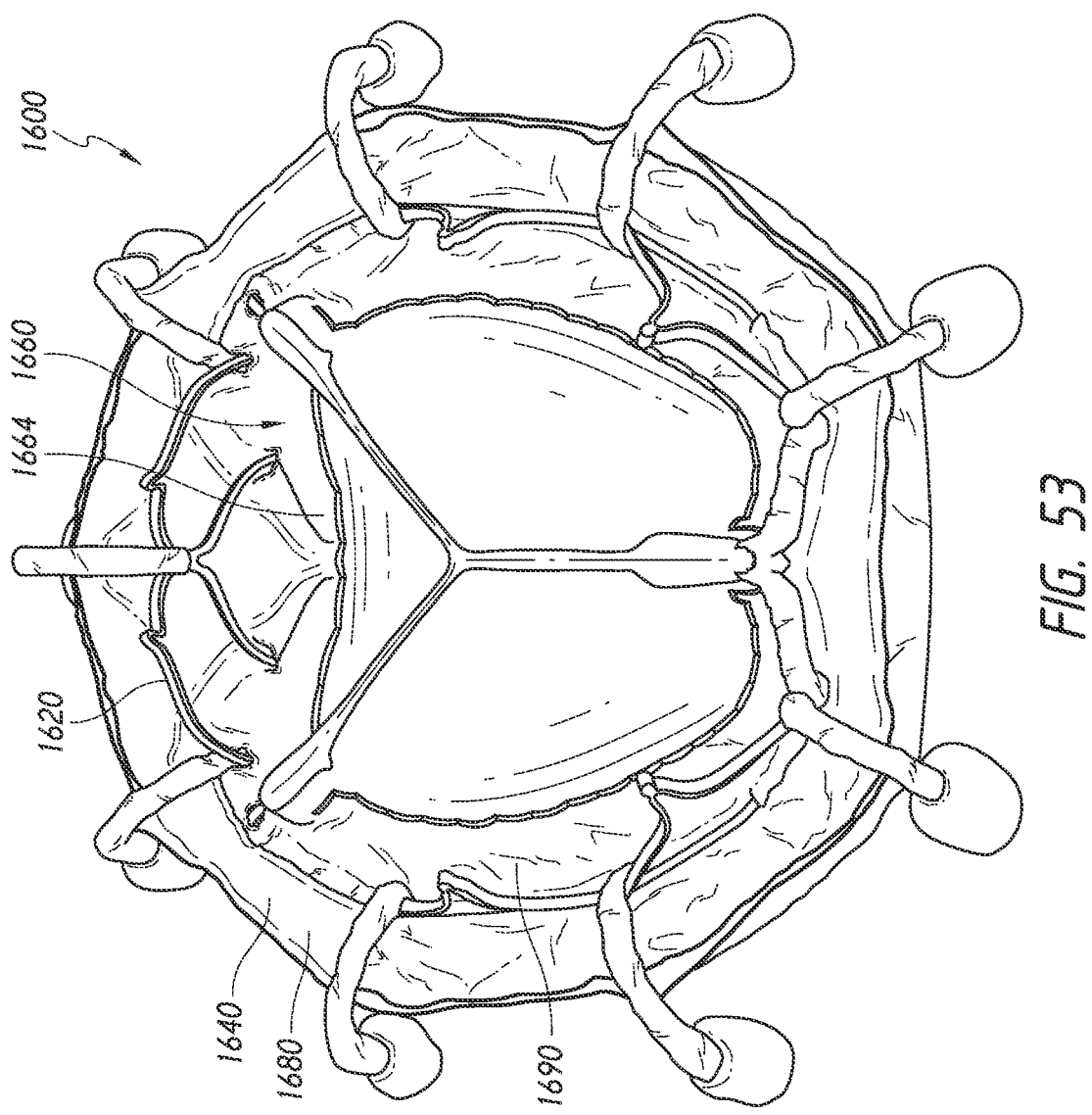

With reference next to FIGS. 52-53, an embodiment of a prosthesis 1600 in an expanded configuration is illustrated. This prosthesis 1600 may be similar in construction to the prosthesis 1500 described above. The prosthesis 1600 can include an inner frame 1620, an outer frame 1640, a valve body 1660, and one or more skirts, such as an outer skirt 1680 and an inner skirt 1690.

With reference first to the outer frame 1640 illustrated in FIGS. 52-53, the outer frame 1640 can be attached to the inner frame 1620 using any known fasteners and/or techniques. Although the outer frame 1640 is illustrated as a separate component from the inner frame 1620, it is to be understood that the frames 1620, 1640 can be unitarily or monolithically formed.

As shown in the illustrated embodiment, the outer frame 1640 can include an outer frame body 1642. The outer frame body 1642 can have an upper region 1642a, an intermediate region 1642b, and a lower region 1642c. At least a portion of the upper region 1642a of the outer frame body 1642 can be sized and/or shaped to generally match the size and/or shape of an upper region 1622a of the inner frame 1620. As shown in the illustrated embodiment, the upper region 1642a of the outer frame body 1642 can include one or more struts which generally match the size and/or shape of struts of the inner frame 1620. This can locally reinforce a portion of the prosthesis 1600 by effectively increasing the wall thickness of the combined struts.

When in an expanded configuration such as in a fully expanded configuration, the outer frame body 1642 can have a shape similar to that of outer frame body 1542 described above in connection with FIG. 51A. As shown, the intermediate region 1642b and the lower region 1642c can have a diameter which is larger than the diameter of the upper region 1642a. The upper region 1642a of the outer frame body 1642 can have a decreasing diameter from a lower end to an upper end such that the upper region 1642a is inclined or curved radially inwards towards the longitudinal axis of the prosthesis 1600. Although the outer frame body 1642 has been described and illustrated as being cylindrical or having circular cross-sections, it is to be understood that all or a portion of the outer frame body 1642 can be have a non-circular cross-section such as, but not limited to, a D-shape, an oval or an otherwise ovoid cross-sectional shape.

With continued reference to the outer frame 1600 illustrated in FIG. 52, the outer frame body 1642 can include a plurality of struts with at least some of the struts forming cells 1646a-c. Any number of configurations of struts can be used, such as rings of undulating struts shown forming ellipses, ovals, rounded polygons, and teardrops, but also chevrons, diamonds, curves, and various other shapes.

The upper row of cells 1646a can have an irregular octagonal shape such as a "heart" shape. This additional space can beneficially allow the outer frame 1640 to retain a smaller profile when crimped. The cell 1646a can be formed via a combination of struts. As shown in the illustrated embodiment, the upper portion of cells 1646a can be formed from a set of circumferentially-expansible struts 1648a having a zig-zag or undulating shape forming a repeating "V" shape. The struts 1648a can extend radially outwardly from an upper end to a lower end. These struts can generally match the size and/or shape of struts of the inner frame 1620.

The middle portion of cells 1646a can be formed from a set of struts 1648b extending downwardly from bottom ends of each of the "V" shapes. The struts 1648b can extend radially outwardly from an upper end to a lower end. The portion of the cells 1646a extending upwardly from the bottom end of struts 1648b may be considered to be a substantially non-foreshortening portion of the outer frame 1640.

The lower portion of cells 1646a can be formed from a set of circumferentially-expansible struts 1648c having a zig-zag or undulating shape forming a repeating "V" shape. As shown in the illustrated embodiment, the struts 1648c can incorporate a curvature such that the lower end of struts 1648c extend more parallel with the longitudinal axis than the upper end of the struts 1648c. One or more of the upper ends or tips of the circumferentially-expansible struts 1648c can be a "free" apex which is not connected to a strut. For example, as shown in the illustrated embodiment, every other upper end or tip of circumferentially-expansible struts 1648b is a free apex. However, it is to be understood that other configurations can be used. For example, every upper apex along the upper end can be connected to a strut.

The middle and/or lower rows of cells 1646b-c can have a different shape from the cells 1646a of the first row. The middle row of cells 1646b and the lower row of cells 1646c can have a diamond or generally diamond shape. The diamond or generally diamond shape can be formed via a combination of struts.

The upper portion of cells 1646b can be formed from the set of circumferentially-expansible struts 1648c such that cells 1646b share struts with cells 1646a. The lower portion of cells 1646b can be formed from a set of circumferentially-expansible struts 1648d. As shown in the illustrated embodiment, one or more of the circumferentially-expansible struts 1648d can extend generally in a downward direction generally parallel to the longitudinal axis of the outer frame 1640.

The upper portion of cells 1646c can be formed from the set of circumferentially-expansible struts 1648d such that cells 1646c share struts with cells 1646b. The lower portion of cells 1646c can be formed from a set of circumferentially-expansible struts 1648e. Circumferentially-expansible struts 1648e can extend generally in a downward direction.

As shown in the illustrated embodiment, there can be a row of nine cells 1646a and a row of eighteen cells 1646b-c. While each of the cells 1646a-c are shown as having the same shape as other cells 1646a-c of the same row, it is to be understood that the shapes of cells 1646a-c within a row can differ. Moreover, it is to be understood that any number of rows of cells can be used and any number of cells may be contained in the rows.

As shown in the illustrated embodiment, the outer frame 1600 can include a set of eyelets 1650. The upper set of eyelets 1650 can extend from an upper region 1642a of the outer frame body 1642. As shown, the upper set of eyelets 1650 can extend from an upper portion of cells 1646a, such as the upper apices of cells 1646a. The upper set of eyelets 1650 can be used to attach the outer frame 1640 to the inner frame 1620. For example, in some embodiments, the inner frame 1620 can include one or more eyelets which correspond to the eyelets 1650. In such embodiments, the inner frame 1620 and outer frame 1640 can be attached together via eyelets 1650 and corresponding eyelets on the inner frame 1620. For example, the inner frame 1620 and outer frame 1640 can be sutured together through said eyelets or attached via other means, such as mechanical fasteners (e.g., screws, rivets, and the like).

As shown, the set of eyelets 1650 can include two eyelets extending in series from each "V" shaped strut. This can reduce the likelihood that the outer frame 1640 twists along an axis of the eyelet. However, it is to be understood that some "V" shaped struts may not include an eyelet. Moreover, it is to be understood that a fewer or greater number of eyelets can extend from a "V" shaped strut.

The outer frame 1640 can include a set of locking tabs 1652 extending from at or proximate an upper end of the upper region 1642a. As shown, the locking tabs 1652 can extend upwardly from the set of eyelets 1650. The outer frame 1640 can include twelve locking tabs 1652, however, it is to be understood that a greater number or lesser number of locking tabs can be used. The locking tabs 1652 can include a longitudinally-extending strut 1652a. At an upper end of the strut 1652*a*, the locking tab 1652 can include an enlarged head 1652*b*. As shown, the enlarged head 1652*b* can have a semi-circular or semi-elliptical shape forming a "mushroom" shape with the strut 1652*a*. The locking tab 1652 can include an eyelet 1652*c* which can be positioned through the enlarged head 1652*b*. It is to be understood that the locking tab 1652 can include an eyelet at other locations, or can include more than a single eyelet.

The locking tab 1652 can be advantageously used with multiple types of delivery systems. For example, the shape of the struts 1652*a* and the enlarged head 1652*b* can be used to secure the outer frame 1640 to a "slot" based delivery system, such as the inner retention member 40 described above. The eyelets 1652*c* and/or eyelets 1650 can be used to secure the outer frame 1640 to a "tether" based delivery system such as those which utilize sutures, wires, or fingers to control delivery of the outer frame 1640 and the prosthesis 1600. This can advantageously facilitate recapture and repositioning of the outer frame 1640 and the prosthesis 1600 in situ.

The outer frame 1640, such as the outer frame body 1642 can be used to attach or secure the prosthesis 1600 to a native valve, such as a native mitral valve. For example, the intermediate region 1642*b* of the outer frame body 1642 and/or the outer anchoring feature 1644 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1642 can be sized and positioned relative to the inner frame anchoring feature 1624 such that tissue of the body cavity positioned between the outer frame body 1642 and the inner frame anchoring feature 1624, such as native valve leaflets and/or a native valve annulus, can be engaged or pinched to further secure the prosthesis 1600 to the tissue. As shown, the inner frame anchoring feature 1624 includes nine anchors; however, it is to be understood that a fewer or greater number of anchors can be used. In some embodiments, the number of individual anchors can be chosen as a multiple of the number of commissures for the valve body 1660. For example, for a valve body 1660 have three commissures, the inner frame anchoring feature 1624 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. In some embodiments, the number of individual anchors does not correspond to the number of commissures of the valve body 1660.

With continued reference to the prosthesis 1600 illustrated in FIGS. 52-53, the valve body 1660 is attached to the inner frame 1620 within an interior of the inner frame body 1622. The valve body 1660 functions as a one-way valve to allow blood flow in a first direction through the valve body 1660 and inhibit blood flow in a second direction through the valve body 1660.

The valve body 1660 can include a plurality of valve leaflets 1662, for example three leaflets 1662, which are joined at commissures. The valve body 1660 can include one or more intermediate components 1664. The intermediate components 1664 can be positioned between a portion of, or the entirety of, the leaflets 1662 and the inner frame 1620 such that at least a portion of the leaflets 1642 are coupled to the frame 1620 via the intermediate component 1664. In this manner, a portion of, or the entirety of, the portion of the valve leaflets 1662 at the commissures and/or an arcuate edge of the valve leaflets 1662 are not directly coupled or attached to the inner frame 1620 and are indirectly coupled or "float" within the inner frame 1620.

With reference next to the outer skirt 1680 illustrated in FIG. 52, the outer skirt 1680 can be attached to the inner frame 1620 and/or outer frame 1640. As shown, the outer skirt 1680 can be positioned around and secured to a portion of, or the entirety of, the exterior of the outer frame 1640. The inner skirt 1690 can be attached to the valve body 1660 and the outer skirt 1680. As shown in FIG. 53, a first end of the inner skirt 1690 can be coupled to the valve body 1660 along portions of the valve body 1660 which are proximate the inner frame 1620. A second end of the inner skirt 1690 can be attached to the lower region of the outer skirt 1680. In so doing, a smooth surface can be formed along under each of the leaflets. This can beneficially enhance hemodynamics by allowing blood to more freely circulate and reducing areas of stagnation.

Although the prosthesis 1600 has been described as including an inner frame 1620, an outer frame 1640, a valve body 1660, and skirts 1680, 1690, it is to be understood that the prosthesis 1600 need not include all components. For example, in some embodiments, the prosthesis 1600 can include the inner frame 1620, the outer frame 1640, and the valve body 1660 while omitting the skirt 1680. Moreover, although the components of the prosthesis 1600 have been described and illustrated as separate components, it is to be understood that one or more components of the prosthesis 1600 can be integrally or monolithically formed. For example, in some embodiments, the inner frame 1620 and the outer frame 1640 can be integrally or monolithically formed as a single component.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A delivery system for delivering a self-expandable replacement heart valve to a patient's native heart valve location, the delivery system comprising:
an outer sheath assembly comprising an outer shaft having an outer lumen and a proximal end and a distal end, wherein the outer sheath assembly comprises a collapsible capsule comprising an implant retention area configured to retain the self-expandable replacement heart valve in a compressed configuration; and
an inner assembly located within the outer lumen, the inner assembly comprising an inner shaft having an inner lumen and a proximal end and a distal end, wherein the inner assembly comprises an inner retention member configured to facilitate releasable attachment of the self-expandable replacement heart valve thereto;
wherein at least one shaft of the outer shaft and the inner shaft comprises four axial runners extending through separate axial lumens extending along and within a wall of the at least one shaft,
wherein each of the four axial runners comprises a wire having a free floating configuration in which the wire has no tension and a tensioned configuration in which the at least one shaft is forced into a straight rigid configuration,
wherein each wire has a length that extends from the distal end of the at least one shaft to a handle of the delivery system,
wherein a proximal end of each wire is permanently affixed to at least one knob of the handle,
wherein the at least one knob of the handle is configured to cause the wires to transition between the free floating configuration and the tensioned configuration,
wherein the at least one shaft is configured to form a proximal bend and a distal bend,
wherein the at least one shaft can bend in any direction when the wires are in the free floating configuration such that the at least one shaft is configured to have universal flexibility, and
wherein both the outer shaft and the inner shaft cannot bend when the wires are in the tensioned configuration as the wires force the at least one shaft into a straight rigid configuration along the wires with the wires bearing a load.

2. The delivery system of claim 1, wherein the wires are spaced apart by about 90 degrees circumferentially about a central longitudinal axis of the at least one shaft.

3. The delivery system of claim 1, wherein each of the wires can be individually tensioned and released by the at least one knob of the handle.

4. The delivery system of claim 1, wherein two or more of the wires can be tensioned and released at the same time by the at least one knob of the handle.

5. The delivery system of claim 1, wherein the collapsible capsule is formed of collapsible material.

6. The delivery system of claim 1, wherein the collapsible capsule comprises ePTFE material.

7. The delivery system of claim 1, wherein the collapsible capsule of the outer shaft comprises a braided tube in conjunction with a lasercut hypotube to provide both tension and compression benefits.

8. The delivery system of claim 1, wherein the collapsible capsule of the outer shaft comprises a braided tube on top of a coil.

9. The delivery system of claim 1, wherein the collapsible capsule comprises a flared distal section to facilitate recapture of the self-expandable replacement heart valve.

10. A delivery system for delivering a self-expandable replacement heart valve to a patient's native heart valve location, the delivery system comprising:
a proximal handle; and
a shaft assembly coupled to the proximal handle, the shaft assembly comprising a steerable shaft having a proximal end and a distal end,

wherein the steerable shaft comprises a plurality of axial runners extending through at least two separate axial lumens extending along and within a wall of the steerable shaft, wherein each of the plurality of axial runners comprises a wire having a free floating configuration in which the wire has no tension and a tensioned configuration in which the steerable shaft is forced into a straight rigid configuration, wherein each wire has a length that extends from a location distal of the distal end of the steerable shaft to the proximal handle proximal to a proximal end of the steerable shaft, wherein a proximal end of each of the wires is permanently affixed to an actuator in the proximal handle, wherein the proximal handle is configured to cause the wires to transition between the free floating configuration and the tensioned configuration, and

wherein the steerable shaft is adapted to bend in any direction when the wires are in the free floating configuration, and wherein the steerable shaft cannot bend when the wires are in the tensioned configuration.

11. The delivery system of claim 10, wherein two of the wires are spaced apart by about 180 degrees circumferentially about a central longitudinal axis of the steerable shaft.

12. The delivery system of claim 10, wherein each of the wires can be individually tensioned and released by the proximal handle.

13. The delivery system of claim 10, wherein two or more of the wires can be tensioned and released at the same time by the proximal handle.

14. The delivery system of claim 10, wherein the actuator is a rotatable knob.

15. The delivery system of claim 10, wherein the shaft assembly further comprises a collapsible capsule positioned radially outward of the steerable shaft.

* * * * *